United States Patent
Hale et al.

(10) Patent No.: US 6,962,936 B2
(45) Date of Patent: Nov. 8, 2005

(54) TRIAZOLE-DERIVED KINASE INHIBITORS AND USES THEREOF

(75) Inventors: Michael R. Hale, Bedford, MA (US); Francois Maltais, Tewksbury, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 387 days.

(21) Appl. No.: 10/134,122

(22) Filed: Apr. 26, 2002

(65) Prior Publication Data

US 2003/0158238 A1 Aug. 21, 2003

Related U.S. Application Data

(60) Provisional application No. 60/287,204, filed on Apr. 27, 2001.

(51) Int. Cl.$^7$ .......................... A01N 43/64; A61K 31/41
(52) U.S. Cl. ....................... 514/381; 514/359; 514/383; 548/225; 548/264.8; 548/250; 548/256; 548/127; 544/343; 544/336; 544/345; 544/106
(58) Field of Search .............................. 548/225, 264.8, 548/250, 256, 127; 514/359, 381, 383; 546/257, 156, 199; 544/343, 336, 106, 345

(56) References Cited

FOREIGN PATENT DOCUMENTS

| WO | WO 95/31451 | 11/1995 |
| WO | WO 98/52941 | 11/1998 |
| WO | WO 01/56993 | 8/2001 |

OTHER PUBLICATIONS

Dornow et al., Chemische Berichte 1958, 91, 1841–1851.*
Aykut et al., A Quantum–Chemical Study on3,3'–bi(1,2,4–Triazole), Models in Chemistry, 133, 1–2, pp 43–51, 1996.*

* cited by examiner

*Primary Examiner*—Johann Richter
*Assistant Examiner*—Chukwuma Nwaonicha
(74) *Attorney, Agent, or Firm*—Andrea L.C. Robidoux; Choate, Hall & Stewart LLP

(57) ABSTRACT

Described herein are compounds that are useful as protein kinase inhibitors having the formula:

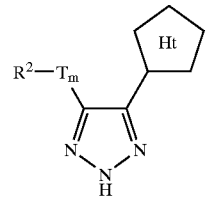

I where Ht, $R^2$, T, and m are as described in the specification. The compounds are useful for treating diseases in mammals that are alleviated by a protein kinase inhibitor, particularly diseases such as cancer, inflammatory disorders, restenosis, and cardiovascular disease.

22 Claims, No Drawings

TRIAZOLE-DERIVED KINASE INHIBITORS AND USES THEREOF

CROSS REFERENCE TO RELATED APPLICATIONS

This application claims priority to U.S. Provisional Application No. 60/287,204, filed Apr. 27, 2001, the contents of which are incorporated herein by reference.

TECHNICAL FIELD OF THE INVENTION

The present invention is in the field of medicinal chemistry and relates to triazole compounds that are protein kinase inhibitors, especially inhibitors of ERK, compositions containing such compounds and methods of use. The compounds are useful for treating cancer and other diseases that are alleviated by protein kinase inhibitors.

BACKGROUND OF THE INVENTION

Mammalian mitogen-activated protein (MAP) kinases are serine/threonine kinases that mediate intracellular signal transduction pathways (Cobb and Goldsmith, 1995, *J. Biol. Chem.*, 270, 14843; Davis, 1995, *Mol. Reprod. Dev.* 42, 459). Members of the MAP kinase family share sequence similarity and conserved structural domains, and include the ERK2 (extracellular signal regulated kinase), JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., 1994, *Cell* 76, 1025; Han et al., 1994, *Science* 265, 808; Raingeaud et al., 1995, *J. Biol. Chem.* 270, 7420; Shapiro and Dinarello, 1995, *Proc. Natl. Acad. Sci. USA* 92, 12230). In contrast, ERKs are activated by mitogens and growth factors (Bokemeyer et al. 1996, *Kidney Int.* 49, 1187).

ERK2 is a widely distributed protein kinase that achieves maximum activity when both Thr183 and Tyr185 are phosphorylated by the upstream MAP kinase kinase, MEK1 (Anderson et al., 1990, *Nature* 343, 651; Crews et al., 1992, *Science* 258, 478). Upon activation, ERK2 phosphorylates many regulatory proteins, including the protein kinases Rsk90 (Bjorbaek et al., 1995, *J. Biol. Chem.* 270, 18848) and MAPKAP2 (Rouse et al., 1994, *Cell* 78, 1027), and transcription factors such as ATF2 (Raingeaud et al., 1996, *Mol. Cell Biol.* 16, 1247), Elk-1 (Raingeaud et al. 1996), c-Fos (Chen et al., 1993 *Proc. Natl. Acad. Sci. USA* 90, 10952), and c-Myc (Oliver et al., 1995, *Proc. Soc. Exp. Biol. Med.* 210, 162). ERK2 is also a downstream target of the Ras/Raf dependent pathways (Moodie et al., 1993, *Science* 260, 1658) and may help relay the signals from these potentially oncogenic proteins. ERK2 has been shown to play a role in the negative growth control of breast cancer cells (Frey and Mulder, 1997, *Cancer Res.* 57, 628) and hyperexpression of ERK2 in human breast cancer has been reported (Sivaraman et al., 1997, *J. Clin. Invest.* 99, 1478). Activated ERK2 has also been implicated in the proliferation of endothelin-stimulated airway smooth muscle cells, suggesting a role for this kinase in asthma (Whelchel et al., 1997, *Am. J. Respir. Cell Mol. Biol.* 16, 589).

A number of compounds have been developed that purport to specifically inhibit various MAPKs. PCT publication WO 95/31451 describes pyrazole derivatives that inhibit p38. However, it is not clear whether these compounds have the appropriate pharmacological profiles to be therapeutically useful.

Aryl-substituted pyrroles are known in the literature. In particular, tri-aryl pyrroles (U.S. Pat. No. 5,837,719) have been described as having glucagon antagonist activity.

Heterocycle-substituted triazole compounds are known in the literature. In particular, bis([1,2,3]triazoles) (Abbasoglu et al., 1999, *Indian J. Chem., Sect. B* 38B, 413; Klaus, 1989, *Chem. Ber.* 122, 1175; Samsonov et al., 1993; *Khim. Geterotsikl. Soedin.* 29, 1169) and tetrazolyl-triazole (Ried and Laoutidis, 1990, *Chem.-Ztg.* 114, 246; Vereshchagin et al., 1984, *Zh. Org. Khim.* 20, 142) compounds have been described.

There is a high unmet medical need to develop new therapeutic treatments that are useful in treating the various conditions associated with ERK2 activation. For many of these conditions the currently available treatment options are inadequate.

Accordingly, there is great interest in new and effective inhibitors of protein kinase, including ERK2 inhibitors, which are useful in treating various conditions associated with protein kinase activation.

SUMMARY OF THE INVENTION

The present invention provides compounds and compositions thereof that are useful as protein kinase inhibitors, especially as inhibitors of ERK. These compounds can be used alone or in combination with other therapeutic or prophylactic agents, such as antibiotics, immunomodulators or other anti-inflammatory agents, for the treatment or prophylaxis of diseases mediated by protein kinases, including ERK2. According to a preferred embodiment, the compounds of this invention are capable of binding to the active site of ERK2 and inhibiting the activity of that enzyme.

It is a principal object of this invention to provide compounds that are protein kinase inhibitors represented by formula I:

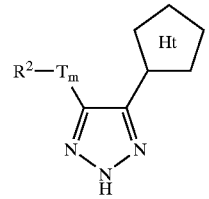

or a pharmaceutically acceptable derivative thereof, wherein:

Ht is a heterocyclic ring selected from pyrrol-3-yl, [1,2,4]triazol-3-yl, [1,2,3]triazol-4-yl, or tetrazol-5-yl, said pyrrol-3-yl having $R^3$ and $Q_n$-$R^4$ substituents, and said [1,2,4]triazol-3-yl or [1,2,3]triazol-4-yl substituted by either $R^3$ or $Q_n$-$R^4$;

T and Q are each independently selected from —C($R^7$)$_2$—, —C(O)—, —C(O)C(O)—, —C(O)NR$^7$—, —C(O)NR$^7$NR$^7$—, —CO$_2$—, —OC(O)—, —NR$^7$CO$_2$—, —O—, —NR$^7$C(O)NR$^7$—, —OC(O)NR$^7$—, —NR$^7$NR$^7$—, —NR$^7$C(O)—, —S—, —SO—, —SO$_2$—, —NR$^7$—, —SO$_2$NR$^7$—, or —NR$^7$SO$_2$—, —NR$^7$SO$_2$NR$^7$—;

m and n are each independently selected from zero or one;

$R^2$ is selected from hydrogen, CN, halogen, R, N($R^7$)$_2$, OR, or OH;

each $R^3$ is independently selected from $R^7$, F, Cl, —(CH$_2$)$_y$N($R^7$)$_2$, —N($R^7$)$_2$, —OR$^7$, —SR$^7$, —NR$^7$C(O)R$^7$, —NR$^7$C(O)N($R^7$)$_2$, —C(O)N($R^7$)$_2$, —SO$_2$R$^7$, —NR$^7$SO$_2$R$^7$, —C(O)R$^7$, —C(O)OR$^7$, CN or —SO$_2$N($R^7$)$_2$;

$R^4$ is selected from —$(CH_2)_yR^6$, —$(CH_2)_yCH(R^6)_2$, —$(CH_2)_yCH(R^8)CH(R^6)_2$, —$N(R^5)_2$, —$NR^5(CH_2)_yN(R^5)_2$;

each R is independently selected from an optionally substituted group selected from $C_{1-6}$ aliphatic, $C_{6-10}$ aryl, heteroaryl having 5–10 ring atoms, and heterocyclyl having 3–10 ring atoms;

each $R^5$ is independently selected from R, —$R^7$, —$C(O)R^7$, —$CO_2R$, —$C(O)N(R^7)_2$, —$SO_2R^7$, —$(CH_2)_yR^6$, or —$(CH_2)_yCH(R^6)_2$;

y is 0–6;

each $R^6$ is independently selected from R, —$(CH_2)_yR$, —OR, —$CO_2R$, —$(CH_2)_yN(R^7)_2$, —$N(R^7)_2$, —$OR^7$, —$SR^7$, —$NR^7C(O)R^7$, —$NR^7C(O)N(R^7)_2$, —$C(O)N(R^7)_2$, —$SO_2R^7$, —$NR^7SO_2R^7$, —$C(O)R^7$, —CN, —$SO_2N(R^7)_2$;

each $R^7$ is independently selected from hydrogen or an optionally substituted $C_{1-6}$ aliphatic group, or two $R^7$ on the same nitrogen are taken together with the nitrogen to form a 5–8 membered ring heterocyclyl or heteroaryl ring;

each $R^8$ is independently selected from R, —$(CH_2)_wOR^7$, —$(CH_2)_wN(R^5)_2$, or —$(CH_2)_wSR^7$;

each w is independently 0–4;

provided that when Ht is tetrazol-5-yl, and m is 0, $R^2$ is other than H or an unsubstituted phenyl; when m is 0 and $R^2$, $R^3$ and $Q_n$—$R^4$ are all H, Ht is other than [1,2,3]triazole; and when $T_m$—$R^2$ and $Q_n$—$R^4$ are both C(O)OH, Ht is other than [1,2,3]triazol-5-yl.

It is a further objective of this invention to provide pharmaceutical compositions comprising the protein kinase inhibitors of this invention. In a preferred embodiment, the protein kinase inhibitors inhibit ERK2. These compositions may be utilized in methods for treating or preventing a variety of protein kinase-mediated disorders, such as cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. Each of the above-described methods is also part of the present invention.

It is a further objective of this invention to provide methods for making the compounds and compositions of this invention.

DETAILED DESCRIPTION OF THE INVENTION

The present invention relates to compounds of formula I. Accordingly, it has now been found that compounds of this invention and compositions thereof are effective as protein kinase inhibitors, especially as inhibitors of ERK2.

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of the other. Also, combinations of substituents or variables are permissible only if such combinations result in a chemically stable arrangement.

The term "chemically stable arrangement" or "chemically feasible and stable" as used herein, refers to a compound structure that renders the compound sufficiently stable to allow manufacture and administration to a mammal by methods known in the art. Typically, such compounds are stable at a temperature of 40° C. or less, in the absence of moisture or other chemically reactive conditions, for at least a week.

The term "aliphatic" or "aliphatic group" as used herein means a straight-chain or branched $C_1$–$C_{12}$ hydrocarbon chain that is completely saturated or that contains one or more units of unsaturation, or a monocyclic $C_3$–$C_8$ hydrocarbon or bicyclic $C_8$–$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3–7 members. For example, suitable aliphatic groups include, but are not limited to, linear or branched or alkyl, alkenyl, alkynyl groups and hybrids thereof such as (cycloalkyl)alkyl, (cycloalkenyl) alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aryl" used alone or as part of a larger moiety as in "aralkyl", "aralkoxy," or "aryloxyalkyl," refers to monocyclic, bicyclic and tricyclic carbocyclic ring systems having a total of five to fourteen members, wherein at least one ring in the system is aromatic and wherein each ring in the system contains 3 to 7 ring members. The term "aryl" may be used interchangeably with the term "aryl ring".

The term "heterocycle", "heterocyclyl", or "heterocyclic" as used herein means non-aromatic, monocyclic, bicyclic or tricyclic ring systems having five to fourteen ring members in which one or more ring members is a heteroatom, wherein each ring in the system contains 3 to 8 ring members.

The term "heteroaryl", used alone or as part of a larger moiety as in "heteroaralkyl" or "heteroarylalkoxy", refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl, heteroarylalkoxy and the like) group may contain one or more substituents. Suitable substituents on the unsaturated carbon atom of an aryl, heteroaryl, aralkyl, or heteroaralkyl group are selected from halogen; haloalkyl; —$CF_3$; —$R^0$; —$OR^0$; —$SR^0$; 1,2-methylenedioxy; 1,2-ethylenedioxy; protected OH (such as acyloxy); phenyl (Ph); Ph substituted with $R^0$; —O(Ph); —O(Ph) substituted with $R^0$; —$CH_2$(Ph); —$CH_2$(Ph) substituted with $R^0$; —$CH_2CH_2$(Ph); —$CH_2CH_2$(Ph) substituted with $R^0$; —$NO_2$; —CN; —$N(R^0)_2$; —$NR^0C(O)R^0$; —$NR^0C(O)N(R^0)_2$; —$NR^0CO_2R^0$; —$NR^0NR^0C(O)R^0$; —$NR^0NR^0C(O)N(R^0)_2$; —$NR^0NR^0CO_2R^0$; —C(O)C(O)

R⁰; —C(O)CH₂C(O)R⁰; —CO₂R⁰; —C(O)R⁰; —C(O)N(R⁰)₂; —OC(O)N(R⁰)₂; —S(O)₂R⁰; —SO₂N(R⁰)₂; —S(O)R⁰; —NR⁰SO₂N(R⁰)₂; —NR⁰SO₂R⁰; —C(=S)N(R⁰)₂; —C(=NH)—N(R⁰)₂; —(CH₂)$_y$NHC(O)R⁰; —(CH₂)$_y$R⁰; —(CH₂)$_y$NHC(O)NHR⁰; —(CH₂)$_y$NHC(O)OR⁰; —(CH₂)$_y$NHS(O)R⁰; —(CH₂)$_y$NHSO₂R⁰; —(CH₂)$_y$NHC(O)CH(V$_z$—R⁰) (R⁰); wherein each R⁰ is independently selected from H, optionally substituted C$_{1-6}$ aliphatic, an unsubstituted 5–10 membered heteroaryl or heterocyclic ring, phenyl (Ph), —O(Ph), or —CH₂(Ph); wherein y is 0–6; z is 0–1; and V is a linker group. When R⁰ is C$_{1-6}$ aliphatic, it may be substituted with one or more substituents selected from —NH₂, —NH(C$_{1-4}$ aliphatic), —N(C$_{1-4}$ aliphatic)₂, —S(O)(C$_{1-4}$ aliphatic), —SO₂(C$_{1-4}$ aliphatic), halogen, —C$_{1-4}$ aliphatic, —OH, —O—(C$_{1-4}$ aliphatic), nitro, cyano, —CO₂H, —CO₂(C$_{1-4}$ aliphatic), —O(halo C$_{1-4}$ aliphatic), or -halo(C$_{1-4}$ aliphatic); wherein each C$_{1-4}$ aliphatic is unsubstituted.

An aliphatic group or a non-aromatic heterocyclic ring may contain one or more substituents. Suitable substituents on the saturated carbon of an aliphatic group or of a non-aromatic heterocyclic ring are selected from those listed above for the unsaturated carbon of an aryl or heteroaryl group and the following: =O, =S, =NNHR⁹, =NN(R⁹)₂, =N—, OR⁹, =NNHC(O)R⁹, =NNHCO₂(alkyl), =NNHSO₂(alkyl), or =NR⁹, where each R⁹ is independently selected from hydrogen or an optionally substituted C$_{1-6}$ aliphatic group. When R⁹ is C$_{1-6}$ aliphatic, it may be substituted with one or more substituents selected from amino, halogen, nitro, cyano, carboxy, t-butoxy, methoxy, ethoxy, hydroxy, or CF₃.

Substituents on the nitrogen of a non-aromatic heterocyclic ring are selected from —R¹⁰, —N(R¹⁰)₂, —C(O)R¹⁰, —CO₂R¹⁰, —C(O)C(O)R¹⁰, —C(O)CH₂C(O)R¹⁰, —SO₂R¹⁰, —SO₂N(R¹⁰)₂, —C(=S)N(R¹⁰)₂, —C(=NH)—N(R¹⁰)₂, and —NR¹⁰SO₂R¹⁰; wherein each R¹⁰ is independently selected from H, an optionally substituted C$_{1-6}$ aliphatic, optionally substituted phenyl (Ph), optionally substituted —O(Ph), optionally substituted CH₂(Ph), optionally substituted —CH₂CH₂(Ph), or an unsubstituted 5–6 membered heteroaryl or heterocyclic ring. When R¹⁰ is a C$_{1-6}$ aliphatic group or a phenyl ring, it may be substituted with one or more substituents selected from NH₂, NH(C$_{1-4}$ aliphatic), —N(C$_{1-4}$ aliphatic)₂, halogen, —C$_{1-4}$ aliphatic, —OH, —O—(C$_{1-4}$ aliphatic), nitro, cyano, —CO₂H, —CO₂(C$_{1-4}$ aliphatic), —O(halo C$_{1-4}$ aliphatic), or -halo(C$_{1-4}$ aliphatic), wherein each C$_{1-4}$ aliphatic is unsubstituted.

The term "linker group" or "linker" means an organic moiety that connects two parts of a compound. Linkers are comprised of —O—, —S—, —NH—, —CH₂—, —CO—, or an alkylidene chain. The alkylidene chain is a saturated or unsaturated, straight or branched, C$_{1-6}$ carbon chain which is optionally substituted, and wherein up to two non-adjacent saturated carbons of the chain are optionally replaced by —C(O)—, —C(O)C(O)—, —C(O)NR*-, —C(O)NR*NR*-, —CO₂—, —OC(O)—, —NR*CO₂—, —O—, —NR*C(O)NR*-, —OC(O)NR*-, —NR*NR*-, —NR*C(O)—, —S—, —SO—, —SO₂—, —NR*-, —SO₂NR*-, or —NR*SO₂—; wherein R* is selected from hydrogen or C$_{1-4}$ aliphatic. Optional substituents on the alkylidene chain are as described above for an aliphatic group.

As used herein, linker group Q, when present, connects Ht with R⁴. Q may form additional interactions within the ERK binding site to further enhance the inhibitory activity of the compound. When Q is a carbonyl-containing moiety such as —C(O)—, —CO₂—, —OC(O)—, —C(O)C(O)—, —C(O)NH—, —CO₂NH—, —C(O)NHNH—, —NHC(O)—, —OC(O)NH—, or —NHCO₂—, or a sulfonyl-containing moiety such as —SO₂—, —SO₂NH—, or —NHSO₂—, the carbonyl or sulfonyl oxygen forms a hydrogen-bond with lysine 54 in the ERK binding site. When Q is an NH-containing moiety such as —CH₂NH— or —NHNH—, the NH-group forms a hydrogen-bond with aspartic acid residue 167 in the ERK binding site. When Q is a hydrophobic group such as an alkyl chain, —O—, or —S—, Q forms additional hydrophobic interactions within the ERK binding site.

R⁴ forms hydrophobic interactions within the binding site of ERK, especially with the side-chain carbons of lysine 54 and aspartic acid 167. R⁴ may also form hydrophobic interactions with the glycine-rich loop which is made up of amino-acid residues 33–38. When R⁴ is substituted, the substituents may form further interactions within the binding site to enhance the inhibitory activity of the compound. For example, when a substituent on R⁴ is a hydrogen-bond donor or a hydrogen-bond acceptor, said substituent forms a hydrogen bond with enzyme-bound water molecules that exist in the binding site.

As used herein, linker group T, when present, connects the triazole ring with R². T may form additional interactions within the ERK binding site to further enhance the inhibitory activity of the compound. When T is a carbonyl-containing moiety such as —C(O)—, —CO₂—, —OC(O)—, —C(O)C(O)—, —C(O)NH—, —CO₂NH—, —C(O)NHNH—, —NHC(O)—, —OC(O)NH—, or —NHCO₂—, or a sulfonyl-containing moiety such as —SO₂—, —SO₂NH—, or —NHSO₂—, the carbonyl or sulfonyl oxygen forms a hydrogen-bond with the NH of glutamine 105 in the ERK binding site. When T is an NH-containing moiety such as —CH₂NH— or —NHNH—, the NH-group forms a hydrogen-bond with the carbonyl of glutamine 105. When T is a hydrophobic group such as an alkyl chain, —O— or —S—, Q forms additional hydrophobic interactions with the side-chain carbons of glutamine 105 as well as isoleucine 84.

The binding interactions described herein between the compounds of this invention and the ERK binding site have been determined by molecular modeling programs that are known to those of ordinary skill in the art. These molecular modeling programs include QUANTA [Molecular Simulations, Inc., Burlington, Mass., 1992] and SYBYL [Molecular Modeling Software, Tripos Associates, Inc., St. Louis, Mo., 1992]. As used herein, the amino acid numbering for the ERK enzyme corresponds to the Swiss-Prot database entry for accession #P28482. The Swiss-Prot database is an international protein sequence database distributed by the European Bioinformatics Institute (EBI) in Geneva, Switzerland. The database can be found at www.ebi.ac.uk/swissprot.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C— or $^{14}$C-enriched carbon are within the scope of this invention.

One embodiment of this invention relates to a compound of formula I:

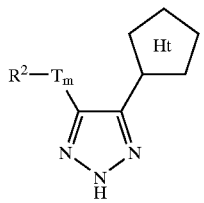

I or a pharmaceutically acceptable salt or derivative thereof, wherein Ht, $R^2$, T, and m, n, $R^3$, Q and $R^4$ are as described above, provided that when Ht is tetrazol-5-yl, and m is 0, $R^2$ is other than H or an unsubstituted phenyl; when m is 0 and $R^2$, $R^3$ and $Q_n$—$R^4$ are all H, Ht is other than [1,2,3]triazole; and when $T_m$—$R^2$ and $Q_n$—$R^4$ are both C(O)OH, Ht is other than [1,2,3]triazol-5-yl.

Another embodiment of this invention relates to compounds wherein the Ht ring is a pyrrol-3-yl (II-A), [1,2,4]triazol-3-yl (II-B), [1,2,3]triazol-4-yl (II-C and II-D), or tetrazol-5-yl (II-E) ring as shown below:

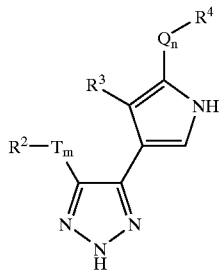

II-A

II-B

II-C

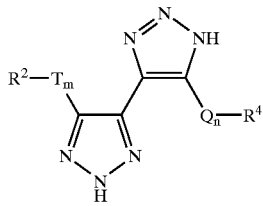

II-D

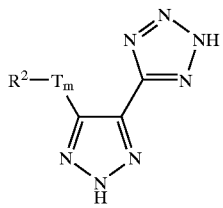

II-E or a pharmaceutically acceptable salt or derivative thereof, wherein $R^2$, T, m, n, $R^3$, Q and $R^4$ are as described above, provided that when Ht is tetrazol-5-yl, and m=0, $R^2$ is other than H or an unsubstituted phenyl; when m=0 and $R^2$, $R^3$ and Q-$R^4$ are all H, Ht is other than [1,2,3]triazole; when T-$R^2$ and Q-$R^4$ are both C(O)OH, Ht is other than [1,2,3]triazol-5-yl.

Preferred $T_m$—$R^2$ groups on II-A, II-B, II-C, II-D, and II-E are selected from hydrogen, $N(R^7)_2$, OH, 3–6 membered carbocyclyl, or an optionally substituted group selected from $C_{1-6}$ aliphatic or a 5–6 membered aryl or heteroaryl ring. When $R^2$ is an optionally substituted phenyl or aliphatic group, preferred substituents on the phenyl or aliphatic group are methyl, ethyl, halo, nitro, alkoxy, and amino. Preferred $T_mR^2$ groups are methyl, ethyl, propyl, cyclopropyl, cyclohexyl, $CH_2OCH_3$, $CH_2OH$, $NH_2$, $NHCH_3$, NHAc, $NHC(O)NHCH_3$, and $CH_2NHCH_3$. More preferred $T_mR^2$ groups of formulae II-A, II-B, II-C, II-D, and II-E are those listed in the Tables below.

When R is $R^6$, preferred $R^6$ groups are pyrrolidin-1-yl, morpholin-4-yl, piperidin-1-yl, and piperazin-1-yl, 4-methyl[1,4]diazepan-1-yl, 4-phenyl-piperazine-1-yl, wherein each group is optionally substituted as described above for heterocyclic rings. When $R^4$ is $(CH_2)_yR^6$, $(CH_2)_y$ $CH(R^6)_2$, or —$N(R^5)_2$, preferred $R^6$ groups are pyridin-3-yl, pyridin-4-yl, imidazolyl, furan-2-yl, 1,2,3,4-tetrahydroisoquinoline, tetrahydrofuran-2-yl, cyclohexyl, phenyl, benzyl, —$CH_2OH$, —$(CH_2)_2OH$, isopropyl, —$CH_2NH_2$, and —$(CH_2)_2NH_2$, wherein each group is optionally substituted. Preferred substituents on $R^6$ are —OH, pyridyl, piperidinyl, and optionally substituted phenyl, wherein phenyl is optionally substituted as described above for aryl rings. When $R^4$ is —$(CH_2)_yCH(R^8)CH(R^6)_2$, preferred $R^8$ groups are $R^7$ and $OR^7$ such as OH and $CH_2OH$. Other preferred -$QR^4$ groups are those listed in the Tables below.

Preferred compounds of formulae II-A, II-B, II-C, II-D, and II-E are those having one or more, more preferably more than one, and most preferably all, of the features selected from the group consisting of:

(a) $T_mR^2$ is hydrogen, $N(R^7)_2$, OH, 3–6 membered carbocyclyl, or an optionally substituted group selected from $C_{1-6}$ aliphatic or a 5–6 membered aryl or heteroaryl ring;

(b) Q is —CO—, —$CO_2$—, —CONH—, —$SO_2$—, —$SO_2NH$—, —OC(O)NH—, —C(O)ONH—, or —CONHNH—;

(c) $R^4$ is —$NR^5(CH_2)_yN(R^5)_2$, —$(CH_2)_yR^6$, —$(CH_2)_yCH(R$—$(CH_2)_yCH(R^8)CH(R^6)_2$;

(d) $R^5$ is R, $R^7$, or —$(CH_2)_yCH(R^6)_2$; and (e) $R^6$ is an optionally substituted group selected from phenyl, 5–6 membered heteroaryl, or 5–6 membered heterocyclyl.

More preferred compounds of formulae II-A, II-B, II-C, II-D, and II-E are those having one or more, more preferably more than one, or most preferably all, of the features selected from the group consisting of:

(a) $T_mR^2$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)NHCH_3, or $CH_2NHCH_3$;

(b) Q is —CO—, —CONH—, —$SO_2$—, or —$SO_2NH$—;

(c) $R^4$ is —$(CH_2)_yR^6$, —$(CH_2)_yCH(R^6)_2$, or —$(CH_2)_yCH(R^8)CH(R^6)_2$, wherein $R^8$ is OH or $CH_2OH$; and (d) $R^6$ is —$CH_2OH$, —$(CH_2)_2OH$, isopropyl, —$CH_2NH_2$, —$(CH_2)_2NH_2$, or an optionally substituted group selected from pyrrolidin-1-yl, morpholin-4-yl, piperidin-1-yl, piperazin-1-yl, 4-methyl[1,4]diazepan-1-yl, 4-phenyl-piperazine-1-yl, pyridin-3-yl, pyridin-4-yl, imidazolyl, furan-2-yl, 1,2,3,4-tetrahydroisoquinoline, tetrahydrofuran-2-yl, cyclohexyl, phenyl, or benzyl.

Preferred compounds of formulae II-A, II-B, and II-D are those of formulae II-A', II-B', and II-D':

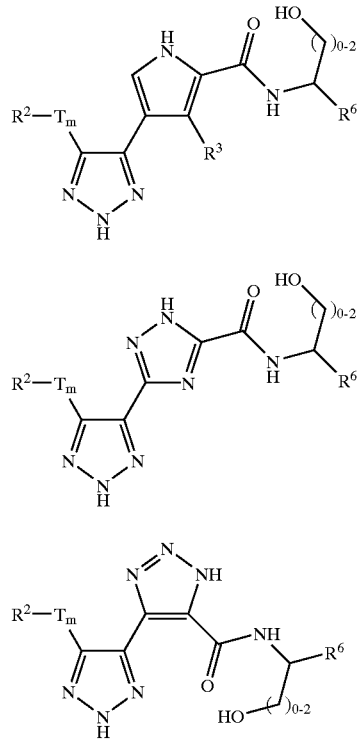

Preferred $R^6$ groups of formulae II-A', II-B', and II-D' are optionally substituted 6-membered aryl, heteroaryl, and carbocyclic rings, such as phenyl, pyridyl, and cyclohexyl.

Preferred $T_mR^2$ groups of formulae II-A', II-B', and II-D' are as described above for formulae II-A, II-B, and II-D.

Preferred compounds of formulae II-A', II-B', and II-D' are those having one, and more preferably both, of the features selected from the group consisting of:

(a) $T_mR^2$ is hydrogen, $N(R^7)_2$, OH, 3–6 membered carbocyclyl, or an optionally substituted group selected from $C_{1-6}$ aliphatic or a 5–6 membered aryl or heteroaryl ring; and (b) $R^6$ is an optionally substituted 6-membered aryl, heteroaryl, or carbocyclic ring.

More preferred compounds of formulae II-A', II-B', and II-D' are those having one, and more preferably both, of the features selected from the group consisting of:

(a) $T_mR^2$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)NHCH_3, or $CH_2NHCH_3$; and (b) $R^6$ is cyclohexyl or an optionally substituted phenyl or pyridyl ring.

Preferred compounds of formulae II-A, II-B, and II-D are further selected from those of formulae II-A°, II-B°, and II-D°:

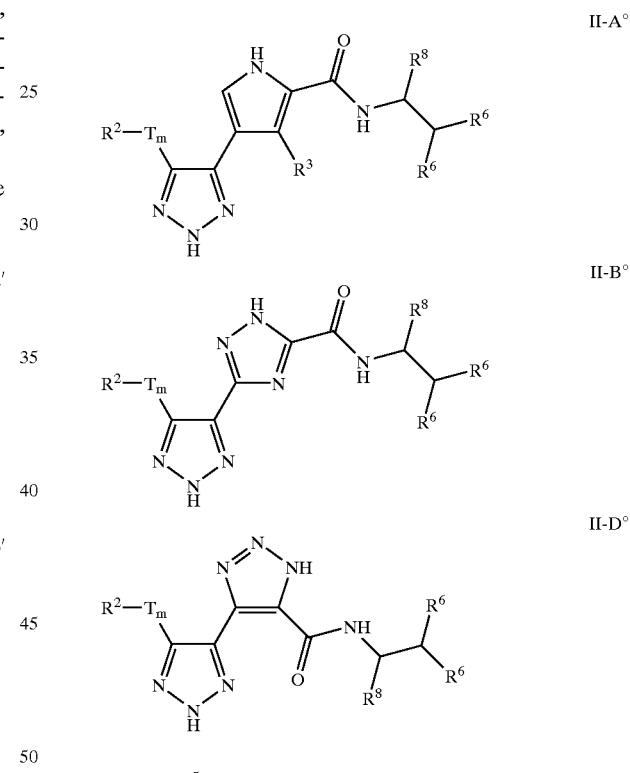

Preferred $R^5$ groups of formulae II-A°, II-B°, and II-D° are R or $OR^7$ Examples of such groups include OH, $CH_2OH$, or optionally substituted 6-membered aryl, heteroaryl, and carbocyclic rings, such as phenyl, pyridyl, and cyclohexyl.

Preferred $R^8$ groups of formulae II-A°, II-B°, and II-D° are R and $OR^7$, wherein R is an optionally substituted group selected from $C_{1-4}$ aliphatic, 3–6 membered heterocyclic, or a 5–6 membered aryl or heteroaryl ring. Examples of such groups include phenyl, methyl, ethyl, OH, and $CH_2OH$.

Preferred $T_mR^2$ groups of formulae II-A°, II-B°, and II-D°are as described above for formulae II-A, II-B, and II-D.

Preferred compounds of formulae II-A°, II-B°, and II-D° are those having one, and more preferably both, of the features selected from the group consisting of:

(a) $T_mR^2$ is hydrogen, $N(R^7)_2$, OH, 3–6 membered carbocyclyl, or an optionally substituted group selected from $C_{1-6}$ aliphatic or a 5–6 membered aryl or heteroaryl ring; and (b) $R^6$ is R or $OR^7$, and $R^8$ is $R^7$ or $OR^7$.

More preferred compounds of formulae II-A°, II-B°, and II-D° are those having one, and more preferably both, of the features selected from the group consisting of:

(a) $T_mR^2$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$; and (b) $R^6$ is OH, $CH_2OH$, phenyl, pyridyl, or cyclohexyl, and $R^8$ is methyl, ethyl, OH, or $CH_2OH$.

Exemplary structures of formulae II-A, II-B, and II-D, wherein $R^3$ is H, m is zero, and n is one are set forth in Table 1 below.

TABLE 1

Compounds II-A, II-B, and II-D

| No. | $R^2$ | Q-$R^4$ |
|---|---|---|
| II-A-1, II-B-1, and II-C-1 | phenyl | CON(Me)$_2$ |
| II-A-2, II-B-2, and II-C-2 | phenyl | CO$_2$Et |
| II-A-3, II-B-3, and II-C-3 | 3-NO$_2$-phenyl | CONHNH$_2$ |
| II-A-4, II-B-4, and II-C-4 | phenyl | CO(pyrrolidin-1-yl) |
| II-A-5, II-B-5, and II-C-5 | phenyl | CONHCH$_2$(Ph) |
| II-A-6, II-B-6, and II-C-6 | 3-NO$_2$-phenyl | CO$_2$Et |
| II-A-7, II-B-7, and II-C-7 | 4-Cl-phenyl | CO$_2$Et |
| II-A-8, II-B-8, and II-C-8 | 4-OMe-phenyl | CO$_2$Et |
| II-A-9, II-B-9, and II-C-9 | 3-NH$_2$-phenyl | CO$_2$Et |
| II-A-10, II-B-10, and II-C-10 | 3-OMe-phenyl | CO$_2$Et |
| II-A-11, II-B-11, and II-C-11 | 4-F-phenyl | CO$_2$Et |
| II-A-12, II-B-12, and II-C-12 | 4-NO$_2$-phenyl | CO$_2$Et |
| II-A-13, II-B-13, and II-C-13 | 3-Cl-phenyl | CO$_2$Et |
| II-A-14, II-B-14, and II-C-14 | 3-F-phenyl | CO$_2$Et |
| II-A-15, II-B-15, and II-C-15 | phenyl | CO$_2$H |
| II-A-16, II-B-16, and II-C-16 | 4-NH$_2$-phenyl | CO$_2$Et |
| II-A-17, II-B-17, and II-C-17 | phenyl | CONHCH$_2$CH$_2$N(Me)$_2$ |
| II-A-18, II-B-18, and II-C-18 | phenyl | CONHCH$_2$(pyridin-3-yl) |
| II-A-19, II-B-19, and II-C-19 | phenyl | CO(morpholin-4-yl) |
| II-A-20, II-B-20, and II-C-20 | phenyl | CONH(isopropyl) |
| II-A-21, II-B-21, and II-C-21 | phenyl | CO(4-Me-piperazin-1-yl) |
| II-A-22, II-B-22, and II-C-22 | phenyl | CONHCH$_2$(furan-2-yl) |
| II-A-23, II-B-23, and II-C-23 | 3-OMe-phenyl | CONMe$_2$ |
| II-A-24, II-B-24, and II-C-24 | 3-OMe-phenyl | CO(pyrrolidin-1-yl) |
| II-A-25, II-B-25, and II-C-25 | 3-OMe-phenyl | CONHCH$_2$CH$_2$N(Me)$_2$ |
| II-A-26, II-B-26, and II-C-26 | 3-OMe-phenyl | CONHCH$_2$(pyridin-3-yl) |
| II-A-27, II-B-27, and II-C-27 | 3-OMe-phenyl | CO(morpholin-4-yl) |
| II-A-28, II-B-28, and II-C-28 | 3-OMe-phenyl | CONH(isopropyl) |
| II-A-29, II-B-29, and II-C-29 | 3-OMe-phenyl | CO(4-Me-piperazin-1-yl) |
| II-A-30, II-B-30, and II-C-30 | 3-OMe-phenyl | CONHCH$_2$(furan-2-yl) |
| II-A-31, II-B-31, and II-C-31 | 4-NH$_2$-phenyl | CO$_2$Et |
| II-A-32, II-B-32, and II-C-32 | H | CONMe$_2$ |
| II-A-33, II-B-33, and II-C-33 | H | CO(pyrrolidin-1-yl) |
| II-A-34, II-B-34, and II-C-34 | 3-(AcNH)-phenyl | CO$_2$Et |
| II-A-35, II-B-35, and II-C-35 | 4-(AcNH)-phenyl | CO$_2$Et |
| II-A-36, II-B-36, and II-C-36 | 3-(AcNH)-phenyl | CO$_2$Et |
| II-A-37, II-B-37, and II-C-37 | 4-(AcNH)-phenyl | CO$_2$Et |
| II-A-38, II-B-38, and II-C-38 | 3-Cl-phenyl | CONHBn |
| II-A-39, II-B-39, and II-C-39 | 3,5-dichlorophenyl | ![structure: CONH-CH(Ph)-CH$_2$OH] |
| II-A-40, II-B-40, and II-C-40 | 3-Br-phenyl | CONH(3,4-difluorophenyl) |
| II-A-41, II-B-41, and II-C-41 | 3-Cl-phenyl | CONH(2-OH-1-Ph-ethyl) |
| II-A-42, II-B-42, and II-C-42 | 4-OH-3-I-5-nitrophenyl | CONH(2-OH-1-Ph-ethyl) |
| II-A-43, II-B-43, and II-C-43 | 3-Br-phenyl | ![structure: CONHCH$_2$-(2,3-dihydrobenzofuran-5-yl)] |
| II-A-44, II-B-44, and II-C-44 | 5-NH$_2$-4-OH-3-I-phenyl | CONH(2-OH-1-Ph-ethyl) |
| II-A-45, II-B-45, and II-C-45 | 3-Br-phenyl | CONH(2-OH-1-Ph-ethyl) |
| II-A-46, II-B-46, and II-C-46 | 3-Br-phenyl | CONHCH$_2$(3-MeO-phenyl) |
| II-A-47, II-B-47, and II-C-47 | 3-Br-phenyl | CONHCH$_2$(3-CF$_3$-phenyl) |

TABLE 1-continued

Compounds II-A, II-B, and II-D

| No. | $R^2$ | Q-$R^4$ |
|---|---|---|
| II-A-48, II-B-48, and II-C-48 | 3,5-dichlorophenyl | CONHCH$_2$(pyrid-4-yl) |
| II-A-49, II-B-49, and II-C-49 | 3-CF$_3$-phenyl | CONH(2-OH-1-Ph-ethyl) |
| II-A-50, II-B-50, and II-C-50 | 3-Cl-phenyl | CONHCH$_2$Ph |
| II-A-51, II-B-51, and II-C-51 | 3,5-dichlorophenyl | CONHOCH$_2$Ph |
| II-A-52, II-B-52, and II-C-52 | 4-OH-3-I-5-nitrophenyl | CONHCH$_2$Ph |
| II-A-53, II-B-53, and II-C-53 | 3-Cl-phenyl | CONHCH$_2$(pyrid-4-yl) |
| II-A-54, II-B-54, and II-C-54 | 3,4-dichlorophenyl | CONHOCH$_2$Ph |
| II-A-55, II-B-55, and II-C-55 | 3-Br-phenyl | CONHCH$_2$(4-SO$_2$Me-phenyl) |
| II-A-56, II-B-56, and II-C-56 | 3-Br-phenyl | CONHNH(3-CF$_3$-phenyl) |
| II-A-57, II-B-57, and II-C-57 | 3-Cl-phenyl | CONHOCH$_2$Ph |
| II-A-58, II-B-58, and II-C-58 | 3-Br-phenyl | ![structure: C(=O)NH-CH$_2$-(5-methylfuran-2-yl)] |
| II-A-59, II-B-59, and II-C-59 | 3-Br-phenyl | ![structure: C(=O)NH-CH(Ph)-CH$_2$CH$_2$OH] |
| II-A-60, II-B-60, and II-C-60 | 3-Br-phenyl | CONHCH$_2$(2-Me-phenyl) |
| II-A-61, II-B-61, and II-C-61 | 3,4-dichlorophenyl | CONHCH$_2$(pyrid-4-yl) |
| II-A-62, II-B-62, and II-C-62 | 3-Br-phenyl | CONH(1-Ph-propyl) |
| II-A-63, II-B-63, and II-C-63 | 3-F-phenyl | CONHCH$_2$Ph |
| II-A-64, II-B-64, and II-C-64 | 3,4-dichlorophenyl | ![structure: C(=O)N(Me)(Et)] |
| II-A-65, II-B-65, and II-C-65 | 3-Br-phenyl | ![structure: C(=O)NH-CH$_2$-(2-OH-cyclohexyl)] |
| II-A-66, II-B-66, and II-C-66 | 3,5-dichlorophenyl | CON(Me)(Et) |
| II-A-67, II-B-67, and II-C-67 | 3-Cl-phenyl | CONHCH$_2$(pyrid-3-yl) |
| II-A-68, II-B-68, and II-C-68 | 3-Br-phenyl | CONHCH$_2$(3,5-dimethoxyphenyl) |
| II-A-69, II-B-69, and II-C-69 | 3-Br-phenyl | CONHCH$_2$(2-OMe-phenyl) |
| II-A-70, II-B-70, and II-C-70 | 3-Cl-4-F-phenyl | CONHCH$_2$(pyrid-4-yl) |
| II-A-71, II-B-71, and II-C-71 | 3-Cl-4-F-phenyl | CON(Me)(Et) |
| II-A-72, II-B-72, and II-C-72 | 3-Br-phenyl | CONH(2-OH-1-Ph-ethyl) |
| II-A-73, II-B-73, and II-C-73 | 3-NH$_2$-phenyl | CONHCH$_2$Ph |
| II-A-74, II-B-74, and II-C-74 | 3,4-dichlorophenyl | CONHCH$_2$(pyrid-3-yl) |
| II-A-75, II-B-75, and II-C-75 | 3-Me-phenyl | CONH(2-OH-1-Ph-ethyl) |
| II-A-76, II-B-76, and II-C-76 | 3,5-dichlorophenyl | CONHCH$_2$(pyrid-3-yl) |
| II-A-77, II-B-77, and II-C-77 | 3-Cl-4-F-phenyl | CONHOCH$_2$Ph |
| II-A-78, II-B-78, and II-C-78 | 3,5-dichlorophenyl | CONHCH$_2$(tetrahydrofuran-2-yl) |
| II-A-79, II-B-79, and II-C-79 | 3-NO$_2$-phenyl | CONHCH$_2$Ph |
| II-A-80, II-B-80, and II-C-80 | 3-F-phenyl | CONHCH$_2$(pyrid-4-yl) |
| II-A-81, II-B-81, and II-C-81 | 3-Cl-2-F-phenyl | CON(Me)(Et) |
| II-A-82, II-B-82, and II-C-82 | 3-Cl-2-F-phenyl | CONHOCH$_2$Ph |

TABLE 1-continued

Compounds II-A, II-B, and II-D

| No. | R² | Q-R⁴ |
|---|---|---|
| II-A-83, II-B-83, and II-C-83 | 3-Br-phenyl | 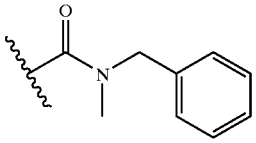 |
| II-A-84, II-B-84, and II-C-84 | 3-Cl-phenyl | CONHCH$_2$(tetrahydrofuran-2-yl) |
| II-A-85, II-B-85, and II-C-85 | 3,4-difluorophenyl | CONHOCH$_2$Ph |
| II-A-86, II-B-86, and II-C-86 | 3-Br-phenyl | CONH(3-OH-1-Ph-propyl) |
| II-A-87, II-B-87, and II-C-87 | 3-Br-phenyl | 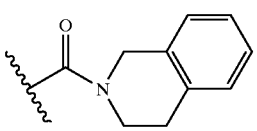 |
| II-A-88, II-B-88, and II-C-88 | 3,4-difluorophenyl | CONHCH$_2$(pyrid-4-yl) |
| II-A-89, II-B-89, and II-C-89 | 3-F-phenyl | CONHOCH$_2$Ph |
| II-A-90, II-B-90, and II-C-90 | 3-Me-phenyl | CONHCH$_2$Ph |
| II-A-91, II-B-91, and II-C-91 | 3-Br-phenyl | 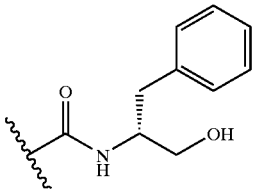 |
| II-A-92, II-B-92, and II-C-92 | 4-Cl-phenyl | CONHCH$_2$Ph |
| II-A-93, II-B-93, and II-C-93 | 3-Cl-phenyl | CON(Me)(Et) |
| II-A-94, II-B-94, and II-C-94 | 3-Br-phenyl | CONHCH$_2$(4-SO$_2$NH$_2$-phenyl) |
| II-A-95, II-B-95, and II-C-95 | 3-OH-phenyl | CONHCH$_2$Ph |
| II-A-96, II-B-96, and II-C-96 | 3-Me-phenyl | CONHCH$_2$(pyrid-4-yl) |
| II-A-97, II-B-97, and II-C-97 | Phenyl | CONHCH$_2$Ph |
| II-A-99, II-B-98, and II-C-98 | 2,5-difluorophenyl | CONHCH$_2$(pyrid-4-yl) |
| II-A-99, II-B-99, and II-C-99 | 4-Cl-phenyl | CONHOCH$_2$Ph |
| II-A-100, II-B-100, and II-C-100 | 3-Cl-4-F-phenyl | CONHCH$_2$(tetrahydrofuran-2-yl) |
| II-A-101, II-B-101, and II-C-101 | 3-Cl-4-F-phenyl | CONHCH$_2$(pyrid-3-yl) |
| II-A-102, II-B-102, and II-C-102 | 3-Br-phenyl | 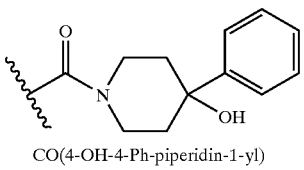
CO(4-OH-4-Ph-piperidin-1-yl) |
| II-A-103, II-B-103, and II-C-103 | 2,3-difluorophenyl | CONHOCH$_2$Ph |
| II-A-104, II-B-104, and II-C-104 | 3-Cl-phenyl | CO(morpholin-4-yl) |
| II-A-105, II-B-105, and II-C-105 | 3-Br-phenyl | 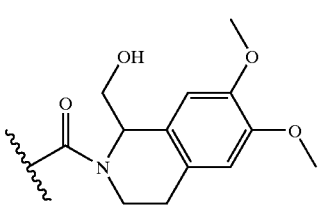 |
| II-A-106, II-B-106, and II-C-106 | 3-Cl-2-F-phenyl | CONHCH$_2$(tetrahydrofuran-2-yl) |
| II-A-107, II-B-107, and II-C-107 | 3-Cl-4-F-phenyl | CO(morpholin-4-yl) |
| II-A-108, II-B-108, and II-C-108 | 3-Cl-4-F-phenyl | CON(Me)(Et) |
| II-A-109, II-B-109, and II-C-109 | 3-Br-phenyl | CONHCH$_2$(4-NH$_2$-phenyl) |

TABLE 1-continued

Compounds II-A, II-B, and II-D

| No. | R² | Q-R⁴ |
|---|---|---|
| II-A-110, II-B-110, and II-C-110 | 3-Br-phenyl | 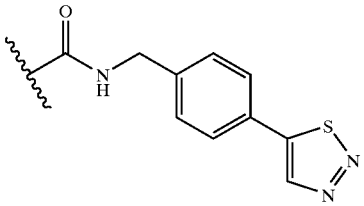 |
| II-A-111, II-B-111, and II-C-111 | 4-F-phenyl | CONHCH₂Ph |
| II-A-112, II-B-112, and II-C-112 | 3,5-dichlorophenyl | CO(morpholin-4-yl) |
| II-A-113, II-B-113, and II-C-113 | 2,5-difluorophenyl | CONHOCH₂Ph |
| II-A-114, II-B-114, and II-C-114 | 3-Cl-2-F-phenyl | CONHCH₂(pyrid-3-yl) |
| II-A-115, II-B-115, and II-C-115 | 3-Cl-2-F-phenyl | CONHCH₂(pyrid-4-yl) |
| II-A-116, II-B-116, and II-C-116 | 3,4-difluorophenyl | CONHCH₂(pyrid-3-yl) |
| II-A-117, II-B-117, and II-C-117 | 4-OMe-phenyl | CONHCH₂Ph |
| II-A-118, II-B-118, and II-C-118 | 3-Br-phenyl | CONHCH₂(2,4,6-trimethoxyphenyl) |
| II-A-119, II-B-119, and II-C-119 | 3-F-phenyl | CONHCH₂(pyrid-3-yl) |
| II-A-120, II-B-120, and II-C-120 | 3,4-difluorophenyl | CONHCH₂(tetrahydrofuran-2-yl) |
| II-A-121, II-B-121, and II-C-121 | 3-Cl-2-F-phenyl | 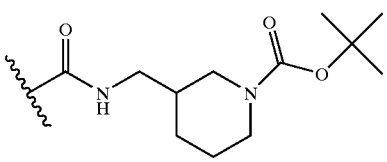 |
| II-A-122, II-B-122, and II-C-122 | 3-Br-phenyl | 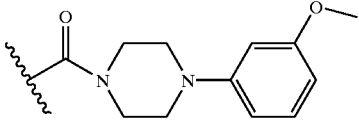 |
| II-A-123, II-B-123, and II-C-123 | 3-Br-phenyl | 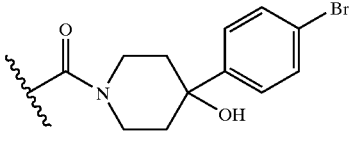 |
| II-A-124, II-B-124, and II-C-124 | 3-Br-phenyl | CONHCH₂(2,5-dimethoxyphenyl) |
| II-A-125, II-B-125, and II-C-125 | 3,5-dichlorophenyl | 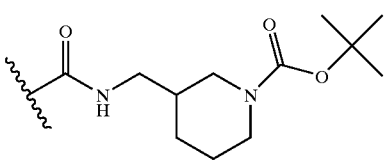 |
| II-A-126, II-B-126, and II-C-126 | 3-Br-phenyl | 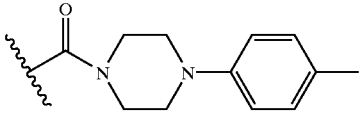 |
| II-A-127, II-B-127, and II-C-127 | 3,4-dichlorophenyl | CO(morpholin-4-yl) |
| II-A-128, II-B-128, and II-C-128 | 3-Br-phenyl | 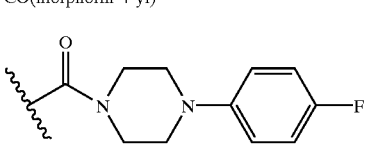 |
| II-A-129, II-B-129, and II-C-129 | 3-Cl-2-F-phenyl | CO(morpholin-4-yl) |
| II-A-130, II-B-130, and II-C-130 | 3-Br-phenyl | CONHCH₂CH₂OH |
| II-A-131, II-B-131, and II-C-131 | 3-NH₂-phenyl | CONHCH₂Ph |
| II-A-132, II-B-132, and II-C-132 | 3-MeOC(O)-phenyl | CONHCH₂Ph |
| II-A-133, II-B-133, and II-C-133 | 4-MeO-phenyl | CONHOCH₂Ph |

TABLE 1-continued

Compounds II-A, II-B, and II-D

| No. | R² | Q-R⁴ |
|---|---|---|
| II-A-134, II-B-134, and II-C-134 | Phenyl | CO(pyrrolidin-1-yl) |
| II-A-135, II-B-135, and II-C-135 | 3-MeO-phenyl | CO(morpholin-4-yl) |
| II-A-136, II-B-136, and II-C-136 | 3-Cl-phenyl | CO(4-Me-piperidin-1-yl) |
| II-A-137, II-B-137, and II-C-137 | 3-NO₂-phenyl | CONH₂NH₂ |
| II-A-138, II-B-138, and II-C-138 | 3-Br-phenyl | ![structure: acyl-piperazine-pyrazine] |
| II-A-139, II-B-139, and II-C-139 | 3-Br-phenyl | ![structure: N-benzyl-N-(hydroxypropyl)amide] |
| II-A-140, II-B-140, and II-C-140 | 3-Cl-phenyl | CONHPh |
| II-A-141, II-B-141, and II-C-141 | 2,3-difluorophenyl | CONHCH₂(pyrid-4-yl) |
| II-A-142, II-B-142, and II-C-142 | 3-Cl-phenyl | ![structure: histamine amide] |
| II-A-143, II-B-143, and II-C-143 | Phenyl | CON(Me)₂ |
| II-A-144, II-B-144, and II-C-144 | 3-OMe-phenyl | CO(pyrrolidin-1-yl) |
| II-A-145, II-B-145, and II-C-145 | 3-OMe-phenyl | CONHCH₂(pyrid-3-yl) |
| II-A-146, II-B-146, and II-C-146 | 4-F-phenyl | CONHOCH₂Ph |
| II-A-147, II-B-147, and II-C-147 | 3-OMe-phenyl | CONHCH₂(furan-2-yl) |
| II-A-148, II-B-148, and II-C-148 | 3-NO₂-phenyl | COOEt |
| II-A-149, II-B-149, and II-C-149 | Phenyl | CONHCH₂(furan-2-yl) |
| II-A-150, II-B-150, and II-C-150 | Phenyl | CO(morpholin-4-yl) |
| II-A-151, II-B-151, and II-C-151 | 3-Cl-phenyl | COOEt |
| II-A-152, II-B-152, and II-C-152 | 3-Br-phenyl | CONHMe |
| II-A-153, II-B-153, and II-C-153 | Phenyl | CONHCH₂(pyrid-3-yl) |
| II-A-154, II-B-154, and II-C-154 | 3-OMe-phenyl | CON(Me)₂ |
| II-A-155, II-B-155, and II-C-155 | 3-Cl-phenyl | ![structure: N-(2-hydroxyindanyl)amide] |
| II-A-156, II-B-156, and II-C-156 | 3-Br-phenyl | ![structure: N-(pyridin-4-ylmethyl)-N-(hydroxypropyl)amide] |
| II-A-157, II-B-157, and II-C-157 | 3-Br-phenyl | COOEt |
| II-A-158, II-B-158, and II-C-158 | phenyl | CONH(iPr) |
| II-A-159, II-B-159, and II-C-159 | 3-OMe-phenyl | CONH(iPr) |
| II-A-160, II-B-160, and II-C-160 | 3-COOH-phenyl | CONH(iPr) |
| II-A-161, II-B-161, and II-C-161 | 3-Br-phenyl | CONHO(iPr) |
| II-A-162, II-B-162, and II-C-162 | 3-F-phenyl | COOEt |

TABLE 1-continued

Compounds II-A, II-B, and II-D

| No. | R$^2$ | Q-R$^4$ |
|---|---|---|
| II-A-163, II-B-163, and II-C-163 | 3-OMe-phenyl | CO(4-Me-piperidin-1-yl) |
| II-A-164, II-B-164, and II-C-164 | 4-NH$_2$-phenyl | COOEt |
| II-A-165, II-B-165, and II-C-165 | 4-NO$_2$-phenyl | COOEt |
| II-A-166, II-B-166, and II-C-166 | phenyl | CO(4-Me-piperidin-1-yl) |
| II-A-167, II-B-167, and II-C-167 | 4-Cl-phenyl | COOEt |
| II-A-168, II-B-168, and II-C-168 | 4-OMe-phenyl | COOEt |
| II-A-169, II-B-169, and II-C-169 | phenyl | COOEt |
| II-A-170, II-B-170, and II-C-170 | 3-OMe-phenyl | COOEt |
| II-A-171, II-B-171, and II-C-171 | 4-F-phenyl | COOEt |
| II-A-172, II-B-172, and II-C-172 | 3-NH$_2$-phenyl | COOEt |
| II-A-173, II-B-173, and II-C-173 | 3-Cl-phenyl | COOH |
| II-A-174, II-B-174, and II-C-174 | 3-Cl-phenyl | ![structure: N-acyl phenylalanine methyl ester] |
| II-A-175, II-B-175, and II-C-175 | 3-Cl-phenyl | ![structure: N-acyl phenylglycine tert-butyl ester] |
| II-A-176, II-B-176, and II-C-176 | 3-OMe-phenyl | CONHCH$_2$(pyrid-4-yl) |
| II-A-177, II-B-177, and II-C-177 | 3,5-dimethoxyphenyl | CONHCH$_2$(pyrid-4-yl) |
| II-A-178, II-B-178, and II-C-178 | 4-F-phenyl | CONHCH$_2$(pyrid-3-yl) |
| II-A-179, II-B-179, and II-C-179 | 4-OMe-phenyl | CONHCH$_2$(pyrid-3-yl) |
| II-A-180, II-B-180, and II-C-180 | 2,5-dimethoxyphenyl | CONHCH$_2$(pyrid-3-yl) |
| II-A-181, II-B-181, and II-C-181 | 2,5-difluorophenyl | CONHCH$_2$(pyrid-3-yl) |
| II-A-182, II-B-182, and II-C-182 | 4-F-phenyl | CONHCH$_2$(tetrahydrofuran-2-yl) |
| II-A-183, II-B-183, and II-C-183 | 4-OMe-phenyl | CONHCH$_2$(tetrahydrofuran-2-yl) |
| II-A-184, II-B-184, and II-C-184 | 3-F-phenyl | CONHCH$_2$(tetrahydrofuran-2-yl) |
| II-A-185, II-B-185, and II-C-185 | 3-OMe-phenyl | CONHCH$_2$(tetrahydrofuran-2-yl) |
| II-A-186, II-B-186, and II-C-186 | 2,5-dimethoxyphenyl | CONHCH$_2$(tetrahydrofuran-2-yl) |
| II-A-187, II-B-187, and II-C-187 | 2,3-difluorophenyl | CONHCH$_2$(tetrahydrofuran-2-yl) |
| II-A-188, II-B-188, and II-C-188 | 2,5-difluorophenyl | CONHCH$_2$(tetrahydrofuran-2-yl) |
| II-A-189, II-B-189, and II-C-189 | 4-F-phenyl | CONHCH$_2$(1-Et-pyrrolidin-2-yl) |
| II-A-190, II-B-190, and II-C-190 | 4-OMe-phenyl | CONHCH$_2$(1-Et-pyrrolidin-2-yl) |
| II-A-191, II-B-191, and II-C-191 | 3-F-phenyl | CONHCH$_2$(1-Et-pyrrolidin-2-yl) |
| II-A-192, II-B-192, and II-C-192 | 3-OMe-phenyl | CONHCH$_2$(1-Et-pyrrolidin-2-yl) |
| II-A-193, II-B-193, and II-C-193 | 2,5-dimethoxyphenyl | CONHCH$_2$(1-Et-pyrrolidin-2-yl) |
| II-A-194, II-B-194, and II-C-194 | 3,4-difluorophenyl | CONHCH$_2$(1-Et-pyrrolidin-2-yl) |
| II-A-195, II-B-195, and II-C-195 | 2,3-difluorophenyl | CONHCH$_2$(1-Et-pyrrolidin-2-yl) |
| II-A-196, II-B-196, and II-C-196 | 2,5-difluorophenyl | CONHCH$_2$(1-Et-pyrrolidin-2-yl) |
| II-A-197, II-B-197, and II-C-197 | 4-F-phenyl | CO(morpholin-4-yl) |
| II-A-198, II-B-198, and II-C-198 | 4-OMe-phenyl | CO(morpholin-4-yl) |
| II-A-199, II-B-199, and II-C-199 | 3-F-phenyl | CO(morpholin-4-yl) |
| II-A-200, II-B-200, and II-C-200 | 2,5-dimethoxyphenyl | CO(morpholin-4-yl) |
| II-A-201, II-B-201, and II-C-201 | 3,4-difluorophenyl | CO(morpholin-4-yl) |
| II-A-202, II-B-202, and II-C-202 | 2,3-difluorophenyl | CO(morpholin-4-yl) |
| II-A-203, II-B-203, and II-C-203 | 2,5-difluorophenyl | CO(morpholin-4-yl) |
| II-A-204, II-B-204, and II-C-204 | 4-F-phenyl | CO(4-Me-piperidin-1-yl) |
| II-A-205, II-B-205, and II-C-205 | 4-OMe-phenyl | CO(4-Me-piperidin-1-yl) |
| II-A-206, II-B-206, and II-C-206 | 3-F-phenyl | CO(4-Me-piperidin-1-yl) |
| II-A-207, II-B-207, and II-C-207 | 2,5-dimethoxyphenyl | CO(4-Me-piperidin-1-yl) |
| II-A-208, II-B-208, and II-C-208 | 3,4-difluorophenyl | CO(4-Me-piperidin-1-yl) |
| II-A-209, II-B-209, and II-C-209 | 2,3-difluorophenyl | CO(4-Me-piperidin-1-yl) |
| II-A-210, II-B-210, and II-C-210 | 2,5-difluorophenyl | CO(4-Me-piperidin-1-yl) |
| II-A-211, II-B-211, and II-C-211 | 4-Cl-phenyl | CONHCH$_2$(pyrid-4-yl) |
| II-A-212, II-B-212, and II-C-212 | 3,4-dimethoxyphenyl | CONHCH$_2$(pyrid-4-yl) |
| II-A-213, II-B-213, and II-C-213 | benzo[1,3]dioxo-5-yl | CONHCH$_2$(pyrid-4-yl) |
| II-A-214, II-B-214, and II-C-214 | 4-Cl-phenyl | CONHCH$_2$(pyrid-3-yl) |
| II-A-215, II-B-215, and II-C-215 | 3,4-dimethoxyphenyl | CONHCH$_2$(pyrid-3-yl) |
| II-A-216, II-B-216, and II-C-216 | benzo[1,3]dioxo-5-yl | CONHCH$_2$(pyrid-3-yl) |

TABLE 1-continued

Compounds II-A, II-B, and II-D

| No. | R² | Q-R⁴ |
|---|---|---|
| II-A-217, II-B-217, and II-C-217 | 4-Cl-phenyl | CONHCH$_2$(tetrahydrofuran-2-yl) |
| II-A-218, II-B-218, and II-C-218 | 3,4-dimethoxyphenyl | CONHCH$_2$(tetrahydrofuran-2-yl) |
| II-A-219, II-B-219, and II-C-219 | benzo[1,3]dioxo-5-yl | CONHCH$_2$(tetrahydrofuran-2-yl) |
| II-A-220, II-B-220, and II-C-220 | 4-Cl-phenyl | CONHCH$_2$(1-Et-pyrrolidin-2-yl) |
| II-A-221, II-B-221, and II-C_221 | 3,4-dichlorophenyl | CONHCH$_2$(1-Et-pyrrolidin-2-yl) |
| II-A-222, II-B-222, and II-C-222 | 3-Cl-2-F-phenyl | CONHCH$_2$(1-Et-pyrrolidin-2-yl) |
| II-A-223, II-B-223, and II-C-223 | 3-Cl-4-F-phenyl | CONHCH$_2$(1-Et-pyrrolidin-2-yl) |
| II-A-224, II-B-224, and II-C-224 | 3,4-dimethoxyphenyl | CONHCH$_2$(1-Et-pyrrolidin-2-yl) |
| II-A-225, II-B-225, and II-C-225 | benzo[1,3]dioxo-5-yl | CONHCH$_2$(1-Et-pyrrolidin-2-yl) |
| II-A-226, II-B-226, and II-C-226 | 3,5-dichlorophenyl | CONHCH$_2$(1-Et-pyrrolidin-2-yl) |
| II-A-227, II-B-227, and II-C-227 | 4-Cl-phenyl | CO(morpholin-4-yl) |
| II-A-228, II-B-228, and II-C-228 | 3,4-dimethoxyphenyl | CO(morpholin4-yl) |
| II-A-229, II-B-229, and II-C-229 | benzo[1,3]dioxo-5-yl | CO(morpholin-4-yl) |
| II-A-230, II-B-230, and II-C-230 | 4-Cl-phenyl | CO(4-Me-piperidin-1-yl) |
| II-A-231, II-B-231, and II-C-231 | 3,4-dichlorophenyl | CO(4-Me-piperidin-1-yl) |
| II-A-232, II-B-232, and II-C-232 | 3-Cl-2-F-phenyl | CO(4-Me-piperidin-1-yl) |
| II-A-233, II-B-233, and II-C-233 | 3-Cl-4-F-phenyl | CO(4-Me-piperidin-1-yl) |
| II-A-234, II-B-234, and II-C-234 | 3,4-dimethoxyphenyl | CO(4-Me-piperidin-1-yl) |
| II-A-235, II-B-235, and II-C-235 | benzo[1,3]dioxo-5-yl | CO(4-Me-piperidin-1-yl) |
| II-A-236, II-B-236, and II-C-236 | 3,5-dichlorophenyl | CO(4-Me-piperidin-1-yl) |
| II-A-237, II-B-237, and II-C-237 | 2,3-difluorophenyl | CON(Me)(Et) |
| II-A-238, II-B-238, and II-C-238 | 4-F-phenyl | ![structure: acyl-NH-CH2-(piperidin-3-yl)-N-Boc] |
| II-A-239, II-B-239, and II-C-239 | 3-OMe-phenyl | ![structure: acyl-NH-CH2-(piperidin-3-yl)-N-Boc] |
| II-A-240, II-B-240, and II-C-240 | 2,5-dimethoxyphenyl | ![structure: acyl-NH-CH2-(piperidin-3-yl)-N-Boc] |
| II-A-241, II-B-241, and II-C-241 | 3,4-difluorophenyl | ![structure: acyl-NH-CH2-(piperidin-3-yl)-N-Boc] |
| II-A-242, II-B-242, and II-C-242 | 2,3-difluorophenyl | ![structure: acyl-NH-CH2-(piperidin-3-yl)-N-Boc] |
| II-A-243, II-B-243, and II-C-243 | 2,5-difluorophenyl | ![structure: acyl-NH-CH2-(piperidin-3-yl)-N-Boc] |
| II-A-244, II-B-244, and II-C-244 | 3-MeO-phenyl | CONHOCH$_2$Ph |
| II-A-245, II-B-245, and II-C-245 | 2,5-dimethoxyphenyl | CONHOCH$_2$Ph |

TABLE 1-continued

Compounds II-A, II-B, and II-D

| No. | R² | Q-R⁴ |
| --- | --- | --- |
| II-A-246, II-B-246, and II-C-246 | 3-F-phenyl | *[structure: -C(O)NH-CH₂CH₂-(1H-imidazol-4-yl)]* |
| II-A-247, II-B-247, and II-C-247 | 3-MeO-phenyl | *[structure: -C(O)NH-CH₂CH₂-(1H-imidazol-4-yl)]* |
| II-A-248, II-B-248, and II-C-248 | 3,4-difluorophenyl | *[structure: -C(O)NH-CH₂CH₂-(1H-imidazol-4-yl)]* |
| II-A-249, II-B-249, and II-C-249 | 2,3-difluorophenyl | *[structure: -C(O)NH-CH₂CH₂-(1H-imidazol-4-yl)]* |
| II-A-250, II-B-250, and II-C-250 | 3-Cl-phenyl | *[structure: -C(O)NH-CH₂-(1-Boc-piperidin-3-yl)]* |
| II-A-251, II-B-251, and II-C-251 | 4-Cl-phenyl | *[structure: -C(O)NH-CH₂-(1-Boc-piperidin-3-yl)]* |
| II-A-252, II-B-252, and II-C-252 | 4-Cl-phenyl | *[structure: -C(O)NH-CH₂CH₂-(1H-imidazol-4-yl)]* |
| II-A-253, II-B-253, and II-C-253 | 3,4-dichlorophenyl | *[structure: -C(O)NH-CH₂-(1-Boc-piperidin-3-yl)]* |
| II-A-254, II-B-254, and II-C-254 | 3,4-dichlorophenyl | *[structure: -C(O)NH-CH₂CH₂-(1H-imidazol-4-yl)]* |
| II-A-255, II-B-255, and II-C-255 | 3-Cl-2-F-phenyl | *[structure: -C(O)NH-CH₂CH₂-(1H-imidazol-4-yl)]* |

TABLE 1-continued

Compounds II-A, II-B, and II-D

| No. | R² | Q-R⁴ |
|---|---|---|
| II-A-256, II-B-256, and II-C-256 | 3-Cl-4-F-phenyl | 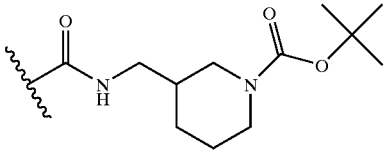 |
| II-A-257, II-B-257, and II-C-257 | 3-Cl-4-F-phenyl | 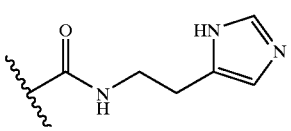 |
| II-A-258, II-B-258, and II-C-258 | 3,4-dimethoxyphenyl | CON(Me)(Et) |
| II-A-259, II-B-259, and II-C-259 | 3,4-dimethoxyphenyl | 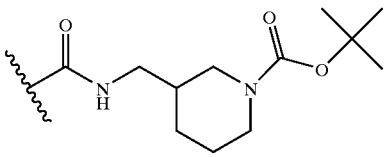 |
| II-A-260, II-B-260, and II-C-260 | 3,4-dimethoxyphenyl | CONHOCH₂Ph |
| II-A-261, II-B-261, and II-C-261 | 3,4-dimethoxyphenyl | 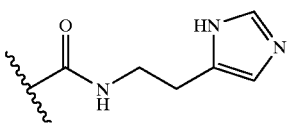 |
| II-A-262, II-B-262, and II-C-262 | benzo[1,3]dioxo-5-yl | CON(Me)(Et) |
| II-A-263, II-B-263, and II-C-263 | benzo[1,3]dioxo-5-yl | 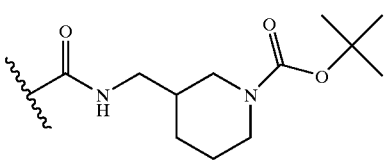 |
| II-A-264, II-B-264, and II-C-264 | benzo[1,3]dioxo-5-yl | CONHOCH₂Ph |
| II-A-265, II-B-265, and II-C-265 | benzo[1,3]dioxo-5-yl | 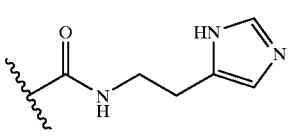 |
| II-A-266, II-B-266, and II-C-266 | 3,5-dichlorophenyl | 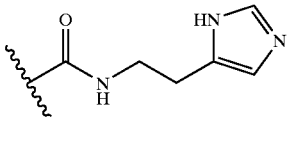 |
| II-A-267, II-B-267, and II-C-267 | 3-Br-phenyl | 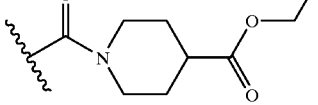 |

TABLE 1-continued
Compounds II-A, II-B, and II-D
| No. | R² | Q-R⁴ |
|---|---|---|
| II-A-268, II-B-268, and II-C-268 | 3-Br-phenyl | 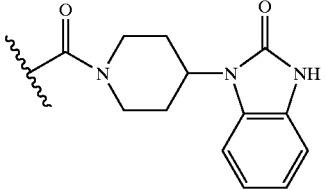 |
| II-A-269, II-B-269, and II-C-269 | 3-Br-phenyl | 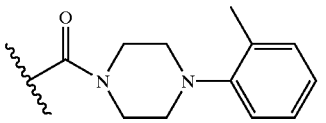 |
| II-A-270, II-B-270, and II-C-270 | 3-Br-phenyl | 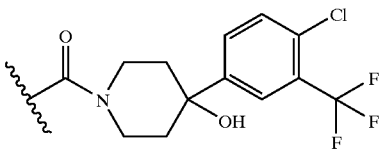 |
| II-A-271, II-B-271, and II-C-271 | 3-Br-phenyl | 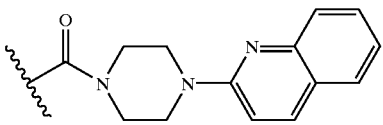 |
| II-A-272, II-B-272, and II-C-272 | 3-Br-phenyl | 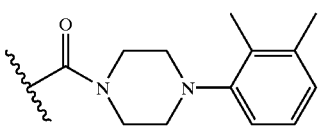 |
| II-A-273, II-B-273, and II-C-273 | 3-Br-phenyl | 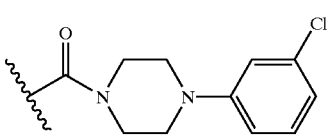 |
| II-A-274, II-B-274, and II-C-274 | 3-Br-phenyl | 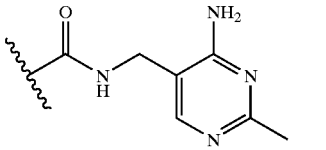 |
| II-A-275, II-B-275, and II-C-275 | 3-Br-phenyl | 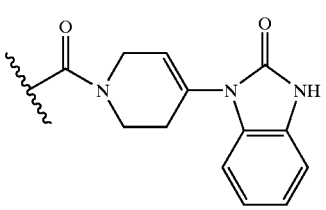 |
| II-A-276, II-B-276, and II-C-276 | 3-Br-phenyl | 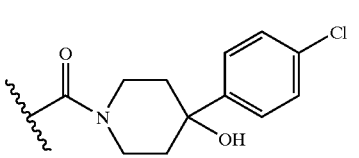 |

TABLE 1-continued

Compounds II-A, II-B, and II-D

| No. | R² | Q-R⁴ |
|---|---|---|
| II-A-277, II-B-277, and II-C-277 | 3-Br-phenyl | [piperidine-N-acyl with 4-(1H-benzotriazol-1-yl) substituent] |
| II-A-278, II-B-278, and II-C-278 | 3-Br-phenyl | [piperazine-N-acyl with 4-(3-phenyl-1,2,4-thiadiazol-5-yl) substituent] |
| II-A-279, II-B-279, and II-C-279 | 3-Br-phenyl | [6-methoxy-1,2,3,4-tetrahydro-β-carboline-2-acyl] |
| II-A-280, II-B-280, and II-C-280 | 3-Br-phenyl | CONH(CH₂)₂COOH |
| II-A-281, II-B-281, and II-C-281 | 3-Br-phenyl | [piperidine-N-acyl with 4-OH and 4-(3-trifluoromethylphenyl) substituents] |
| II-A-282, II-B-282, and II-C-282 | 3-Br-phenyl | CONHCH₂(4-COOH-phenyl) |
| II-A-283, II-B-283, and II-C-283 | 3-Br-phenyl | [CONHCH₂-(3-hydroxy-2-methyl-5-hydroxymethylpyridin-4-yl)] |
| II-A-284, II-B-284, and II-C-284 | 3-Br-phenyl | [1,4-diazepane-N-acyl with 4-(4-trifluoromethylpyrimidin-2-yl) substituent] |
| II-A-285, II-B-285, and II-C-285 | 3-NO₂-phenyl | CONHCH₂phenyl |
| II-A-286, II-B-286, and II-C-286 | 3-Cl-phenyl | CONHCH₂(1-Et-pyrrolidin-2-yl) |
| II-A-287, II-B-287, and II-C-287 | 3-(N—Et—NHCO)-phenyl | CONHCH₂phenyl |

TABLE 1-continued

Compounds II-A, II-B, and II-D

| No. | R² | Q-R⁴ |
|---|---|---|
| II-A-288, II-B-288, and II-C-288 | 3-Br-phenyl | [structure: N-benzyl-N-(1-hydroxy-3-phenylpropan-2-yl)amide — phenyl-CH(CH₂OH)-N(CH₂Ph)-C(=O)-] |
| II-A-289, II-B-289, and II-C-289 | 3-NO₂-phenyl | CONHCH₂(pyrid-4-yl) |
| II-A-290, II-B-290, and II-C-290 | 3-Br-phenyl | [structure: amide of 1-(2,3-dihydro-1,4-benzodioxin-6-yl)-2-phenoxyethylamine] |
| II-A-291, II-B-291, and II-C-291 | 3-F-phenyl | CON(Me)(Et) |
| II-A-292, II-B-292, and II-C-292 | 3-MeO-phenyl | CON(Me)(Et) |
| II-A-293, II-B-293, and II-C-293 | 3-Br-phenyl | [structure: tyrosinol amide] |
| II-A-294, II-B-294, and II-C-294 | 3-Br-phenyl | [structure: histidinol amide] |
| II-A-295, II-B-295, and II-C-295 | 3-Br-phenyl | [structure: tris(hydroxymethyl)methyl amide] |
| II-A-296, II-B-296, and II-C-296 | 3-Br-phenyl | [structure: 3,4-dimethoxyphenyl-substituted amino alcohol amide] |

TABLE 1-continued
Compounds II-A, II-B, and II-D
| No. | R² | Q-R⁴ |
|---|---|---|
| II-A-297, II-B-297, and II-C-297 | phenyl | CONH(CH₂)₂NMe₂ |
| II-A-298, II-B-298, and II-C-298 | 3-MeO-phenyl | CONH(CH₂)₂NMe₂ |
| II-A-299, II-B-299, and II-C-299 | 3-Br-phenyl | CONHCH₂phenyl |
| II-A-300, II-B-300, and II-C-300 | 3-Cl-phenyl | 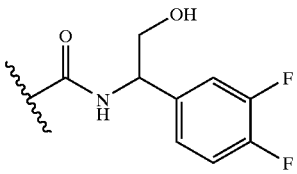 |
| II-A-301, II-B-301, and II-C-301 | 3-Cl-phenyl | 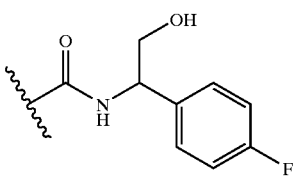 |
| II-A-302, II-B-302, and II-C-302 | 3-Cl-phenyl | 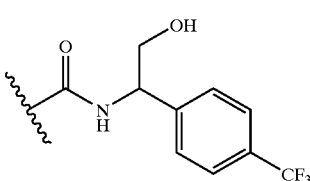 |
| II-A-303, II-B-303, and II-C-303 | 3-Cl-phenyl | 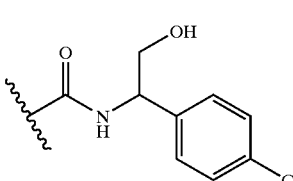 |
| II-A-304, II-B-304, and II-C-304 | 3-Cl-phenyl | 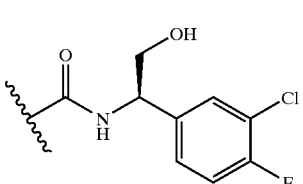 |
| II-A-305, II-B-305, and II-C-305 | 3-Cl-phenyl | 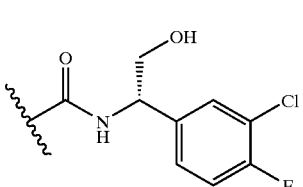 |
| II-A-306, II-B-306, and II-C-306 | 3-Cl-phenyl | 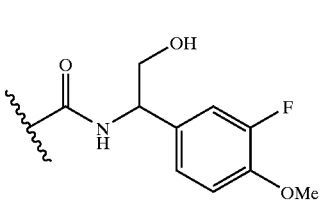 |

TABLE 1-continued

Compounds II-A, II-B, and II-D

| No. | R² | Q-R⁴ |
|---|---|---|
| II-A-307, II-B-307, and II-C-307 | 3-Cl-phenyl | *(structure: N-H amide linked to (S)-1-phenyl-2-acetoxyethyl group)* |
| II-A-308, II-B-308, and II-C-308 | 3-Cl-phenyl | *(structure: N-H amide linked to (S)-1-phenyl-2-(methoxycarbonyloxy)ethyl group)* |
| II-A-309, II-B-309, and II-C-309 | 3-Cl-phenyl | *(structure: N-H amide linked to 1-(3-methoxy-4-fluorophenyl)-2-hydroxyethyl group)* |
| II-A-310, II-B-310, and II-C-310 | 3,5-dichlorophenyl | *(structure: N-H amide linked to (S)-1-(3-chloro-4-fluorophenyl)-2-hydroxyethyl group)* |
| II-A-311, II-B-311, and II-C-311 | 3-Br-5-CF₃-phenyl | *(structure: N-H amide linked to (S)-1-phenyl-2-hydroxyethyl group)* |
| II-A-312, II-B-312, and II-C-312 | 3-Cl-phenyl | *(structure: N-H amide linked to 1-(3,5-dichlorophenyl)-2-hydroxyethyl group)* |
| II-A-313, II-B-313, and II-C-313 | 3,5-dichlorophenyl | *(structure: N-H amide linked to 1-(3-chloro-4-fluorophenyl)-2-hydroxyethyl group)* |

TABLE 1-continued

Compounds II-A, II-B, and II-D

| No. | R² | Q-R⁴ |
|---|---|---|
| II-A-314, II-B-314, and II-C-314 | 3-Cl-4-CN-phenyl | phenyl-CH(CH₂OH)-NH-C(O)- |
| II-A-v15, II-B-315, and II-C-315 | 3-Cl-4-CH₂OH-phenyl | phenyl-CH(CH₂OH)-NH-C(O)- |
| II-A-316, II-B-316, and II-C-316 | 3-Cl-4-CH₂NH₂-phenyl | phenyl-CH(CH₂OH)-NH-C(O)- |
| II-A-317, II-B-317, and II-C-317 | 4-(CH₃C(O)NHCH₂)-3-Cl-phenyl | phenyl-CH(CH₂OH)-NH-C(O)- |
| II-A-318, II-B-318, and II-C-318 | 4-(morpholinomethyl)-3-Cl-phenyl | phenyl-CH(CH₂OH)-NH-C(O)- |
| II-A-319, II-B-319, and II-C-319 | 4-(CH₃NHC(O)NHCH₂)-3-Cl-phenyl | phenyl-CH(CH₂OH)-NH-C(O)- |
| II-A-320, II-B-320, and II-C-320 | 4-(CH₃OC(O)NHCH₂)-3-Cl-phenyl | phenyl-CH(CH₂OH)-NH-C(O)- |

TABLE 1-continued

Compounds II-A, II-B, and II-D

| No. | R² | Q-R⁴ |
|---|---|---|
| II-A-321, II-B-321, and II-C-321 | [ethylsulfonamido-methyl-2-chlorophenyl structure] | [C(O)NH-CH(Ph)-CH₂OH structure] |
| II-A-322, II-B-322, and II-C-322 | [MeOCH₂-2-chlorophenyl structure] | [C(O)NH-CH(Ph)-CH₂OH structure] |
| II-A-323, II-B-323, and II-C-323 | CH₂Ph | CON(Me)₂ |
| II-A-324, II-B-324, and II-C-324 | cyclopentylmethyl | CO₂NHCH₂Ph |
| II-A-325, II-B-325, and II-C-325 | isopropyl | CN |
| II-A-326, II-B-326, and II-C-326 | 3-Cl-phenyl | NHCOCH₂Ph |
| II-A-327, II-B-327, and II-C-327 | 3-Cl-phenyl | NHSO₂-morpholin-4-yl |
| II-A-328, II-B-328, and II-C-328 | 3-Cl-phenyl | NHCONHCH₂Ph |
| II-A-329, II-B-329, and II-C-329 | 3-Cl-phenyl | NHCO₂-tetrahydrofuran-2-yl |
| II-A-330, II-B-330, and II-C-330 | CH₂Ph | CONHCH₂Ph |
| II-A-331, II-B-331, and II-C-331 | Me | CONHCH₂Ph |
| II-A-332, II-B-332, and II-C-332 | isopropyl | CONHCH₂PH |
| II-A-333, II-B-333, and II-C-333 | H | CON(Me)₂ |
| II-A-334, II-B-334, and II-C-334 | [N-acetyl-serinyl-amido-methyl-2-chlorophenyl structure] | [C(O)NH-CH(3-Cl-4-F-phenyl)-CH₂OH structure] |
| II-A-335, II-B-335, and II-C-335 | [N-acetyl-(S)-alanyl-amido-methyl-2-chlorophenyl structure] | [C(O)NH-CH(3-Cl-4-F-phenyl)-CH₂OH structure] |
| II-A-336, II-B-336, and II-C-336 | [N-acetyl-(R)-alanyl-amido-methyl-2-chlorophenyl structure] | [C(O)NH-CH(3-Cl-4-F-phenyl)-CH₂OH structure] |

TABLE 1-continued
Compounds II-A, II-B, and II-D
| No. | R² | Q-R⁴ |
|---|---|---|
| II-A-337, II-B-337, and II-C-337 | 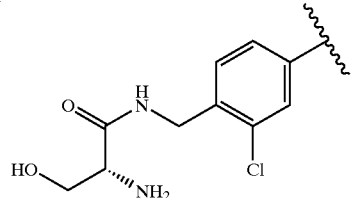 | 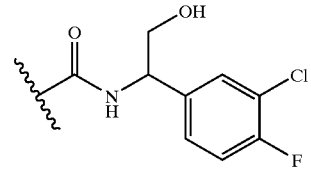 |
| II-A-338, II-B-338, and II-C-338 | 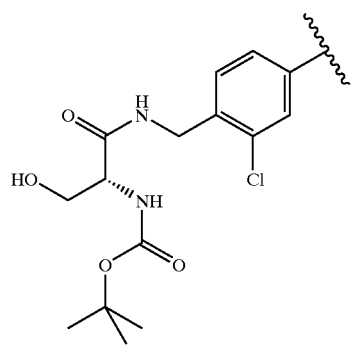 | 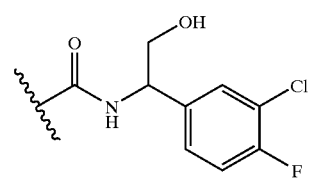 |
| II-A-339, II-B-339, and II-C-339 | 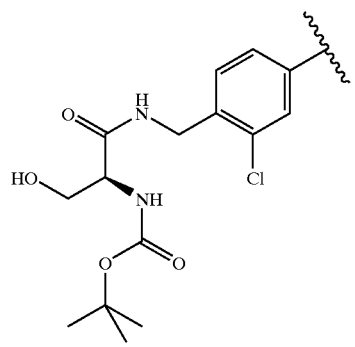 | 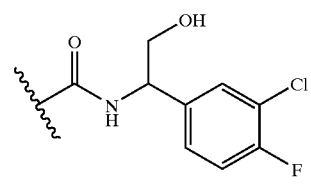 |
| II-A-340, II-B-340, and II-C-340 | 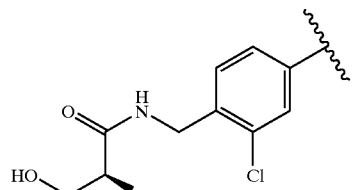 | 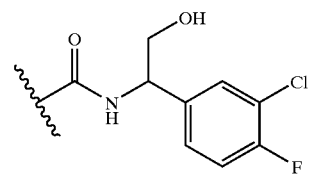 |
| II-A-341, II-B-341, and II-C-341 | 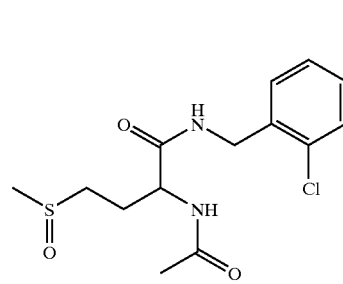 | 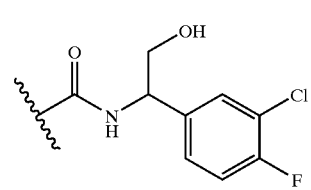 |

Additional preferred compounds, including those of formulae II-A', II-B', II-D', II-A°, II-B°, and II-D° are set forth in Table 2 below.

TABLE 2

Additional preferred compounds

| No. | $T_m$-$R^2$ | $Q_n$-$R^4$ |
|---|---|---|
| II-A-342, II-B-342, and II-C-342 | 2-F-3-Cl-phenyl | *acyl-N(CH3)-CH(CH3)-CH(OH)-phenyl* |
| II-A-343, II-B-343, and II-C-343 | methyl | *acyl-NH-CH(CH2OH)-phenyl* |
| II-A-344, II-B-344, and II-C-344 | methyl | *acyl-NH-CH(CH2CH2OH)-phenyl* |
| II-A-345, II-B-345, and II-C-345 | Methyl | *acyl-NH-CH(CH2CH2OH)-phenyl* |
| II-A-346, II-B-346, and II-C-346 | 3,5-dichlorophenyl | *acyl-NH-CH(CH2OH)-phenyl* |
| II-A-347, II-B-347, and II-C-347 | 3-F, 5-CF$_3$-phenyl | *acyl-NH-CH(CH2OH)-phenyl* |
| II-A-348, II-B-348, and II-C-348 | Methyl | *acyl-NH-CH(CH2OH)-phenyl* |
| II-A-349, II-B-349, and II-C-349 | H | *acyl-N(CH3)-CH(CH3)-CH(OH)-phenyl* |

TABLE 2-continued
Additional preferred compounds
| No. | $T_m$-$R^2$ | $Q_n$-$R^4$ |
|---|---|---|
| II-A-350, II-B-350, and II-C-350 | Methyl | 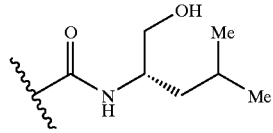 |
| II-A-351, II-B-351, and II-C-351 | Methyl | 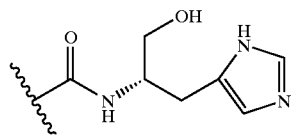 |
| II-A-352, II-B-352, and II-C-352 | Methyl | 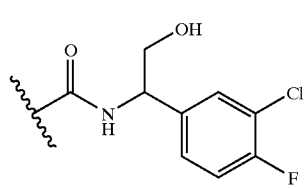 |
| II-A-353, II-B-353, and II-C-353 | Cyclohexyl | 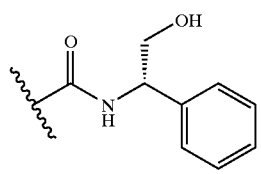 |
| II-A-354, II-B-354, and II-C-354 | Cyclopropyl | 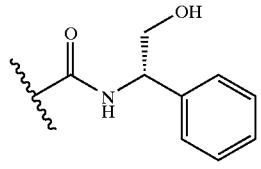 |
| II-A-355, II-B-355, and II-C-355 | Methyl | 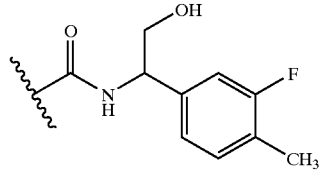 |
| II-A-356, II-B-356, and II-C-356 | Methyl | 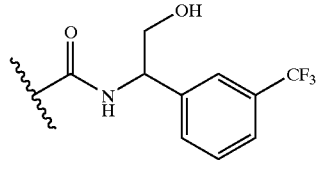 |
| II-A-357, II-B-357, and II-C-357 | $CH_2OCH_3$ | 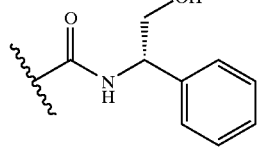 |

TABLE 2-continued
Additional preferred compounds
| No. | $T_m$-$R^2$ | $Q_n$-$R^4$ |
|---|---|---|
| II-A-358, II-B-358, and II-C-358 | CH$_2$OH | 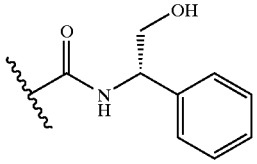 |
| II-A-359, II-B-359, and II-C-359 | Methyl | 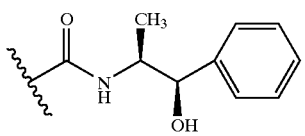 |
| II-A-360, II-B-360, and II-C-360 | Methyl | 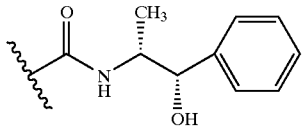 |
| II-A-361, II-B-361, and II-C-361 | Methyl | 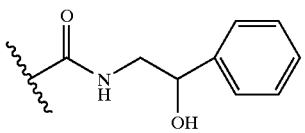 |
| II-A-362, II-B-362, and II-C-362 | Methyl | 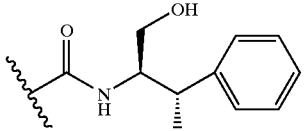 |
| II-A-363, II-B-363, and II-C-363 | Methyl | 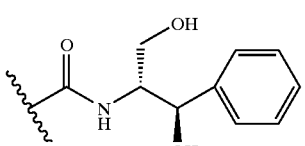 |
| II-A-364, II-B-364, and II-C-364 | H | 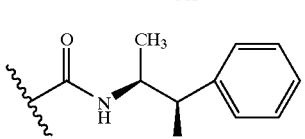 |
| II-A-365, II-B-365, and II-C-365 | H | 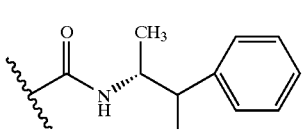 |
| II-A-366, II-B-366, and II-C-366 | H | 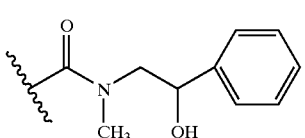 |
| II-A-367, II-B-367, and II-C-367 | H | 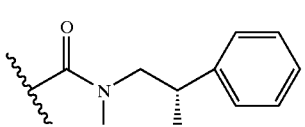 |

TABLE 2-continued

Additional preferred compounds

| No. | $T_m$-$R^2$ | $Q_n$-$R^4$ |
|---|---|---|
| II-A-368, II-B-368, and II-C-368 | H | *N(CH₃)-CH(CH₃)-CH(OH)-Ph amide* |
| II-A-369, II-B-369, and II-C-369 | H | *N(CH₃)-CH(CH₃)-CH(OH)-Ph amide (other stereo)* |
| II-A-370, II-B-370, and II-C-370 | Methyl | *NH-CH(3-pyridyl)-CH₂OH amide* |
| II-A-371, II-B-371, and II-C-371 | Methyl | *NH-CH(3-F-5-CF₃-phenyl)-CH₂OH amide* |
| II-A-372, II-B-372, and II-C-372 | Methyl | *NH-CH(3-F-phenyl)-CH₂OH amide* |
| II-A-373, II-B-373, and II-C-373 | Methyl | *NH-CH(2-F-phenyl)-CH₂OH amide* |
| II-A-374, II-B-374, and II-C-374 | Methyl | *NH-CH(3-CF₃-phenyl)-CH₂OH amide* |

TABLE 2-continued

Additional preferred compounds

| No. | $T_m$-$R^2$ | $Q_n$-$R^4$ |
|---|---|---|
| II-A-375, II-B-375, and II-C-375 | Methyl | 2-methoxyphenyl-CH(CH2OH)-NH-C(O)- |
| II-A-376, II-B-376, and II-C-376 | Methyl | 3-chlorophenyl-CH(CH2OH)-NH-C(O)- |
| II-A-377, II-B-377, and II-C-377 | Methyl | 3-methylphenyl-CH(CH2OH)-NH-C(O)- |
| II-A-378, II-B-378, and II-C-378 | Methyl | 3-fluorophenyl-CH(CH2OH)-NH-C(O)- |
| II-A-379, II-B-379, and II-C-379 | Methyl | 3-chlorophenyl-CH(CH2NH2)-NH-C(O)- |
| II-A-380, II-B-380, and II-C-380 | methyl | 3-chlorophenyl-CH(CH2CH2NH2)-NH-C(O)- |
| II-A-381, II-B-381, and II-C-381 | H | 3-chlorophenyl-CH(CH2NH2)-NH-C(O)- |

TABLE 2-continued

Additional preferred compounds

| No. | $T_m$-$R^2$ | $Q_n$-$R^4$ |
|---|---|---|
| II-A-382, II-B-382, and II-C-382 | H | 3-chlorophenyl-CH(CH$_2$NH$_2$)-NH-C(=O)- |
| II-A-383, II-B-383, and II-C-383 | HO-CH$_2$-CH(CH$_3$)-C(=O)-NH-CH$_2$-(2-Cl,5-)phenyl- | pyridin-4-yl-CH$_2$-NH-C(=O)- |
| II-A-384, II-B-384, and II-C-384 | HO-CH$_2$-CH(CH$_3$)-C(=O)-NH-CH$_2$-(2-Cl,5-)phenyl- | 2-chlorobenzyl-NH-C(=O)- |
| II-A-385, II-B-385, and II-C-385 | HO-CH$_2$-CH(CH$_3$)-C(=O)-NH-CH$_2$-(2-Cl,5-)phenyl- | 3-chlorophenyl-CH(CH$_2$NH$_2$)-NH-C(=O)- |
| II-A-386, II-B-386, and II-C-386 | HO-CH$_2$-CH(CH$_3$)-C(=O)-NH-CH$_2$-(2-Cl,5-)phenyl- | 3-chlorophenyl-CH(CH$_2$CH$_2$NH$_2$)-NH-C(=O)- |
| II-A-387, II-B-387, and II-C-387 | CH$_3$O-CH$_2$-CH(NH$_2$)-C(=O)-NH-CH$_2$-(2-Cl,5-)phenyl- | pyridin-4-yl-CH$_2$-NH-C(=O)- |
| II-A-388, II-B-388, and II-C-388 | CH$_3$O-CH$_2$-CH(NH$_2$)-C(=O)-NH-CH$_2$-(2-Cl,5-)phenyl- | 2-chlorobenzyl-NH-C(=O)- |

TABLE 2-continued

Additional preferred compounds

| No. | $T_m-R^2$ | $Q_n-R^4$ |
|---|---|---|
| II-A-389, II-B-389, and II-C-389 | [structure: methoxy-CH(NH2)-C(=O)-NH-CH2-(2-Cl,5-substituted phenyl)] | [structure: -C(=O)-NH-CH(3-chlorophenyl)-CH2-NH2] |
| II-A-390, II-B-390, and II-C-390 | [structure: methoxy-CH2-CH(NH2)-C(=O)-NH-CH2-(2-Cl,5-substituted phenyl)] | [structure: -C(=O)-NH-CH(3-chlorophenyl)-CH2-CH2-NH2] |

Additional exemplary compounds of formulae II-A, II-B, II-C, and II-E are set forth in Table 3 below.

TABLE 3

Compounds II-A, II-B, II-C, and II-E

| No. | Structure |
|---|---|
| II-A1 | [pyrrole-carboxamide-CH2-(2,3-dihydrobenzofuran-5-yl); triazole-(3-Cl,4-(dimethylaminomethyl)phenyl)] |
| II-A2 | [pyrrole-carboxamide-CH2-(pyridin-4-yl); triazole-(3-Cl,4-(hydroxymethyl)phenyl)] |

TABLE 3-continued

Compounds II-A, II-B, II-C, and II-E

| No. | Structure |
|---|---|
| II-A3 | [pyrrole-carboxamide-CH2-(pyridin-4-yl); triazole-(2-CF3,4-OH phenyl)] |
| II-A4 | [pyrrole-CH2-NH-CH2-(3,4-difluorophenyl); triazole-(6-hydroxypyridin-3-yl)] |
| II-A5 | [pyrrole-carboxamide-CH2-(3-CF3-phenyl); triazole-(2-Cl,4-(O-C(=O)-NHCH3)phenyl)] |

TABLE 3-continued
Compounds II-A, II-B, II-C, and II-E
| No. | Structure |
|---|---|
| II-A6 | 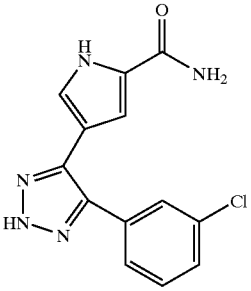 |
| II-A7 | 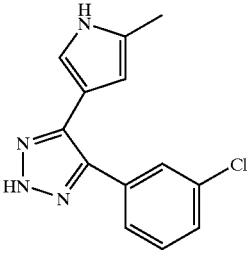 |
| II-A8 | 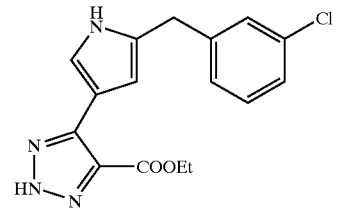 |
| II-B1 | 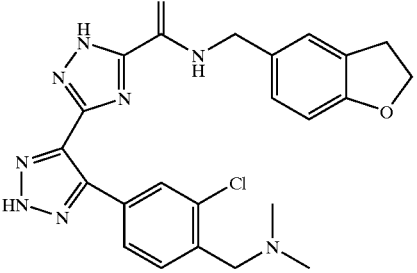 |
| II-B2 | 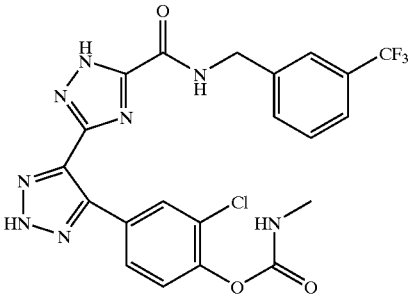 |
| II-B3 | 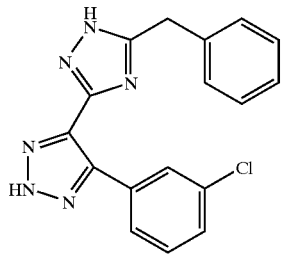 |
| II-B4 | 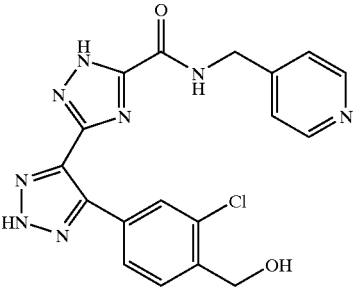 |
| II-B5 | 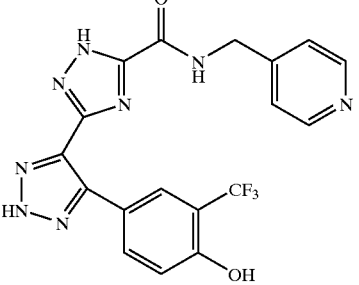 |
| II-B6 | 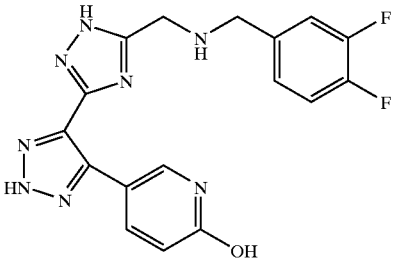 |
| II-C1 | 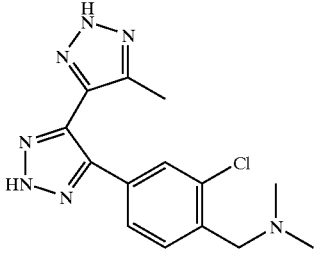 |

TABLE 3-continued
Compounds II-A, II-B, II-C, and II-E
| No. | Structure |
|---|---|
| II-C2 | 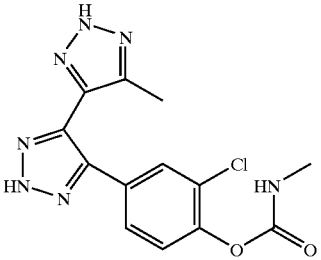 |
| II-C3 | 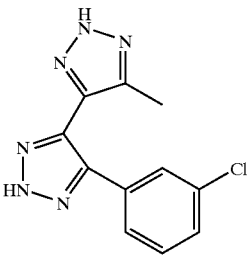 |
| II-C4 | 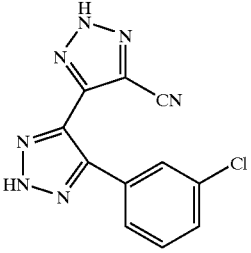 |
| II-C5 | 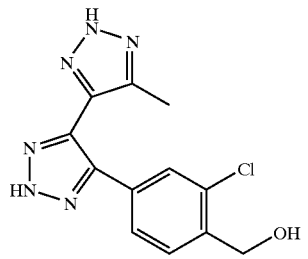 |
| II-C6 | 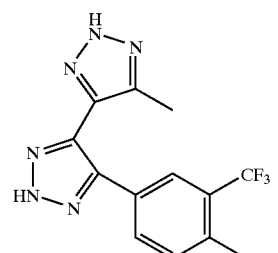 |
| II-C7 | 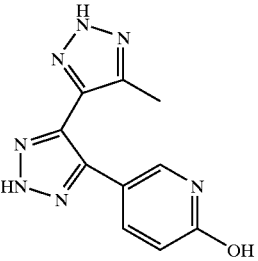 |
| II-E1 | 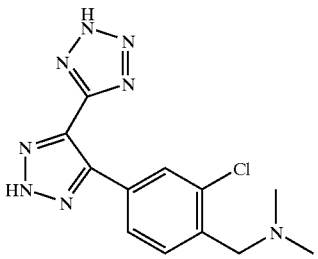 |
| II-E2 | 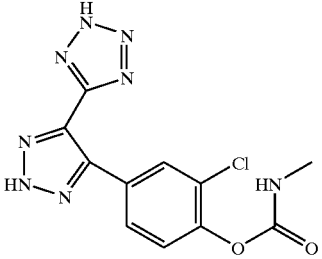 |
| II-E3 | 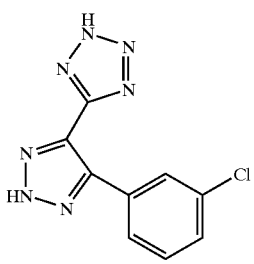 |
| II-E4 | 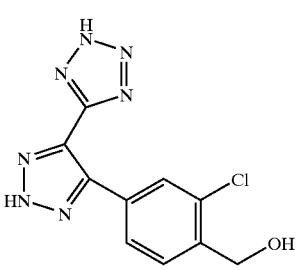 |

TABLE 3-continued
Compounds II-A, II-B, II-C, and II-E
| No. | Structure |
|---|---|
| II-E5 | 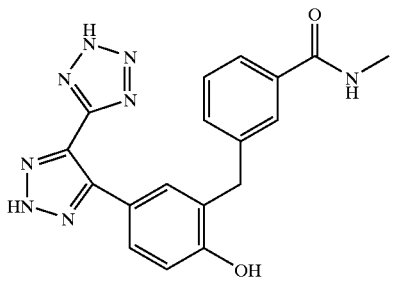 |
| II-E6 | 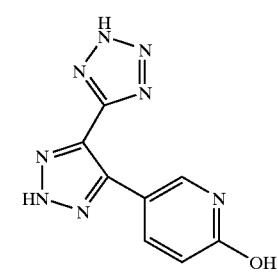 |
Additional preferred compounds of formula II-A are provided in Table 4 below:
TABLE 4
Additional Compounds II-A
| No. | Structure |
|---|---|
| II-A9 | 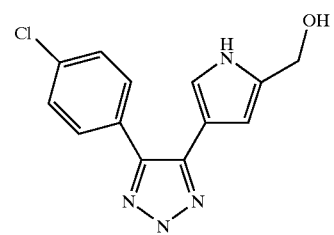 |
| II-A10 | 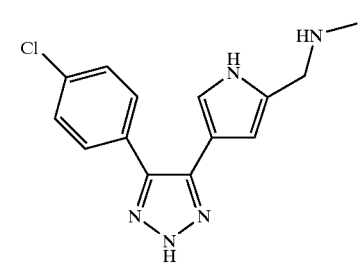 |
| II-A11 | 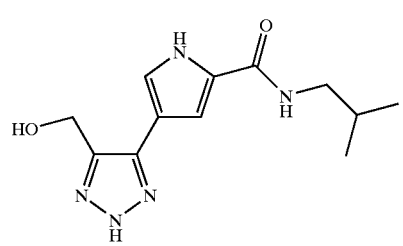 |
TABLE 4-continued
Additional Compounds II-A
| No. | Structure |
|---|---|
| II-A12 | 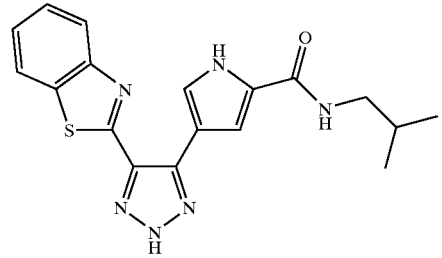 |
| II-A13 | 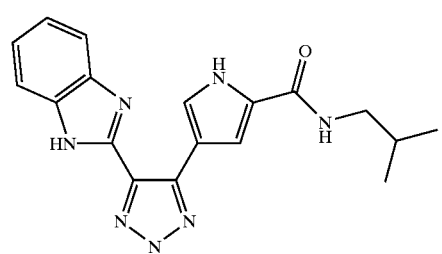 |
| II-A14 | 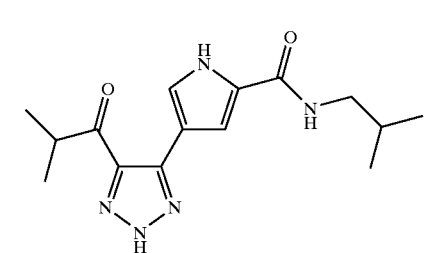 |
| II-A15 | 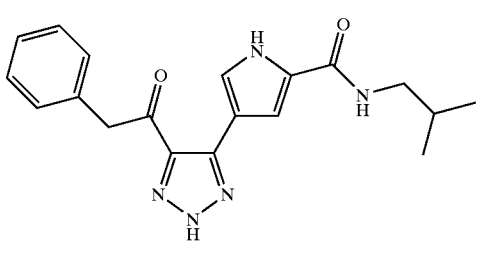 |
| II-A16 | 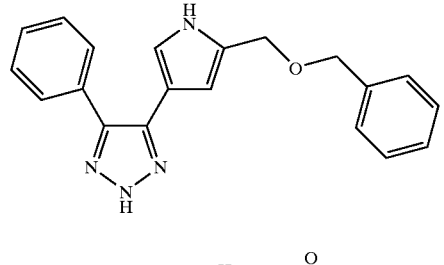 |
| II-A17 | 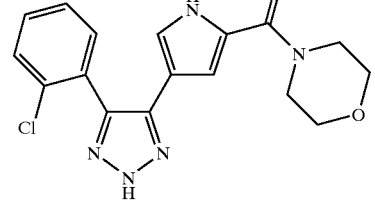 |

TABLE 4-continued

Additional Compounds II-A

| No. | Structure |
|---|---|
| II-A18 | 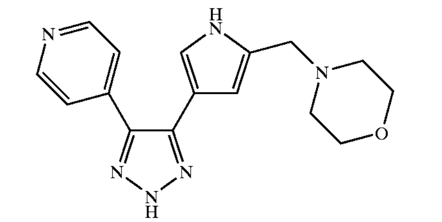 |
| II-A19 | 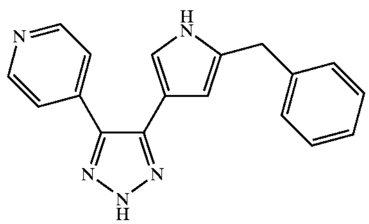 |
| II-A20 | 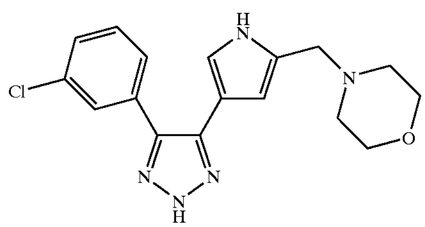 |
| II-A21 | 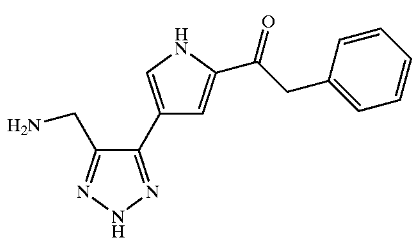 |
| II-A22 | 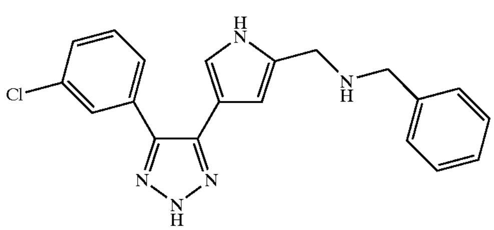 |
| II-A23 | 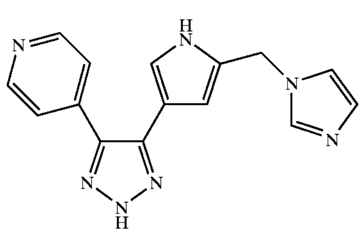 |
| II-A24 | |
| II-A25 | |
| II-A26 | |
| II-A27 | |
| II-A28 | |
| II-A29 | |

TABLE 4-continued

Additional Compounds II-A

| No. | Structure |
|-----|-----------|
| II-A30 | 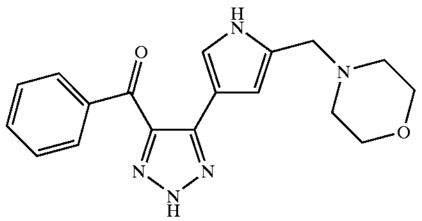 |
| II-A31 | 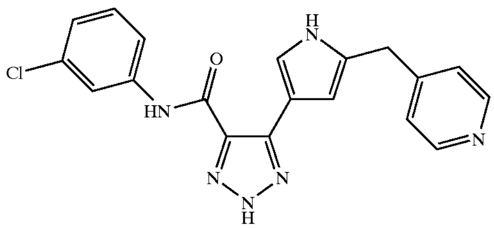 |
| II-A32 | 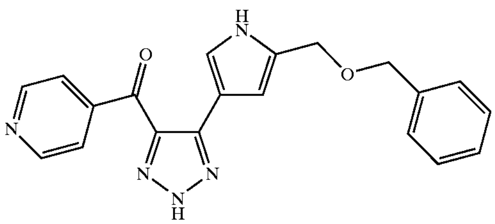 |
| II-A33 | 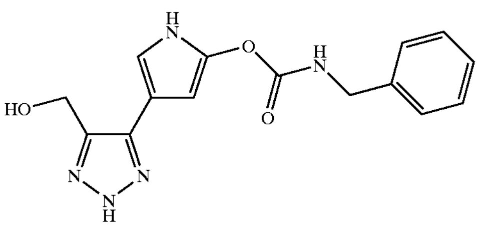 |
| II-A34 | 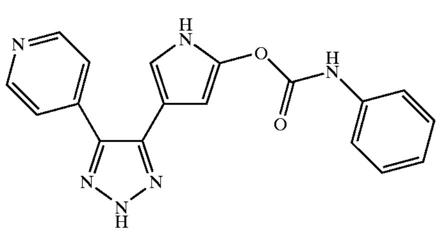 |
| II-A35 | 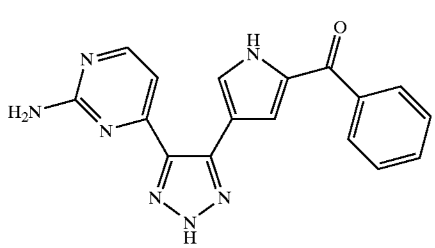 |
| II-A36 | |
| II-A37 | |
| II-A38 | |

Preferred embodiments of this invention are represented by formulae III-A, III-B, III-C, and III-D:

III-A

III-B

III-C

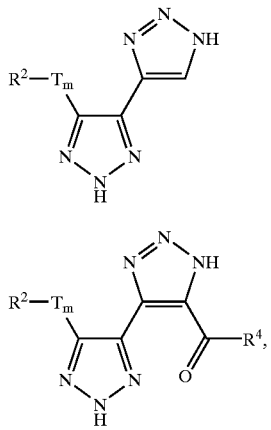

III-D wherein T, m, $R^2$, $R^4$ are as described above.

Preferred $R^2$ and $R^4$ of formulae III-A, III-B III-C, and III-D are as described above for formulae II-A, II-B, II-C, and II-D.

Another object of the invention is to provide methods of producing the above-identified compounds of formula I. Schemes 1–6 depict syntheses of the triazole-pyrrole (Schemes 1–2), triazole-[1,2,4]triazole (Scheme 3), triazole-[1,2,3]triazole (Schemes 4–5), and triazole-tetrazole (Scheme 6) compounds of this invention. One having ordinary skill in the art will recognize that Schemes 1–6 may be altered according to the functional groups present to make analogous compounds of this invention.

Scheme 1 -
Triazole-pyrrole

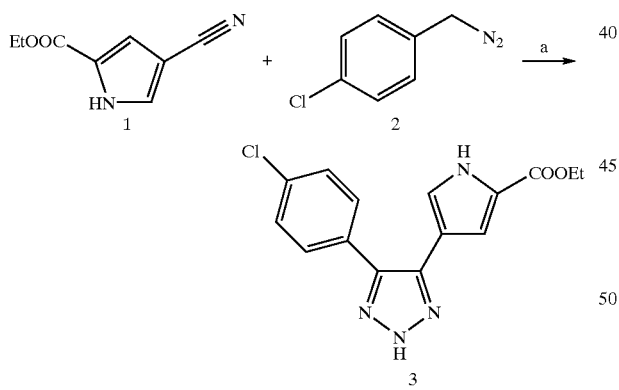

Reagents and conditions: (a) KOtBu, toluene, reflux

Scheme 1 above shows a general synthetic route used to prepare the pyrrol-3-yl compounds of formula II-A of this invention when m is zero and $R^2$ is an optionally substituted phenyl group. In Scheme 1, the triazole ring is formed by combining a cyano-1-pyrrole such as 1 and a diazo compound such as 2 in the presence of KOtBu in refluxing toluene. One of skill in the art will recognize that the above scheme may be used to synthesize compounds wherein $R^2$ is other than substituted phenyl. In addition, a compound such as 3 may be further derivatized to produce a variety of substituents $Q_n$-$R^4$.

Scheme 2 -
Triazole-pyrrole

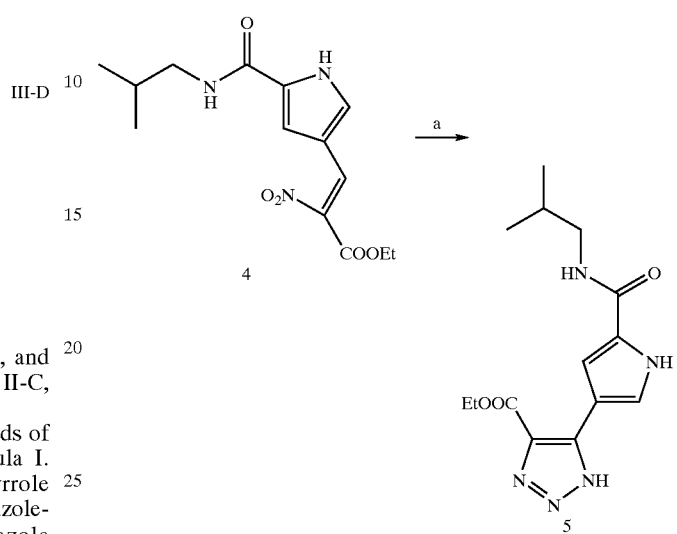

Reagents and conditions: (a) NaN₃, DMSO cheme 2 shows an alternate method for synthesizing the pyrrol-3-yl compounds II-A of the present invention. In Scheme 2, the triazole ring is formed by reacting a compound such as pyrrole derivative 4 with $NaN_3$ in DMSO. One of skill in the art will recognize that the above scheme may be used to synthesize compounds with a variety of $Q_n$-$R^4$ substituents. In addition, a compound such as 5 may be further derivatized to produce a variety of substituents $T_m$-$R^2$.

Scheme 3 -
Triazole-[1,2,4]triazole

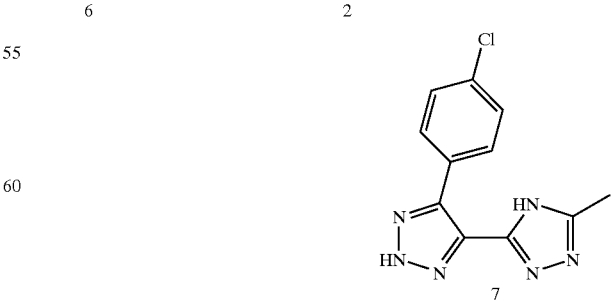

Reagents and conditions: (a) acetic anhydride, 140° C.; (b) (i) 2, KOtBu, toluene, reflux, (ii) H₂, Pd/C, EtOH Scheme 3 depicts the [1,2,4]triazole formation in step (a) by the method described in Bladin et al., Chem. Der., 1885, pp. 1544. Step (b) depicts formation of the [1,2,3]triazole ring as in Scheme 1 above. One of skill in the art will recognize that Scheme 3 may be used to synthesize compounds wherein $R^2$ is other than substituted phenyl. In addition, a compound such as 7 may be further derivatized to produce a variety of substituents $Q_n$-$R^4$.

Scheme 4 -
Triazole-[1,2,3]triazole

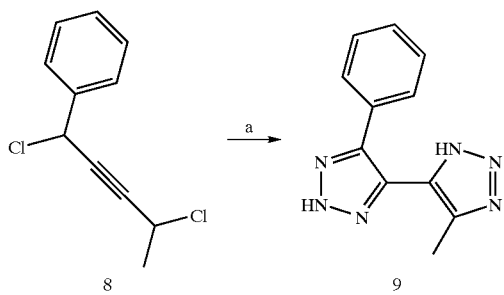

8                       9

Reagents and conditions: (a) TMS—$N_3$, $NaN_3$, NaOH

Scheme 4 depicts the cyclization to form the [1,2,3]triazole-[1,2,3]triazole system according to the method of Banert et al., Chem. Ber., 1989, pp. 1175. One of skill in the art will recognize that Scheme 4 may be used to synthesize compounds wherein $R^2$ is other than substituted phenyl. In addition, a compound such as 9 may be further derivatized to produce a variety of substituents $Q_n$-$R^4$.

Scheme 5 -
Triazole-[1,2,3]triazole

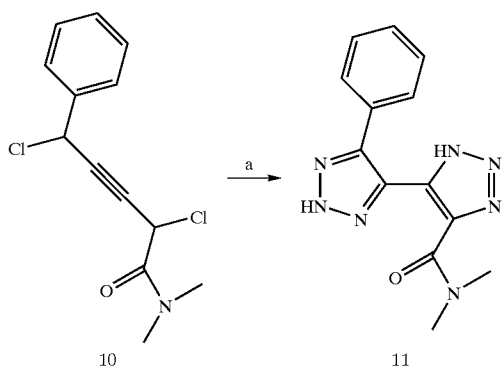

10                      11

Reagents and conditions: (a) TMS—$N_3$, $NaN_3$, NaOH

Scheme 5 depicts another [1,2,3]triazole-[1,2,3]triazole cyclization according to the method of Banert et al. above. One of skill in the art will recognize that Scheme 5 may be used to synthesize compounds wherein $R^2$ is other than substituted phenyl. In addition, a compound such as 11 may be further derivatized to produce a variety of substituents $Q_n$-$R^4$ Scheme 6 -
Triazole-tetrazole

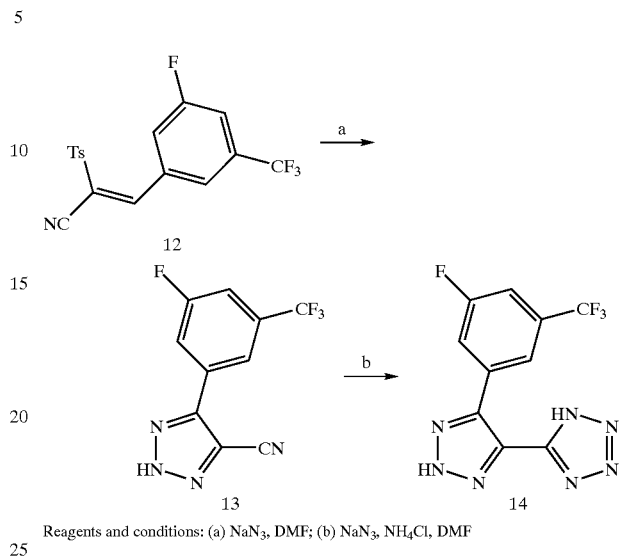

Reagents and conditions: (a) $NaN_3$, DMF; (b) $NaN_3$, $NH_4Cl$, DMF

Scheme 6 depicts the formation of the triazole in step (a) according to the method of Beck et al., Chem. Ber., 1973, pp. 106 and the formation of the tetrazole in step (b) according to the method of Katritzky et al., J. Heterocycl. Chem., 1996, pp. 1107. One of skill in the art will recognize that the above scheme may be used to synthesize compounds wherein $R^2$ is other than substituted phenyl. In addition, a compound such as 14 may be further derivatized to produce a variety of substituents $Q_n$-$R^4$.

Schemes 1–6 above show general synthetic routes useful in preparing the compounds of this invention wherein $T_m$-$R^2$ is an optionally substituted phenyl group, $R^3$ is H or methyl, and $Q_n$-$R^4$ is methyl or a carbonyl derivative. One having skill in the art may synthesize other compounds of this invention following the teachings of this specification, using reagents that are readily synthesized or commercially available.

The activity of a compound utilized in this invention as an inhibitor of ERK, may be assayed in vitro, in vivo or in a cell line according to methods known in the art. In vitro assays include assays that determine inhibition of either the phosphorylation activity or ATPase activity of activated ERK. Alternate in vitro assays quantitate the ability of the inhibitor to bind to ERK. Inhibitor binding may be measured by radiolabelling the inhibitor prior to binding, isolating the inhibitor/ERK complex and determining the amount of radiolabel bound. Alternatively, inhibitor binding may be determined by running a competition experiment where new inhibitors are incubated with ERK bound to known radioligands. Detailed conditions for assaying a compound utilized in this invention as an inhibitor of ERK kinase are set forth in the Examples below.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to detectably inhibit a protein kinase, particularly ERK in a biological sample or in a patient. Preferably the composition of this invention is formulated for administration to a patient in need of such composition.

Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in ERK activity between a sample comprising said composition and an ERK kinase and an equivalent sample comprising ERK kinase in the absence of said composition. According to a preferred embodiment, inhibition of kinase activity by a compound according to the present invention is greater than 10% compared to the kinase activity in the absence of the compound. Preferably, inhibition is greater than 20%, 30%, or 40%, and even more preferably greater than 50%, 60%, 70%, 80%, or 90%.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N+(C_{1-4}\,alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral[1] as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec", adriamycin, dexamethasone, vincristine, cyclophosphamide, fluorouracil, topotecan, taxol, interferons, and platinum derivatives.

Other examples of agents the compounds of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguamides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting ERK kinase activity in a biological sample comprising the step of contacting said biological sample with a compound of this invention, or a pharmaceutically acceptable composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of ERK kinase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention provides a method for treating or lessening the severity of an ERK-mediated disease or condition in a patient comprising the step of administering to said patient a pharmaceutically acceptable composition according to the present invention.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Compounds of the present invention are also useful as inhibitors of related kinases to ERK. The term "related kinases" refer to protein kinases having residues which are similar to those residues which line the ERK binding site. Without wishing to be bound by theory, applicants speculate that this inhibitory activity is due to the close structural similarity between the active sites of ERK and related kinases. The alignment of the ERK sequence with other kinases can be derived from common software programs such as the "bestfit" program available from Genetics Computer Group. This program uses the local homology algorithm described by Smith and Waterman in Advances in Applied Mathematics 2; 482 (1981).

Related kinases inhibited by the compounds of this invention would contain residues, identified by the above standard protein sequence alignment software, corresponding to the ERK residues: I31, E33, G34, A35, Y36, G37, M38, V39, A52, K54, R67, T68, E71, I84, I86, I103, Q105, D106, L107, M108, E109, D111, K114, D149, K151, S153, N154, L156, C166, and D167, with a similarity score of 80% or greater. In a more preferred embodiment the similarity score is 85%, more preferably 90%, even more preferably 95%, 96%, 97% or 98%. The similarity score may be determined using standard amino acid substitution tables such as those described by Dayhoff (Dayhoff, M. O., et al, *Atlas of Protein Sequence and Structure*, 1979) and Blosom-Henikoff (Blosum-Henikoff, S and Henikoff, J. G., *PNAS*, 1992, 89:10915–10919). The term "related kinases" also includes those containing residues with a similarity score of 80% or greater to the following ERK residues: I31, G37, A52, I103, E109, and N154. In a more preferred embodiment the similarity score is 85%, more preferably 90%, even more preferably 95%, 96%, 97% or 98%.

The present method is especially useful for treating a disease that is alleviated by the use of an inhibitor of ERK or related kinases. As used herein, unless otherwise indicated, the term "ERK" refers to all isoforms of the ERK enzyme including, but not limited to, ERK1, ERK2, ERK3, ERK4, ERK5, ERK6, and ERK7.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutically acceptable compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

EXAMPLE 1

ERK Inhibition Assay

Compounds are assayed for the inhibition of ERK2 by a spectrophotometric coupled-enzyme assay (Fox et al (1998) *Protein Sci* 7, 2249). In this assay, a fixed concentration of activated ERK2 (10 nM) is incubated with various concentrations of the compound in DMSO (2.5%) for 10 min. at 30° C. in 0.1 M HEPES buffer, pH 7.5, containing 10 mM $MgCl_2$, 2.5 mM phosphoenolpyruvate, 200 $\mu$M NADH, 150 $\mu$g/mL pyruvate kinase, 50 $\mu$g/mL lactate dehydrogenase, and 200 $\mu$M erktide peptide. The reaction is initiated by the addition of 65 $\mu$M ATP. The rate of decrease of absorbance at 340 nm is monitored, which indicates the extent of uninhibited enzyme present in the assay. The $IC_{50}$ is evaluated from the rate data as a function of inhibitor concentration.

EXAMPLE 2

ERK Inhibition Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84 wells of a 96 well plate at a seeding density of 10,000 cells/well/150 $\mu$L. The cells are allowed to attach to the plate by incubating at 37° C. for 2 hours. A solution of test compound is prepared in complete media by serial dilution to obtain the following concentrations: 20 $\mu$M, 6.7 $\mu$M, 2.2 $\mu$M, 0.74 $\mu$M, 0.25 $\mu$M, and 0.08 $\mu$M. The test compound solution (50 $\mu$L) is added to each of 72 cell-containing wells. To the 12 remaining cell-containing wells, only complete media (200 $\mu$L) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 $\mu$Ci/mL in RPMI medium then 20 $\mu$L of this solution is added to each well. The plates are further incubated at 37° C. for 8 hours then harvested and analyzed for $^3$H-thymidine uptake using a liquid scintillation counter.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

We claim:

1. A compound of formula II-A or II-B:

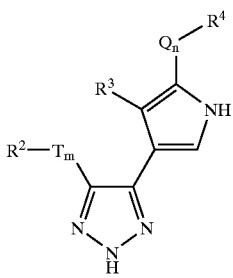

II-A

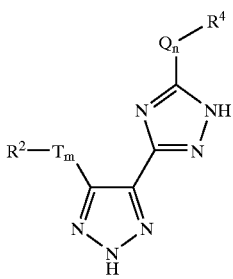

II-B or a pharmaceutically acceptable salt or derivative thereof, wherein:

T and Q are each independently selected from —C($R^7$)$_2$—, —C(O)—, —C(O)C(O)—, —C(O)N$R^7$—, —C(O)N$R^7$N$R^7$—, —CO$_2$—, —OC(O)—, —N$R^7$CO$_2$—, —O—, —N$R^7$C(O)N$R^7$—, —OC(O)N$R^7$—, —N$R^7$N$R^7$—, —N$R^7$C(O)—, —S—, —SO—, —SO$_2$—, —N$R^7$—, —SO$_2$N$R^7$—, or —N$R^7$SO$_2$—, —N$R^7$SO$_2$N$R^7$—; m and n are each independently selected from zero or one;

$R^2$ is selected from hydrogen, CN, halogen, R, N($R^7$)$_2$, OR, or OH;

each $R^3$ is independently selected from $R^7$, F, Cl, —(CH$_2$)$_y$N($R^7$)$_2$, —N($R^7$)$_2$, —O$R^7$, —S$R^7$, —N$R^7$C(O)$R^7$, —N$R^7$C(O)N($R^7$)$_2$, —C(O)N($R^7$)$_2$, —SO$_2$$R^7$, —N$R^7$SO$_2$$R^7$, —C(O)$R^7$, —C(O)$R^7$, CN or —SO$_2$N($R^7$)$_2$;

$R^4$ is selected from —(CH$_2$)$_y$$R^6$, —(CH$_2$)$_y$CH($R^6$)$_2$, —(CH$_2$)$_y$CH($R^8$)CH($R^6$)$_2$, —N($R^5$)$_2$, —N$R^5$(CH$_2$)$_y$N($R^5$)$_2$;

each R is independently selected from an optionally substituted group selected from C$_{1-6}$ aliphatic, C$_{6-10}$ aryl, heteroaryl having 5–10 ring atoms, and heterocyclyl having 3–10 ring atoms;

each $R^5$ is independently selected from R, —$R^7$, —C(O)$R^7$, —CO$_2$R, —C(O)N($R^7$)$_2$, —SO$_2$$R^7$, —(CH$_2$)$_y$$R^6$, or —(CH$_2$)$_y$CH($R^6$)$_2$;

y is 0–6;

each $R^6$ is independently selected from R, —(CH$_2$)$_y$R, —OR, —CO$_2$R, —(CH$_2$)$_y$N($R^7$)$_2$, —N($R^7$)$_2$, —O$R^7$, —S$R^7$, —N$R^7$C(O)$R^7$, —N$R^7$C(O)N($R^7$)$_2$, —C(O)N($R^7$)$_2$, —SO$_2$$R^7$, —N$R^7$SO$_2$$R^7$, —C(O)$R^7$, —CN, —SO$_2$N($R^7$)$_2$;

each $R^7$ is independently selected from hydrogen or an optionally substituted C$_{1-6}$ aliphatic group, or two $R^7$ on the same nitrogen are taken together with the nitrogen to form a 5–8 membered ring heterocyclyl or heteroaryl ring;

each $R^8$ is independently selected from R, —(CH$_2$)$_w$O$R^7$, —(CH$_2$)$_w$N($R^5$)$_2$, or —(CH$_2$)$_w$S$R^7$; and each w is independently 0–4.

2. A compound of formula II-C:

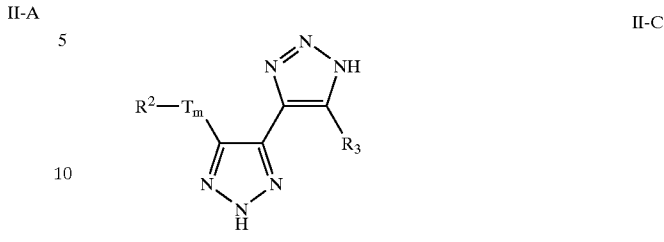

II-C or a pharmaceutically acceptable salt or derivative thereof, wherein:

T and Q are each independently selected from —C($R^7$)$_2$—, —C(O)—, —C(O)C(O)—, —C(O)N$R^7$—, —C(O)N$R^7$N$R^7$—, —CO$_2$—, —OC(O)—, —N$R^7$CO$_2$—, —O—, —N$R^7$C(O)N$R^7$—, —OC(O)N$R^7$—, —N$R^7$N$R^7$—, —N$R^7$C(O)—, —S—, —SO—, —SO$_2$—, —N$R^7$—, —SO$_2$N$R^7$—, or —N$R^7$SO$_2$—, —N$R^7$SO$_2$N$R^7$—;

m and n are each independently selected from zero or one;

$R^2$ is selected from hydrogen, CN, halogen, R, N($R^7$)$_2$, OR, or OH;

each $R^3$ is independently selected from hydrogen, an unsubstituted C$_{1-6}$ aliphatic group, F, Cl, —(CH$_2$)$_y$N($R^7$)$_2$, —N($R^7$)$_2$, —O$R^7$, —S$R^7$, —N$R^7$C(O)$R^7$, —N$R^7$C(O)N($R^7$)$_2$, —C(O)N($R^7$)$_2$. —SO$_2$$R^7$, —N$R^7$SO$_2$$R^7$, —C(O)$R^7$, —C(O)O$R^7$, CN or —SO$_2$N($R^7$)$_2$;

$R^4$ is selected from —(CH$_2$)$_y$$R^6$, —(CH$_2$)$_y$CH($R^6$)$_2$, —(CH$_2$)$_y$CH($R^8$)CH($R^6$)$_2$, —N($R^5$)$_2$, —N$R^5$(CH$_2$)$_y$N($R^5$)$_2$;

each R is independently selected from an optionally substituted group selected from C$_{1-6}$ aliphatic, C$_{6-10}$ aryl, heteroaryl having 5–10 ring atoms, and heterocyclyl havin 3–10 ring atoms;

each $R^5$ is independently selected from R, —$R^7$, —C(O)$R^7$, —CO$_2$R, —C(O)N($R^7$)$_2$, —SO$_2$$R^7$, —(CH$_2$)$_y$$R^6$, or —(CH$_2$)$_y$CH($R^6$)$_2$;

y is 0–6;

each $R^6$ is independently selected from R, —(CH$_2$)$_y$R, —OR, —CO$_2$R, —(CH$_2$)$_y$N($R^7$)$_2$, —N($R^7$)$_2$, —O$R^7$, —S$R^7$, —N$R^7$C(O)$R^7$, —N$R^7$C(O)N($R^7$)$_2$, —C(O)N($R^7$)$_2$, —SO$_2$$R^7$, —N$R^7$SO$_2$$R^7$, —C(O)$R^7$, —CN, —SO$_2$N($R^7$)$_2$;

each $R^7$ is independently selected from hydrogen or an optionally substituted C$_{1-6}$ aliphatic group, or two $R^7$ on the same nitrogen are taken together with the nitrogen to orm a 5–8 membered ring heterocyclyl or heteroaryl ring;

each $R^8$ is independently selected from R, —(CH$_2$)$_w$O$R^7$, —(CH$_2$)$_w$N($R^5$)$_2$, or —(CH$_2$)$_w$S$R^7$; and each w is independently 0–4.

3. A compound of formula II-D:

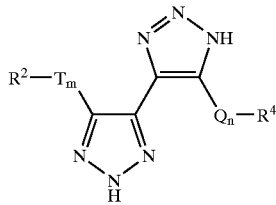

II-D or a pharmaceutically acceptable salt or derivative thereof, wherein:

T is selected from —C(R⁷)₂—, —C(O)—, —C(O)C(O)—, —C(O)NR⁷—, —C(O)NR⁷NR⁷—, —CO₂—, —OC(O)—, —NR⁷CO₂—, —O—, —NR⁷C(O)NR⁷—, —OC(O)NR⁷—, —NR⁷NR⁷—, —NR⁷C(O)—, —S—, —SO—, —SO₂—, —NR⁷—, —SO₂NR⁷—, or —NR⁷SO₂—, —NR⁷SO₂NR⁷—;

Q is —C(O)—, —CO₂—, —CONH—, —SO₂—, —SO₂NH—, —OC(O)NH—, —C(O)ONH—, or —C(O)NHNH—;

m and n are each independently selected from zero or one;

R² is selected from hydrogen, CN, halogen, R, N(R⁷)₂, OR, or OH;

each R³ is independently selected from R⁷, F, Cl, —(CH₂)ᵧN(R⁷)₂, —N(R⁷)₂, —OR⁷, —SR⁷, —NR⁷C(O)R⁷, —NR⁷C(O)N(R⁷)₂, —C(O)N(R⁷)₂, —SO₂R⁷, —NR⁷SO₂R⁷, —C(O)R⁷, —C(O)OR⁷, CN or —SO₂N(R⁷)₂;

R⁴ is selected from —(CH₂)ᵧR⁶, —(CH₂)ᵧCH(R⁶)₂, —(CH₂)ᵧCH(R⁸)CH(R⁶)₂, —N(R⁵)₂, —NR⁵(CH₂)ᵧN(R⁵)₂;

each R is independently selected from an optionally substituted group selected fro C₁₋₆ aliphatic, C₆₋₁₀ aryl, heteroaryl having 5–10 ring atoms, and heterocyclyl having 3–10 ring atoms;

each R⁵ is independently selected from R, —R⁷, —C(O)R⁷, —CO₂R, —C(O)N(R⁷)₂, —SO₂R⁷, —(CH₂)ᵧR⁶, or —(CH₂)ᵧCH(R⁶)₂;

y is 0–6;

each R⁶ is independently selected from R, —(CH₂)ᵧR, —OR, —CO₂R, —(CH₂)ᵧN(R⁷)₂, —N(R⁷)₂, —OR⁷, —SR⁷, —NR⁷C(O)R⁷, —NR⁷C(O)N(R⁷)₂, —C(O)N(R⁷)₂, —SO₂R⁷, —NR⁷SO₂R⁷, —C(O)R⁷, —CN, —SO₂N(R⁷)₂;

each R⁷ is independently selected from hydrogen or an optionally substituted C₁₋₆ aliphatic group, or two R⁷ on the same nitrogen are taken together with the nitrogen to rm a 5–8 membered ring heterocyclyl or heteroaryl ring;

each R⁸ independently selected from R, —(CH₂)ᵥOR⁷, —(CH₂)ᵥN(R⁵)₂, or —(CH₂)ᵥSR⁷; and each w is independently 0–4.

4. The compound according to claim 1 wherein said compound is of formula II-A:

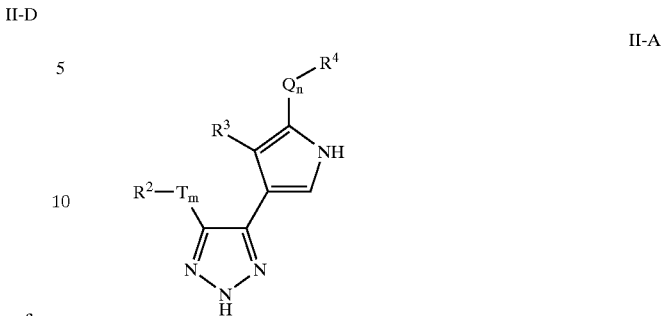

II-A or a pharmaceutically acceptable salt or derivative thereof.

5. The compound according to any one of claims 1, 2, or 3, wherein said compound has one or more features selected from the group consisting of: (a) TₘR² is hydrogen, N(R⁷)₂, OH, 3–6 membered carbocyclyl, or an optionally substituted group selected from C₁₋₆ aliphatic or a 5–6 membered aryl or heteroaryl ring; (b) Q is —CO—, —CO₂—, —CONH—, —SO₂—, —SO₂NH—, —OC(O)NH—, —C(O)ONH—, or —CONHNH—; (c) R⁴ is —NR⁵(CH₂)ᵧN(R⁵)₂, —(CH₂)ᵧR⁶, —(CH₂)ᵧCH(R⁶)₂, or —(CH₂)ᵧCH(R⁸)CH(R⁶)₂; (d) R⁵ is R, R⁷, or —(CH₂)ᵧCH(R⁶)₂; and (e) R⁶ is an optionally substituted group selected from phenyl, 5–6 membered heteroaryl, or 5–6 membered heterocyclyl.

6. The compound according to claim 5 wherein: (a) TₘR² is hydrogen, N(R⁷)₂, OH, 3–6 membered carbocyclyl, or an optionally substituted group selected from C₁₋₆ aliphatic or a 5–6 membered aryl or heteroaryl ring; (b) Q is —CO—, —CO₂—, —CONH—, —SO₂—, —SO₂NH—, —OC(O)NH—, —C(O)ONH—, or —CONHNH—; (c) R⁴ is —NR⁵(CH₂)ᵧN(R⁵)₂, —(CH₂)ᵧR⁶, —(CH₂)ᵧCH(R⁶)₂, or —(CH₂)ᵧCH(R⁸)CH(R⁶)₂; (d) R⁵ is R, R⁷, or —(CH₂)ᵧCH(R⁶)₂; and (e) R⁶ is an optionally substituted group selected from phenyl, 5–6 membered heteroaryl or 5–6 membered heterocyclyl.

7. The compound according to claim 6 wherein: (a) TₘR² is selected from optionally substituted phenyl, methyl, ethyl, propyl, cyclopropyl, cyclohexyl, CH₂OCH₃, CH₂OH, NH₂, NHCH₃, NHAc, NHC(O)NHCH₃, or CH₂NHCH₃; (b) Q is —CO—, —CONH—, —SO₂—, or —SO₂NH—; (c) R⁴ is —(CH₂)ᵧR⁶, —(CH₂)ᵧCH(R⁶)₂, or —(CH₂)ᵧCH(R⁸)CH(R⁶)₂, wherein R⁸ is OH or CH₂OH; and (d) R⁶ is —CH₂OH, —(CH₂)₂OH, isopropyl, or an optionally substituted group selected from pyrrolidin-1-yl, morpholin-4-yl, piperidin-1-yl, piperazin-1-yl, 4-methyl[1,4]diazepan-1-yl, 4-phenyl-piperazine-1-yl, pyridin-3-yl, pyridin-4-yl, imidazolyl, furan-2-yl, 1,2,3,4-tetrahydroisoquinoline, tetrahydrofuran-2-yl, cyclohexyl, phenyl, or benzyl.

8. The compound according to claim 5 wherein said compound is selected from the following:

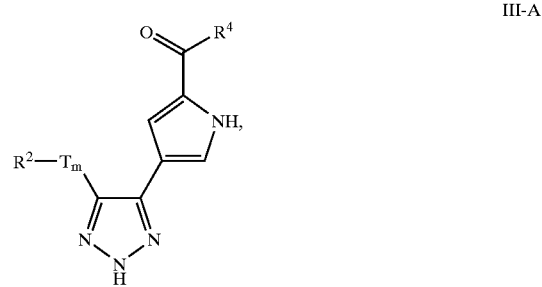

III-A

-continued

III-B

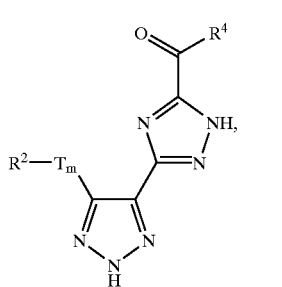

III-C

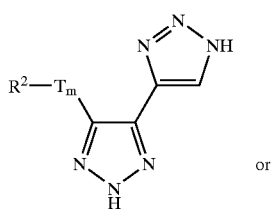

or

III-D

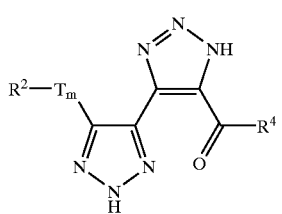

or a pharmaceutically acceptable salt or derivative thereof.

9. The compound according to claim 8 wherein said compound is of formula III-A:

III-A

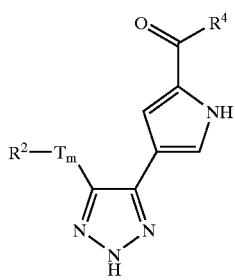

or a pharmaceutically acceptable salt or derivative thereof.

10. The compound according to claim 8 wherein said compound has one or more features selected from the group consisting of: (a) when in is one, T is —NH— or —O—; (b) $R^2$ is an optionally substituted aliphatic or aryl group, more preferably an optionally substituted phenyl group; (c) $R^4$ is —N($R^5$)$_2$, —N$R^5$(CH$_2$)$_y$N($R^5$)$_2$, —(CH$_2$)$_y$$R^6$, —(CH$_2$)$_y$CH($R^6$)$_2$, or $R^6$; (d) $R^5$ is R or $R^6$; and/or (e) $R^6$ is an optionally substituted group selected from aryl, aralkyl, heteroaryl, heteroarylalkyl, heterocyclyl or heterocyclylalkyl group.

11. The compound according to claim 5 wherein said compound is selected from the following:

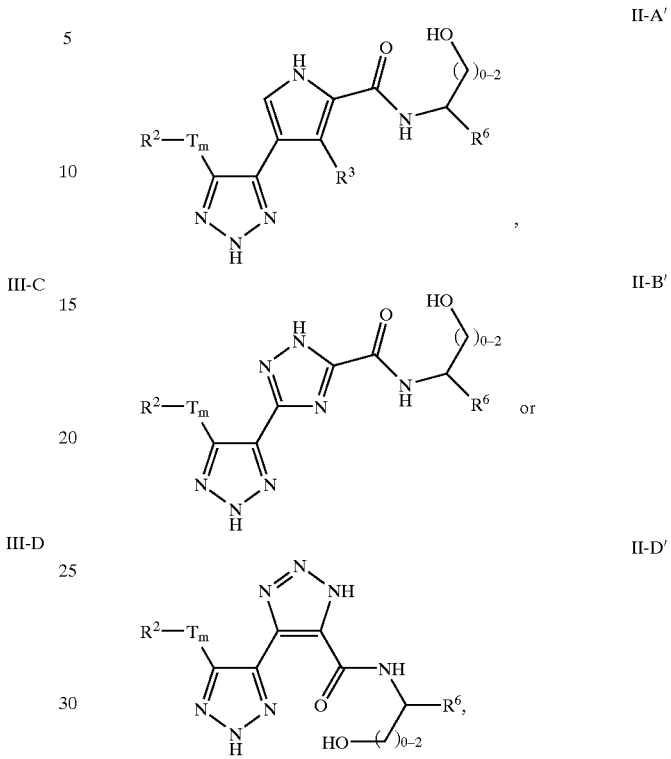

or a pharmaceutically acceptable salt or derivative thereof.

12. The compound according to claim 11 wherein said compound has one or more features selected from the group consisting of: (a) $T_mR^2$ is hydrogen, N($R^7$)$_2$, OH, 3–6 membered carbocyclyl, or an optionally substituted group selected from C$_{1-6}$ aliphatic or a 5–6 membered aryl or heteroaryl ring; and (b) $R^6$ is an optionally substituted 6-membered aryl, heteroaryl, or carbocyclic ring.

13. The compound according to claim 12 wherein: (a) $T_mR^2$ is selected from optionally substituted phenyl, methyl, ethyl, propyl, cyclopropyl, cyclohexyl, CH$_2$OCH$_3$, CH$_2$OH, OH, NH$_2$, NHCH$_3$, NHAc, NHC(O)NHCH$_3$, or CH$_2$NHCH$_3$; and (b) $R^6$ is cyclohexyl or an optionally substituted phenyl or pyridyl ring.

14. The compound according to claim 5 wherein said compound is selected from the following:

II-A°

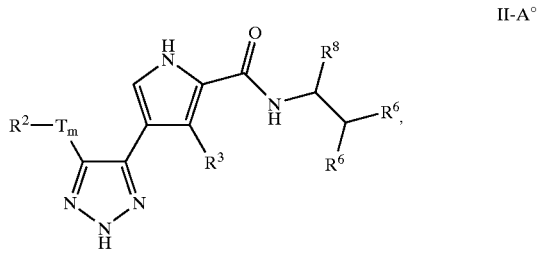

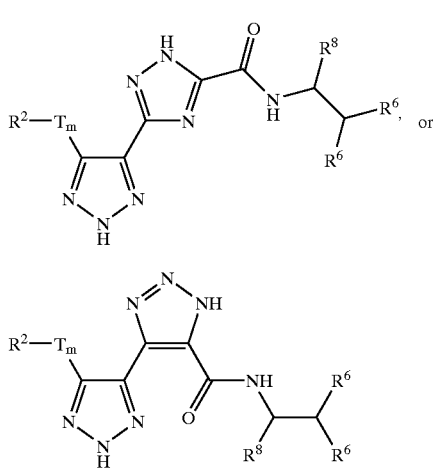

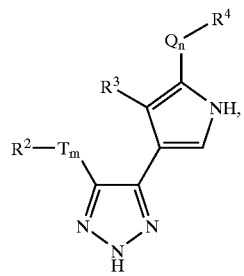

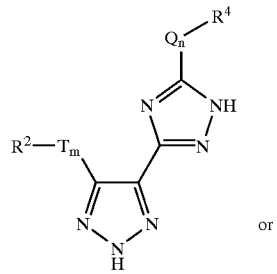

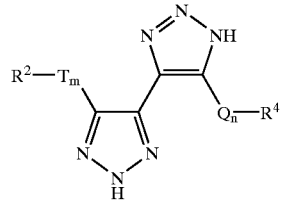

or a pharmaceutically acceptable salt or derivative thereof.

15. The compound according to claim 14 wherein said compound has one or more features selected from the group consisting of: (a) $T_m R^2$ is hydrogen, $N(R^5)_2$, OH, 3–6 membered carbocyclyl, or an optionally substituted group selected from $C_{1-6}$ aliphatic or a 5–6 membered aryl or heteroaryl ring; and (b) $R^6$ is R or $OR^7$, and $R^8$ is $R^7$ or $OR^7$.

16. The compound according to claim 15 wherein: (a) $T_m R^2$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, $NHC(O)NHCH_3$, or $CH_2NHCH_3$; and (b) $R^6$ is OH, $CH_2OH$, phenyl, pyridyl, or cyclohexyl, and $R^8$ is methyl, ethyl, OH, or $CH_2OH$.

17. The compound according to claim 5 wherein said compound is of formula II-A, II-B, or II-D and is selected from any one of the following compounds, wherein $R^3$ is H, m is zero, and n is one:

| No. | $R^2$ | $Q-R^4$ |
|---|---|---|
| II-A-1, II-B-1, and II-C-1 | phenyl | $CON(Me)_2$ |
| II-A-2, II-B-2, and II-C-2 | phenyl | $CO_2Et$ |
| II-A-3, II-B-3, and II-C-3 | 3-$NO_2$-phenyl | $CONHNH_2$ |
| II-A-4, II-B-4, and II-C-4 | phenyl | CO(pyrrolidin-1-yl) |
| II-A-5, II-B-5, and II-C-5 | phenyl | $CONHCH_2(Ph)$ |
| II-A-6, II-B-6, and II-C-6 | 3-$NO_2$-phenyl | $CO_2Et$ |
| II-A-7, II-B-7, and II-C-7 | 4-Cl-phenyl | $CO_2Et$ |
| II-A-8, II-B-8, and II-C-8 | 4-OMe-phenyl | $CO_2Et$ |
| II-A-9, II-B-9, and II-C-9 | 3-$NH_2$-phenyl | $CO_2Et$ |
| II-A-10, II-B-10, and II-C-10 | 3-OMe-phenyl | $CO_2Et$ |
| II-A-11, II-B-11, and II-C-11 | 4-F-phenyl | $CO_2Et$ |
| II-A-12, II-B-12, and II-C-12 | 4-$NO_2$-phenyl | $CO_2Et$ |
| II-A-13, II-B-13, and II-C-13 | 3-Cl-phenyl | $CO_2Et$ |
| II-A-14, II-B-14, and II-C-14 | 3-F-phenyl | $CO_2Et$ |
| II-A-15, II-B-15, and II-C-15 | phenyl | $CO_2H$ |
| II-A-16, II-B-16, and II-C-16 | 4-$NH_2$-phenyl | $CO_2Et$ |
| II-A-17, II-B-17, and II-C-17 | phenyl | $CONHCH_2CH_2N(Me)_2$ |
| II-A-18, II-B-18, and II-C-18 | phenyl | $CONHCH_2$(pyridin-3-yl) |
| II-A-19, II-B-19, and II-C-19 | phenyl | CO(morpholin-4-yl) |
| II-A-20, II-B-20, and II-C-20 | phenyl | CONH(isopropyl) |
| II-A-21, II-B-21, and II-C-21 | phenyl | CO(4-Me-piperazin-1-yl) |
| II-A-22, II-B-22, and II-C-22 | phenyl | $CONHCH_2$(furan-2-yl) |
| II-A-23, II-B-23, and II-C-23 | 3-OMe-phenyl | $CONMe_2$ |
| II-A-24, II-B-24, and II-C-24 | 3-OMe-phenyl | CO(pyrrolidin-1-yl) |
| II-A-25, II-B-25, and II-C-25 | 3-OMe-phenyl | $CONHCH_2CH_2N(Me)_2$ |
| II-A-26, II-B-26, and II-C-26 | 3-OMe-phenyl | $CONHCH_2$(pyridin-3-yl) |
| II-A-27, II-B-27, and II-C-27 | 3-OMe-phenyl | CO(morpholin-4-yl) |
| II-A-28, II-B-28, and II-C-28 | 3-OMe-phenyl | CONH(isopropyl) |
| II-A-29, II-B-29, and II-C-29 | 3-OMe-phenyl | CO(4-Me-piperazin-1-yl) |
| II-A-30, II-B-30, and II-C-30 | 3-OMe-phenyl | $CONHCH_2$(furan-2-yl) |
| II-A-31, II-B-31, and II-C-31 | 4-$NH_2$-phenyl | $CO_2Et$ |

-continued

| No. | R² | Q-R⁴ |
|---|---|---|
| II-A-32, II-B-32, and II-C-32 | H | CONMe₂ |
| II-A-33, II-B-33, and II-C-33 | H | CO(pyrrolidin-1-yl) |
| II-A-34, II-B-34, and II-C-34 | 3-(AcNH)-phenyl | CO₂Et |
| II-A-35, II-B-35, and II-C-35 | 4-(AcNH)-phenyl | CO₂Et |
| II-A-36, II-B-36, and II-C-36 | 3-(AcNH)-phenyl | CO₂Et |
| II-A-37, II-B-37, and II-C-37 | 4-(AcNH)-phenyl | CO₂Et |
| II-A-38, II-B-38, and II-C-38 | 3-Cl-phenyl | CONHBn |
| II-A-39, II-B-39, and II-C-39 | 3,5-dichlorophenyl | ![structure: C(=O)NH-CH(Ph)-CH2OH] |
| II-A-40, II-B-40, and II-C-40 | 3-Br-phenyl | CONH(3,4-difluorophenyl) |
| II-A-41, II-B-41, and II-C-41 | 3-Cl-phenyl | CONH(2-OH-1-Ph-ethyl) |
| II-A-42, II-B-42, and II-C-42 | 4-OH-3-I-5-nitrophenyl | CONH(2-OH-1-Ph-ethyl) |
| II-A-43, II-B-43, and II-C-43 | 3-Br-phenyl | ![structure: C(=O)NHCH2-(2,3-dihydrobenzofuran-5-yl)] |
| II-A-44, II-B-44, and II-C-44 | 5-NH₂-4-OH-3-I-phenyl | CONH(2-OH-1-Ph-ethyl) |
| II-A-45, II-B-45, and II-C-45 | 3-Br-phenyl | CONH(2-OH-1-Ph-ethyl) |
| II-A-46, II-B-46, and II-C-46 | 3-Br-phenyl | CONHCH₂(3-MeO-phenyl) |
| II-A-47, II-B-47, and II-C-47 | 3-Br-phenyl | CONHCH₂(3-CF₃-phenyl) |
| II-A-48, II-B-48, and II-C-48 | 3,5-dichlorophenyl | CONHCH₂(pyrid-4-yl) |
| II-A-49, II-B-49, and II-C-49 | 3-CF₃-phenyl | CONH(2-OH-1-Ph-ethyl) |
| II-A-50, II-B-50, and II-C-50 | 3-Cl-phenyl | CONHCH₂Ph |
| II-A-51, II-B-51, and II-C-51 | 3,5-dichlorophenyl | CONHOCH₂Ph |
| II-A-52, II-B-52, and II-C-52 | 4-OH-3-I-5-nitrophenyl | CONHCH₂Ph |
| II-A-53, II-B-53, and II-C-53 | 3-Cl-phenyl | CONHCH₂(pyrid-4-yl) |
| II-A-54, II-B-54, and II-C-54 | 3,4-dichlorophenyl | CONHOCH₂Ph |
| II-A-55, II-B-55, and II-C-55 | 3-Br-phenyl | CONHCH₂(4-SO₂Me-phenyl) |
| II-A-56, II-B-56, and II-C-56 | 3-Br-phenyl | CONHNH(3-CF₃-phenyl) |
| II-A-57, II-B-57, and II-C-57 | 3-Cl-phenyl | CONHOCH₂Ph |
| II-A-58, II-B-58, and II-C-58 | 3-Br-phenyl | ![structure: C(=O)NHCH2-(5-methylfuran-2-yl)] |
| II-A-59, II-B-59, and II-C-59 | 3-Br-phenyl | ![structure: C(=O)NH-CH(Ph)-CH2CH2OH] |
| II-A-60, II-B-60, and II-C-60 | 3-Br-phenyl | CONHCH₂(2-Me-phenyl) |
| II-A-61, II-B-61, and II-C-61 | 3,4-dichlorophenyl | CONHCH₂(pyrid-4-yl) |
| II-A-62, II-B-62, and II-C-62 | 3-Br-phenyl | CONH(1-Ph-propyl) |
| II-A-63, II-B-63, and II-C-63 | 3-F-phenyl | CONHCH₂Ph |
| II-A-64, II-B-64, and II-C-64 | 3,4-dichlorophenyl | ![structure: C(=O)N(Me)(Et)] |

-continued

| No. | R² | Q-R⁴ |
|---|---|---|
| II-A-65, II-B-65, and II-C-65 | 3-Br-phenyl | 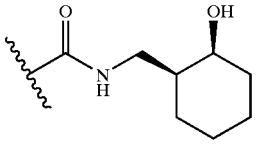 |
| II-A-66, II-B-66, and II-C-66 | 3,5-dichlorophenyl | CON(Me)(Et) |
| II-A-67, II-B-67, and II-C-67 | 3-Cl-phenyl | CONHCH₂(pyrid-3-yl) |
| II-A-68, II-B-68, and II-C-68 | 3-Br-phenyl | CONHCH₂(3,5-dimethoxyphenyl) |
| II-A-69, II-B-69, and II-C-69 | 3-Br-phenyl | CONHCH₂(2-OMe-phenyl) |
| II-A-70, II-B-70, and II-C-70 | 3-Cl-4-F-phenyl | CONHCH₂(pyrid-4-yl) |
| II-A-71, II-B-71, and II-C-71 | 3-Cl-4-F-phenyl | CON(Me)(Et) |
| II-A-72, II-B-72, and II-C-72 | 3-Br-phenyl | CONH(2-OH-1-Ph-ethyl) |
| II-A-73, II-B-73, and II-C-73 | 3-NH₂-phenyl | CONHCH₂Ph |
| II-A-74, II-B-74, and II-C-74 | 3,4-dichlorophenyl | CONHCH₂(pyrid-3-yl) |
| II-A-75, II-B-75, and II-C-75 | 3-Me-phenyl | CONH(2-OH-1-Ph-ethyl) |
| II-A-76, II-B-76, and II-C-76 | 3,5-dichlorophenyl | CONHCH₂(pyrid-3-yl) |
| II-A-77, II-B-77, and II-C-77 | 3-Cl-4-F-phenyl | CONHOCH₂Ph |
| II-A-78, II-B-78, and II-C-78 | 3,5-dichlorophenyl | CONHCH₂(tetrahydrofuran-2-yl) |
| II-A-79, II-B-79, and II-C-79 | 3-NO₂-phenyl | CONHCH₂Ph |
| II-A-80, II-B-80, and II-C-80 | 3-F-phenyl | CONHCH₂(pyrid-4-yl) |
| II-A-81, II-B-81, and II-C-81 | 3-Cl-2-F-phenyl | CON(Me)(Et) |
| II-A-82, II-B-82, and II-C-82 | 3-Cl-2-F-phenyl | CONHOCH₂Ph |
| II-A-83, II-B-83, and II-C-83 | 3-Br-phenyl | 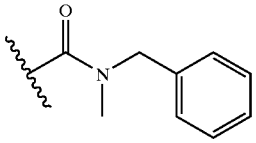 |
| II-A-84, II-B-84, and II-C-84 | 3-Cl-phenyl | CONHCH₂(tetrahydrofuran-2-yl) |
| II-A-85, II-B-85, and II-C-85 | 3,4-difluorophenyl | CONHOCH₂Ph |
| II-A-86, II-B-86, and II-C-86 | 3-Br-phenyl | CONH(3-OH-1-Ph-propyl) |
| II-A-87, II-B-87, and II-C-87 | 3-Br-phenyl | 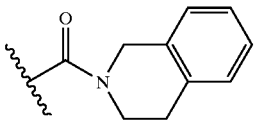 |
| II-A-88, II-B-88, and II-C-88 | 3,4-difluorophenyl | CONHCH₂(pyrid-4-yl) |
| II-A-89, II-B-89, and II-C-89 | 3-F-phenyl | CONHOCH₂Ph |
| II-A-90, II-B-90, and II-C-90 | 3-Me-phenyl | CONHCH₂Ph |
| II-A-91, II-B-91, and II-C-91 | 3-Br-phenyl | 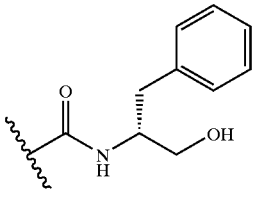 |
| II-A-92, II-B-92, and II-C-92 | 4-Cl-phenyl | CONHCH₂Ph |
| II-A-93, II-B-93, and II-C-93 | 3-Cl-phenyl | CON(Me)(Et) |
| II-A-94, II-B-94, and II-C-94 | 3-Br-phenyl | CONHCH₂(4-SO₂NH₂-phenyl) |
| II-A-95, II-B-95, and II-C-95 | 3-OH-phenyl | CONHCH₂Ph |
| II-A-96, II-B-96, and II-C-96 | 3-Me-phenyl | CONHCH₂(pyrid-4-yl) |
| II-A-97, II-B-97, and II-C-97 | Phenyl | CONHCH₂Ph |
| II-A-99, II-B-98, and II-C-98 | 2,5-difluorophenyl | CONHCH₂(pyrid-4-yl) |
| II-A-99, II-B-99, and II-C-99 | 4-Cl-phenyl | CONHOCH₂Ph |
| II-A-100, II-B-100, and II-C-100 | 3-Cl-4-F-phenyl | CONHCH₂(tetrahydrofuran-2-yl) |
| II-A-101, II-B-101, and II-C-101 | 3-Cl-4-F-phenyl | CONHCH₂(pyrid-3-yl) |

-continued

| No. | R² | Q-R⁴ |
|---|---|---|
| II-A-102, II-B-102, and II-C-102 | 3-Br-phenyl | CL(4-OH-Ph-piperidin-1-yl) |
| II-A-103, II-B-103, and II-C-103 | 2,3-difluorophenyl | CONHOCH₂Ph |
| II-A-104, II-B-104, and II-C-104 | 3-Cl-phenyl | CO(morpholin-4-yl) |
| II-A-105, II-B-105, and II-C-105 | 3-Br-phenyl | (6,7-dimethoxy-1-(hydroxymethyl)-3,4-dihydroisoquinolin-2(1H)-yl carbonyl) |
| II-A-106, II-B-106, and II-C-106 | 3-Cl-2-F-phenyl | CONHCH₂(tetrahydrofuran-2-yl) |
| II-A-107, II-B-107, and II-C-107 | 3-Cl-4-F-phenyl | CO(morpholin-4-yl) |
| II-A-108, II-B-108, and II-C-108 | 3-Cl-4-F-phenyl | CON(Me)(Et) |
| II-A-109, II-B-109, and II-C-109 | 3-Br-phenyl | CONHCH₂(4-NH₂-phenyl) |
| II-A-110, II-B-110, and II-C-110 | 3-Br-phenyl | CONHCH₂(4-(1,2,3-thiadiazol-5-yl)phenyl) |
| II-A-111, II-B-111, and II-C-111 | 4-F-phenyl | CONHCH₂Ph |
| II-A-112, II-B-112, and II-C-112 | 3,5-dichlorophenyl | CO(morpholin-4-yl) |
| II-A-113, II-B-113, and II-C-113 | 2,5-difluorophenyl | CONHOCH₂Ph |
| II-A-114, II-B-114, and II-C-114 | 3-Cl-2-F-phenyl | CONHCH₂(pyrid-3-yl) |
| II-A-115, II-B-115, and II-C-115 | 3-Cl-2-F-phenyl | CONHCH₂(pyrid-4-yl) |
| II-A-116, II-B-116, and II-C-116 | 3,4-difluorophenyl | CONHCH₂(pyrid-3-yl) |
| II-A-117, II-B-117, and II-C-117 | 4-OMe-phenyl | CONHCH₂Ph |
| II-A-118, II-B-118, and II-C-118 | 3-Br-phenyl | CONHCH₂(2,4,6-trimethoxyphenyl) |
| II-A-119, II-B-119, and II-C-119 | 3-F-phenyl | CONHCH₂(pyrid-3-yl) |
| II-A-120, II-B-120, and II-C-120 | 3,4-difluorophenyl | CONHCH₂(tetrahydrofuran-2-yl) |
| II-A-121, II-B-121, and II-C-121 | 3-Cl-2-F-phenyl | (1-Boc-piperidin-3-yl-methyl-aminocarbonyl) |
| II-A-122, II-B-122, and II-C-122 | 3-Br-phenyl | (4-(3-methoxyphenyl)piperazin-1-yl carbonyl) |
| II-A-123, II-B-123, and II-C-123 | 3-Br-phenyl | (4-(4-bromophenyl)-4-hydroxypiperidin-1-yl carbonyl) |
| II-A-124, II-B-124, and II-C-124 | 3-Br-phenyl | CONHCH₂(2,5-dimethoxyphenyl) |

-continued

| No. | R² | Q-R⁴ |
|---|---|---|
| II-A-125, II-B-125, and II-C-125 | 3,5-dichlorophenyl | 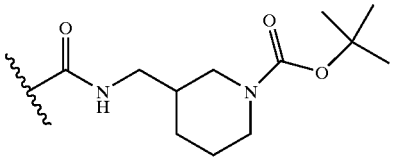 |
| II-A-126, II-B-126, and II-C-126 | 3-Br-phenyl | 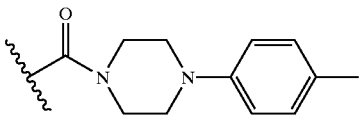 |
| II-A-127, II-B-127, and II-C-127 | 3,4-dichlorophenyl | CO(morpholin-4-yl) |
| II-A-128, II-B-128, and II-C-128 | 3-Br-phenyl | 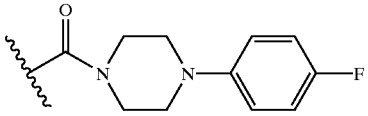 |
| II-A-129, II-B-129, and II-C-129 | 3-Cl-2-F-phenyl | CO(morpholin-4-yl) |
| II-A-130, II-B-130, and II-C-130 | 3-Br-phenyl | CONHCH$_2$CH$_2$OH |
| II-A-131, II-B-131, and II-C-131 | 3-NH$_2$-phenyl | CONHCH$_2$Ph |
| II-A-132, II-B-132, and II-C-132 | 3-MeOC(O)-phenyl | CONHCH$_2$Ph |
| II-A-133, II-B-133, and II-C-133 | 4-MeO-phenyl | CONHOCH$_2$Ph |
| II-A-134, II-B-134, and II-C-134 | Phenyl | CO(pyrrolidin-1-yl) |
| II-A-135, II-B-135, and II-C-135 | 3-MeO-phenyl | CO(morpholin-4-yl) |
| II-A-136, II-B-136, and II-C-136 | 3-Cl-phenyl | CO(4-Me-piperidin-1-yl) |
| II-A-137, II-B-137, and II-C-137 | 3-NO$_2$-phenyl | CONH$_2$NH$_2$ |
| II-A-138, II-B-138, and II-C-138 | 3-Br-phenyl | 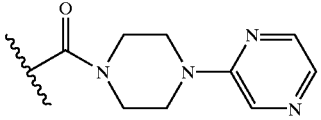 |
| II-A-139, II-B-139, and II-C-139 | 3-Br-phenyl | 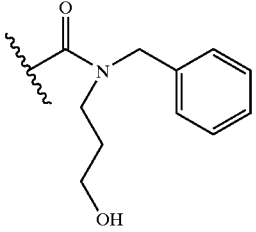 |
| II-A-140, II-B-140, and II-C-140 | 3-Cl-phenyl | CONHPh |
| II-A-141, II-B-141, and II-C-141 | 2,3-difluorophenyl | CONHCH$_2$(pyrid-4-yl) |
| II-A-142, II-B-142, and II-C-142 | 3-Cl-phenyl | 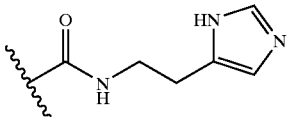 |
| II-A-143, II-B-143, and II-C-143 | Phenyl | CON(Me)$_2$ |
| II-A-144, II-B-144, and II-C-144 | 3-OMe-phenyl | CO(pyrrolidin-1-yl) |
| II-A-145, II-B-145, and II-C-145 | 3-OMe-phenyl | CONHCH$_2$(pyrid-3-yl) |
| II-A-146, II-B-146, and II-C-146 | 4-F-phenyl | CONHOCH$_2$Ph |
| II-A-147, II-B-147, and II-C-147 | 3-OMe-phenyl | CONHCH$_2$(furan-2-yl) |
| II-A-148, II-B-148, and II-C-148 | 3-NO$_2$-phenyl | COOEt |
| II-A-149, II-B-149, and II-C-149 | Phenyl | CONHCH$_2$(furan-2-yl) |
| II-A-150, II-B-150, and II-C-150 | Phenyl | CO(morpholin-4-yl) |
| II-A-151, II-B-151, and II-C-151 | 3-Cl-phenyl | COOEt |
| II-A-152, II-B-152, and II-C-152 | 3-Br-phenyl | CONHMe |
| II-A-153, II-B-153, and II-C-153 | Phenyl | CONHCH$_2$(pyrid-3-yl) |
| II-A-154, II-B-154, and II-C-154 | 3-OMe-phenyl | CON(Me)$_2$ |

-continued

| No. | R² | Q-R⁴ |
|---|---|---|
| II-A-155, II-B-155, and II-C-155 | 3-Cl-phenyl | (2-hydroxy-2,3-dihydro-1H-inden-1-yl)carbamoyl group |
| II-A-156, II-B-156, and II-C-156 | 3-Br-phenyl | N-(3-hydroxypropyl)-N-(pyridin-4-ylmethyl)carbamoyl group |
| II-A-157, II-B-157, and II-C-157 | 3-Br-phenyl | COOEt |
| II-A-158, II-B-158, and II-C-158 | phenyl | CONH(iPr) |
| II-A-159, II-B-159, and II-C-159 | 3-OMe-phenyl | CONH(iPr) |
| II-A-160, II-B-160, and II-C-160 | 3-COOH-phenyl | CONH(iPr) |
| II-A-161, II-B-161, and II-C-161 | 3-Br-phenyl | CONHO(iPr) |
| II-A-162, II-B-162, and II-C-162 | 3-F-phenyl | COOEt |
| II-A-163, II-B-163, and II-C-163 | 3-OMe-phenyl | CO(4-Me-piperidin-1-yl) |
| II-A-164, II-B-164, and II-C-164 | 4-NH₂-phenyl | COOEt |
| II-A-165, II-B-165, and II-C-165 | 4-NO₂-phenyl | COOEt |
| II-A-166, II-B-166, and II-C-166 | phenyl | CO(4-Me-piperidin-1-yl) |
| II-A-167, II-B-167, and II-C-167 | 4-Cl-phenyl | COOEt |
| II-A-168, II-B-168, and II-C-168 | 4-OMe-phenyl | COOEt |
| II-A-169, II-B-169, and II-C-169 | phenyl | COOEt |
| II-A-170, II-B-170, and II-C-170 | 3-OMe-phenyl | COOEt |
| II-A-171, II-B-171, and II-C-171 | 4-F-phenyl | COOEt |
| II-A-172, II-B-172, and II-C-172 | 3-NH₂-phenyl | COOEt |
| II-A-173, II-B-173, and II-C-173 | 3-Cl-phenyl | COOH |
| II-A-174, II-B-174, and II-C-174 | 3-Cl-phenyl | methyl (2S)-2-amido-3-phenylpropanoate group |
| II-A-175, II-B-175, and II-C-175 | 3-Cl-phenyl | tert-butyl 2-amido-2-phenylacetate group |
| II-A-176, II-B-176, and II-C-176 | 3-OMe-phenyl | CONHCH₂(pyrid-4-yl) |
| II-A-177, II-B-177, and II-C-177 | 3,5-dimethoxyphenyl | CONHCH₂(pyrid-4-yl) |
| II-A-178, II-B-178, and II-C-178 | 4-F-phenyl | CONHCH₂(pyrid-3-yl) |
| II-A-179, II-B-179, and II-C-179 | 4-OMe-phenyl | CONHCH₂(pyrid-3-yl) |
| II-A-180, II-B-180, and II-C-180 | 2,5-dimethoxyphenyl | CONHCH₂(pyrid-3-yl) |
| II-A-181, II-B-181, and II-C-181 | 2,5-difluorophenyl | CONHCH₂(pyrid-3-yl) |
| II-A-182, II-B-182, and II-C-182 | 4-F-phenyl | CONHCH₂(tetrahydrofuran-2-yl) |
| II-A-183, II-B-183, and II-C-183 | 4-OMe-phenyl | CONHCH₂(tetrahydrofuran-2-yl) |
| II-A-184, II-B-184, and II-C-184 | 3-F-phenyl | CONHCH₂(tetrahydrofuran-2-yl) |
| II-A-185, II-B-185, and II-C-185 | 3-OMe-phenyl | CONHCH₂(tetrahydrofuran-2-yl) |
| II-A-186, II-B-186, and II-C-186 | 2,5-dimethoxyphenyl | CONHCH₂(tetrahydrofuran-2-yl) |
| II-A-187, II-B-187, and II-C-187 | 2,3-difluorophenyl | CONHCH₂(tetrahydrofuran-2-yl) |
| II-A-188, II-B-188, and II-C-188 | 2,5-difluorophenyl | CONHCH₂(tetrahydrofuran-2-yl) |
| II-A-189, II-B-189, and II-C-189 | 4-F-phenyl | CONHCH₂(1-Et-pyrrolidin-2-yl) |
| II-A-190, II-B-190, and II-C-190 | 4-OMe-phenyl | CONHCH₂(1-Et-pyrrolidin-2-yl) |

-continued

| No. | R² | Q-R⁴ |
|---|---|---|
| II-A-191, II-B-191, and II-C-191 | 3-F-phenyl | CONHCH₂(1-Et-pyrrolidin-2-yl) |
| II-A-192, II-B-192, and II-C-192 | 3-OMe-phenyl | CONHCH₂(1-Et-pyrrolidin-2-yl) |
| II-A-193, II-B-193, and II-C-193 | 2,5-dimethoxyphenyl | CONHCH₂(1-Et-pyrrolidin-2-yl) |
| II-A-194, II-B-194, and II-C-194 | 3,4-difluorophenyl | CONHCH₂(1-Et-pyrrolidin-2-yl) |
| II-A-195, II-B-195, and II-C-195 | 2,3-difluorophenyl | CONHCH₂(1-Et-pyrrolidin-2-yl) |
| II-A-196, II-B-196, and II-C-196 | 2,5-difluorophenyl | CONHCH₂(1-Et-pyrrolidin-2-yl) |
| II-A-197, II-B-197, and II-C-197 | 4-F-phenyl | CO(morpholin-4-yl) |
| II-A-198, II-B-198, and II-C-198 | 4-OMe-phenyl | CO(morpholin-4-yl) |
| II-A-199, II-B-199, and II-C-199 | 3-F-phenyl | CO(morpholin-4-yl) |
| II-A-200, II-B-200, and II-C-200 | 2,5-dimethoxyphenyl | CO(morpholin-4-yl) |
| II-A-201, II-B-201, and II-C-201 | 3,4-difluorophenyl | CO(morpholin-4-yl) |
| II-A-202, II-B-202, and II-C-202 | 2,3-difluorophenyl | CO(morpholin-4-yl) |
| II-A-203, II-B-203, and II-C-203 | 2,5-difluorophenyl | CO(morpholin-4-yl) |
| II-A-204, II-B-204, and II-C-204 | 4-F-phenyl | CO(4-Me-piperidin-1-yl) |
| II-A-205, II-B-205, and II-C-205 | 4-OMe-phenyl | CO(4-Me-piperidin-1-yl) |
| II-A-206, II-B-206, and II-C-206 | 3-F-phenyl | CO(4-Me-piperidin-1-yl) |
| II-A-207, II-B-207, and II-C-207 | 2,5-dimethoxyphenyl | CO(4-Me-piperidin-1-yl) |
| II-A-208, II-B-208, and II-C-208 | 3,4-difluorophenyl | CO(4-Me-piperidin-1-yl) |
| II-A-209, II-B-209, and II-C-209 | 2,3-difluorophenyl | CO(4-Me-piperidin-1-yl) |
| II-A-210, II-B-210, and II-C-210 | 2,5-difluorophenyl | CO(4-Me-piperidin-1-yl) |
| II-A-211, II-B-211, and II-C-211 | 4-Cl-phenyl | CONHCH₂(pyrid-4-yl) |
| II-A-212, II-B-212, and II-C-212 | 3,4-dimethoxyphenyl | CONHCH₂(pyrid-4-yl) |
| II-A-213, II-B-213, and II-C-213 | benzo[1,3]dioxo-5-yl | CONHCH₂(pyrid-4-yl) |
| II-A-214, II-B-214, and II-C-214 | 4-Cl-phenyl | CONHCH₂(pyrid-3-yl) |
| II-A-215, II-B-215, and II-C-215 | 3,4-dimethoxyphenyl | CONHCH₂(pyrid-3-yl) |
| II-A-216, II-B-216, and II-C-216 | benzo[1,3]dioxo-5-yl | CONHCH₂(pyrid-3-yl) |
| II-A-217, II-B-217, and II-C-217 | 4-Cl-phenyl | CONHCH₂(tetrahydrofuran-2-yl) |
| II-A-218, II-B-218, and II-C-218 | 3,4-dimethoxyphenyl | CONHCH₂(tetrahydrofuran-2-yl) |
| II-A-219, II-B-219, and II-C-219 | benzo[1,3]dioxo-5-yl | CONHCH₂(tetrahydrofuran-2-yl) |
| II-A-220, II-B-220, and II-C-220 | 4-Cl-phenyl | CONHCH₂(1-Et-pyrrolidin-2-yl) |
| II-A-221, II-B-221, and II-C-221 | 3,4-dichlorophenyl | CONHCH₂(1-Et-pyrrolidin-2-yl) |
| II-A-222, II-B-222, and II-C-222 | 3-Cl-2-F-phenyl | CONHCH₂(1-Et-pyrrolidin-2-yl) |
| II-A-223, II-B-223, and II-C-223 | 3-Cl-4-F-phenyl | CONHCH₂(1-Et-pyrrolidin-2-yl) |
| II-A-224, II-B-224, and II-C-224 | 3,4-dimethoxyphenyl | CONHCH₂(1-Et-pyrrolidin-2-yl) |
| II-A-225, II-B-225, and II-C-225 | benzo[1,3]dioxo-5-yl | CONHCH₂(1-Et-pyrrolidin-2-yl) |
| II-A-226, II-B-226, and II-C-226 | 3,5-dichlorophenyl | CONHCH₂(1-Et-pyrrolidin-2-yl) |
| II-A-227, II-B-227, and II-C-227 | 4-Cl-phenyl | CO(morpholin-4-yl) |
| II-A-228, II-B-228, and II-C-228 | 3,4-dimethoxyphenyl | CO(morpholin-4-yl) |
| II-A-229, II-B-229, and II-C-229 | benzo[1,3]dioxo-5-yl | CO(morpholin-4-yl) |
| II-A-230, II-B-230, and II-C-230 | 4-Cl-phenyl | CO(4-Me-piperidin-1-yl) |
| II-A-231, II-B-231, and II-C-231 | 3,4-dichlorophenyl | CO(4-Me-piperidin-1-yl) |
| II-A-232, II-B-232, and II-C-232 | 3-Cl-2-F-phenyl | CO(4-Me-piperidin-1-yl) |
| II-A-233, II-B-233, and II-C-233 | 3-Cl-4-F-phenyl | CO(4-Me-piperidin-1-yl) |
| II-A-234, II-B-234, and II-C-234 | 3,4-dimethoxyphenyl | CO(4-Me-piperidin-1-yl) |
| II-A-235, II-B-235, and II-C-235 | benzo[1,3]dioxo-5-yl | CO(4-Me-piperidin-1-yl) |
| II-A-236, II-B-236, and II-C-236 | 3,5-dichlorophenyl | CO(4-Me-piperidin-1-yl) |
| II-A-237, II-B-237, and II-C-237 | 2,3-difluorophenyl | CON(Me)(Et) |
| II-A-238, II-B-238, and II-C-238 | 4-F-phenyl | 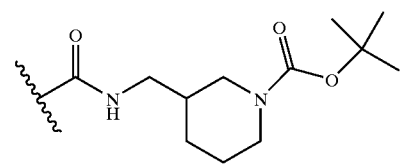 |
| II-A-239, II-B-239, and II-C-239 | 3-OMe-phenyl | 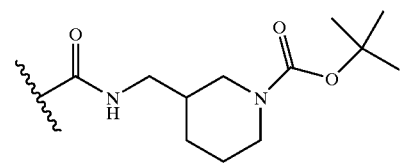 |
| II-A-240, II-B-240, and II-C-240 | 2,5-dimethoxyphenyl | 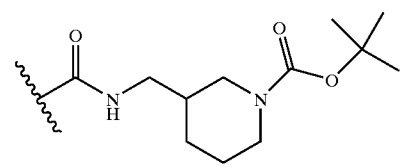 |

-continued

| No. | R² | Q-R⁴ |
|---|---|---|
| II-A-241, II-B-241, and II-C-241 | 3,4-difluorophenyl | *[structure: -C(O)NH-CH₂-(piperidin-3-yl)-N-Boc]* |
| II-A-242, II-B-242, and II-C-242 | 2,3-difluorophenyl | *[structure: -C(O)NH-CH₂-(piperidin-3-yl)-N-Boc]* |
| II-A-243, II-B-243, and II-C-243 | 2,5-difluorophenyl | *[structure: -C(O)NH-CH₂-(piperidin-3-yl)-N-Boc]* |
| II-A-244, II-B-244, and II-C-244 | 3-MeO-phenyl | CONHOCH₂Ph |
| II-A-245, II-B-245, and II-C-245 | 2,5-dimethoxyphenyl | CONHOCH₂Ph |
| II-A-246, II-B-246, and II-C-246 | 3-F-phenyl | *[structure: -C(O)NH-CH₂CH₂-(1H-imidazol-4-yl)]* |
| II-A-247, II-B-247, and II-C-247 | 3-MeO-phenyl | *[structure: -C(O)NH-CH₂CH₂-(1H-imidazol-4-yl)]* |
| II-A-248, II-B-248, and II-C-248 | 3,4-difluorophenyl | *[structure: -C(O)NH-CH₂CH₂-(1H-imidazol-4-yl)]* |
| II-A-249, II-B-249, and II-C-249 | 2,3-difluorophenyl | *[structure: -C(O)NH-CH₂CH₂-(1H-imidazol-4-yl)]* |
| II-A-250, II-B-250, and II-C-250 | 3-Cl-phenyl | *[structure: -C(O)NH-CH₂-(piperidin-3-yl)-N-Boc]* |
| II-A-251, II-B-251, and II-C-251 | 4-Cl-phenyl | *[structure: -C(O)NH-CH₂-(piperidin-3-yl)-N-Boc]* |

-continued

| No. | R² | Q-R⁴ |
|---|---|---|
| II-A-252, II-B-252, and II-C-252 | 4-Cl-phenyl | 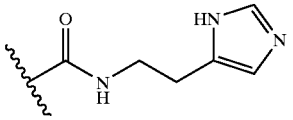 |
| II-A-253, II-B-253, and II-C-253 | 3,4-dichlorophenyl | 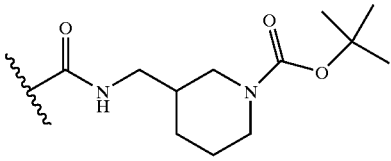 |
| II-A-254, II-B-254, and II-C-254 | 3,4-dichlorophenyl | 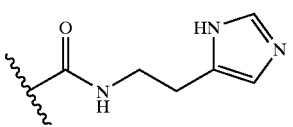 |
| II-A-255, II-B-255, and II-C-255 | 3-Cl-2-F-phenyl | 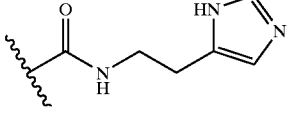 |
| II-A-256, II-B-256, and II-C-256 | 3-Cl-4-F-phenyl | 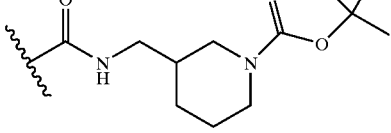 |
| II-A-257, II-B-257, and II-C-257 | 3-Cl-4-F-phenyl | 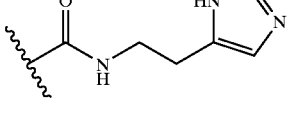 |
| II-A-258, II-B-258, and II-C-258 | 3,4-dimethoxyphenyl | CON(Me)(Et) |
| II-A-259, II-B-259, and II-C-259 | 3,4-dimethoxyphenyl | 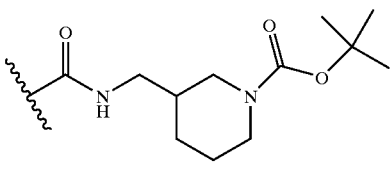 |
| II-A-260, II-B-260, and II-C-260 | 3,4-dimethoxyphenyl | CONHOCH₂Ph |
| II-A-261, II-B-261, and II-C-261 | 3,4-dimethoxyphenyl | 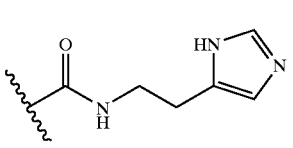 |
| II-A-262, II-B-262, and II-C-262 | benzo[1,3]dioxo-5-yl | CON(Me)(Et) |
| II-A-263, II-B-263, and II-C-263 | benzo[1,3]dioxo-5-yl | 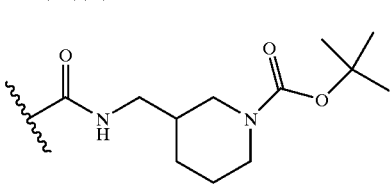 |
| II-A-264, II-B-264, and II-C-264 | benzo[1,3]dioxo-5-yl | CONHOCH₂Ph |

-continued
| No. | R² | Q-R⁴ |
|---|---|---|
| II-A-265, II-B-265, and II-C-265 | benzo[1,3]dioxo-5-yl | 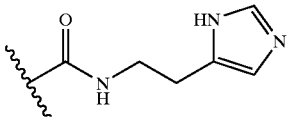 |
| II-A-266, II-B-266, and II-C-266 | 3,5-dichlorophenyl | 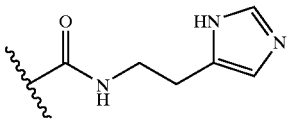 |
| II-A-267, II-B-267, and II-C-267 | 3-Br-phenyl | 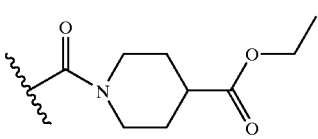 |
| II-A-268, II-B-268, and II-C-268 | 3-Br-phenyl | 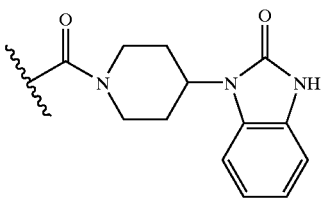 |
| II-A-269, II-B-269, and II-C-269 | 3-Br-phenyl | 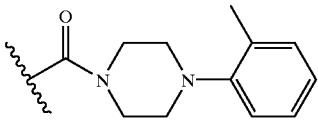 |
| II-A-270, II-B-270, and II-C-270 | 3-Br-phenyl | 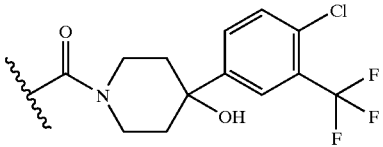 |
| II-A-271, II-B-271, and II-C-271 | 3-Br-phenyl | 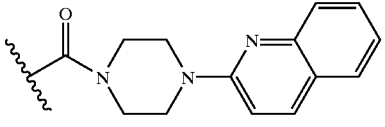 |
| II-A-272, II-B-272, and II-C-272 | 3-Br-phenyl | 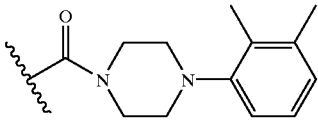 |
| II-A-273, II-B-273, and II-C-273 | 3-Br-phenyl | 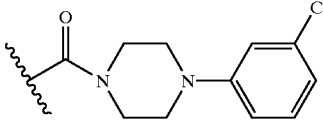 |
| II-A-274, II-B-274, and II-C-274 | 3-Br-phenyl | 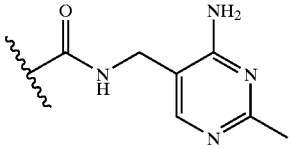 |

-continued

| No. | R² | Q-R⁴ |
|---|---|---|
| II-A-275, II-B-275, and II-C-275 | 3-Br-phenyl | ![structure] |
| II-A-276, II-B-276, and II-C-276 | 3-Br-phenyl | ![structure] |
| II-A-277, II-B-277, and II-C-277 | 3-Br-phenyl | ![structure] |
| II-A-278, II-B-278, and II-C-278 | 3-Br-phenyl | ![structure] |
| II-A-279, II-B-279, and II-C-279 | 3-Br-phenyl | ![structure] |
| II-A-280, II-B-280, and II-C-280 | 3-Br-phenyl | CONH(CH₂)₂COOH |
| II-A-281, II-B-281, and II-C-281 | 3-Br-phenyl | ![structure] |
| II-A-282, II-B-282, and II-C-282 | 3-Br-phenyl | CONHCH₂(4-COOH-phenyl) |
| II-A-283, II-B-283, and II-C-283 | 3-Br-phenyl | ![structure] |

-continued

| No. | R² | Q-R⁴ |
|---|---|---|
| II-A-284, II-B-284, and II-C-284 | 3-Br-phenyl | 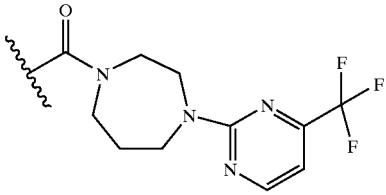 |
| II-A-285, II-B-285, and II-C-285 | 3-NO₂-phenyl | CONHCH₂phenyl |
| II-A-286, II-B-286, and II-C-286 | 3-Cl-phenyl | CONHCH₂(1-Et-pyrrolidin-2-yl) |
| II-A-287, II-B-287, and II-C-287 | 3-(N—Et—NHCO)-phenyl | CONHCH₂phenyl |
| II-A-288, II-B-288, and II-C-288 | 3-Br-phenyl | 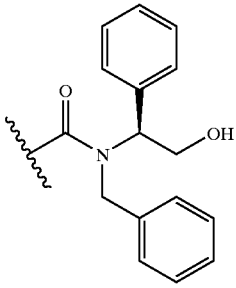 |
| II-A-289, II-B-289, and II-C-289 | 3-NO₂-phenyl | CONHCH₂(pyrid-4-yl) |
| II-A-290, II-B-290, and II-C-290 | 3-Br-phenyl | 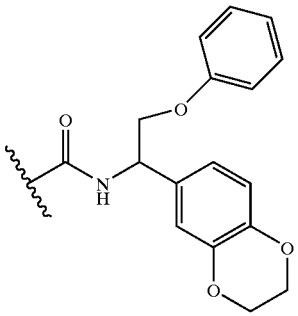 |
| II-A-291, II-B-291, and II-C-291 | 3-F-phenyl | CON(Me)(Et) |
| II-A-292, II-B-292, and II-C-292 | 3-MeO-phenyl | CON(Me)(Et) |
| II-A-293, II-B-293, and II-C-293 | 3-Br-phenyl | 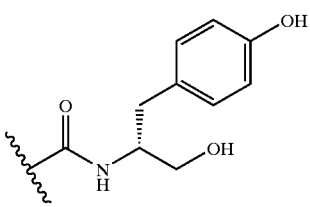 |
| II-A-294, II-B-294, and II-C-294 | 3-Br-phenyl | 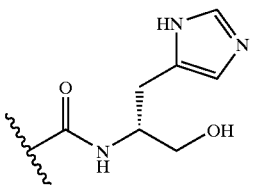 |
| II-A-295, II-B-295, and II-C-295 | 3-Br-phenyl | 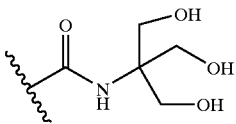 |

-continued

| No. | R² | Q-R⁴ |
|---|---|---|
| II-A-296, II-B-296, and II-C-296 | 3-Br-phenyl | (structure: amide linked to CH(CH₂-3,4-dimethoxyphenyl)CH₂OH) |
| II-A-297, II-B-297, and II-C-297 | phenyl | CONH(CH₂)₂NMe₂ |
| II-A-298, II-B-298, and II-C-298 | 3-MeO-phenyl | CONH(CH₂)₂NMe₂ |
| II-A-299, II-B-299, and II-C-299 | 3-Br-phenyl | CONHCH₂phenyl |
| II-A-300, II-B-300, and II-C-300 | 3-Cl-phenyl | (structure: amide linked to CH(3,4-difluorophenyl)CH₂OH) |
| II-A-301, II-B-301, and II-C-301 | 3-Cl-phenyl | (structure: amide linked to CH(4-fluorophenyl)CH₂OH) |
| II-A-302, II-B-302, and II-C-302 | 3-Cl-phenyl | (structure: amide linked to CH(4-CF₃-phenyl)CH₂OH) |
| II-A-303, II-B-303, and II-C-303 | 3-Cl-phenyl | (structure: amide linked to CH(4-Cl-phenyl)CH₂OH) |
| II-A-304, II-B-304, and II-C-304 | 3-Cl-phenyl | (structure: amide linked to CH(3-Cl-4-F-phenyl)CH₂OH) |
| II-A-305, II-B-305, and II-C-305 | 3-Cl-phenyl | (structure: amide linked to CH(3-Cl-4-F-phenyl)CH₂OH) |

-continued

| No. | R² | Q-R⁴ |
|---|---|---|
| II-A-306, II-B-306, and II-C-306 | 3-Cl-phenyl | (1-(3-fluoro-4-methoxyphenyl)-2-hydroxyethyl)amide |
| II-A-307, II-B-307, and II-C-307 | 3-Cl-phenyl | ((S)-2-acetoxy-1-phenylethyl)amide |
| II-A-308, II-B-308, and II-C-308 | 3-Cl-phenyl | ((S)-2-(methoxycarbonyloxy)-1-phenylethyl)amide |
| II-A-309, II-B-309, and II-C-309 | 3-Cl-phenyl | (1-(4-fluoro-3-methoxyphenyl)-2-hydroxyethyl)amide |
| II-A-310, II-B-310, and II-C-310 | 3,5-dichlorophenyl | ((S)-1-(3-chloro-4-fluorophenyl)-2-hydroxyethyl)amide |
| II-A-311, II-B-311, and II-C-311 | 3-Br-5-CF₃-phenyl | ((S)-2-hydroxy-1-phenylethyl)amide |
| II-A-312, II-B-312, and II-C-312 | 3-Cl-phenyl | (1-(3,5-dichlorophenyl)-2-hydroxyethyl)amide |

-continued
| No. | R² | Q-R⁴ |
|---|---|---|
| II-A-313, II-B-313, and II-C-313 | 3,5-dichlorophenyl | 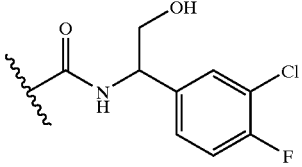 |
| II-A-314, II-B-314, and II-C-314 | 3-Cl-4-CN-phenyl | 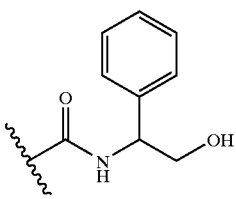 |
| II-A-315, II-B-315, and II-C-315 | 3-Cl-4-CH₂OH-phenyl | 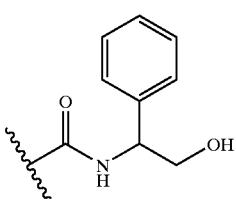 |
| II-A-316, II-B-316, and II-C-316 | 3-Cl-4-CH₂NH₂-phenyl | 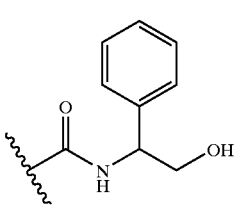 |
| II-A-317, II-B-317, and II-C-317 | 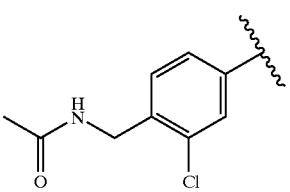 | 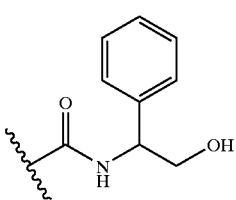 |
| II-A-318, II-B-318, and II-C-318 | 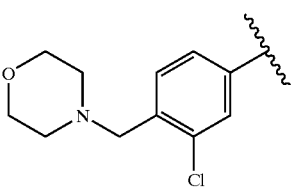 | 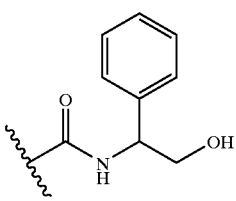 |
| II-A-319, II-B-319, and II-C-319 | 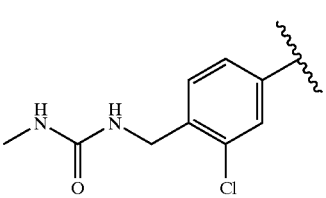 | 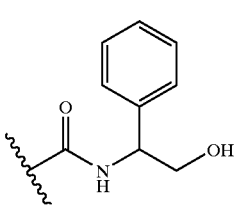 |

-continued

| No. | R² | Q-R⁴ |
|---|---|---|
| II-A-323, II-B-323, and II-C-323 | CH₂Ph | CON(Me)₂ |
| II-A-324, II-B-324, and II-C-324 | cyclopentylmethyl | CO₂NHCH₂Ph |
| II-A-325, II-B-325, and II-C-325 | isopropyl | CN |
| II-A-326, II-B-326, and II-C-326 | 3-Cl-phenyl | NHCOCH₂Ph |
| II-A-327, II-B-327, and II-C-327 | 3-Cl-phenyl | NHSO₂-morpholin-4-yl |
| II-A-328, II-B-328, and II-C-328 | 3-Cl-phenyl | NHCONHCH₂Ph |
| II-A-329, II-B-329, and II-C-329 | 3-Cl-phenyl | NHCO₂-tetrahydrofuran-2-yl |
| II-A-330, II-B-330, and II-C-330 | CH₂Ph | CONHCH₂Ph |
| II-A-331, II-B-331, and II-C-331 | Me | CONHCH₂Ph |
| II-A-332, II-B-332, and II-C-332 | isopropyl | CONHCH₂Ph |
| II-A-333, II-B-333, and II-C-333 | H | CON(Me)₂ |

| No. | R² | Q-R⁴ |
|---|---|---|
| II-A-336, II-B-336, and II-C-336 | 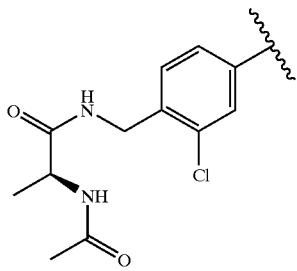 | 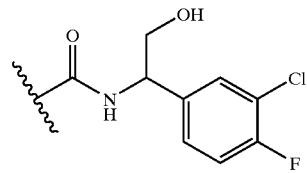 |
| II-A-337, II-B-337, and II-C-337 | 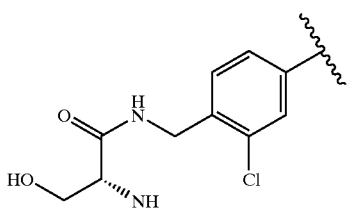 | 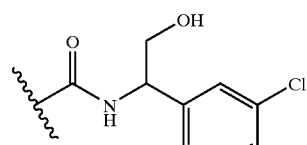 |
| II-A-338, II-B-338, and II-C-338 | 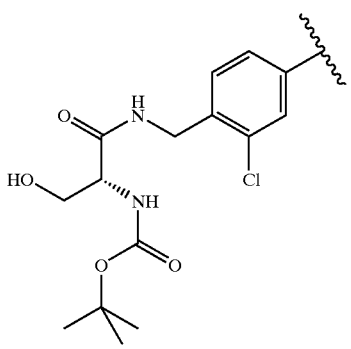 | 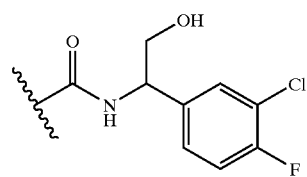 |
| II-A-339, II-B-339, and II-C-339 | 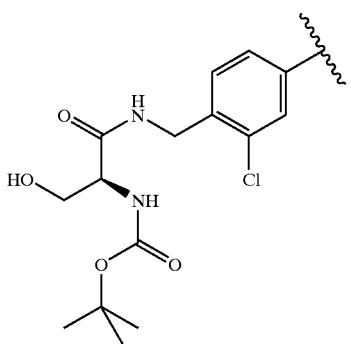 | 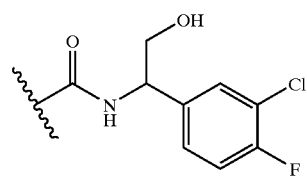 |
| II-A-340, II-B-340, and II-C-340 | 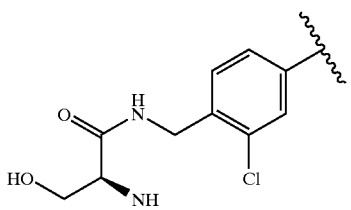 | 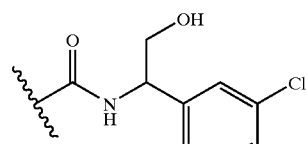 |

| No. | R² | Q-R⁴ |
|---|---|---|
| II-A-341, II-B-341, and II-C-341 | | |
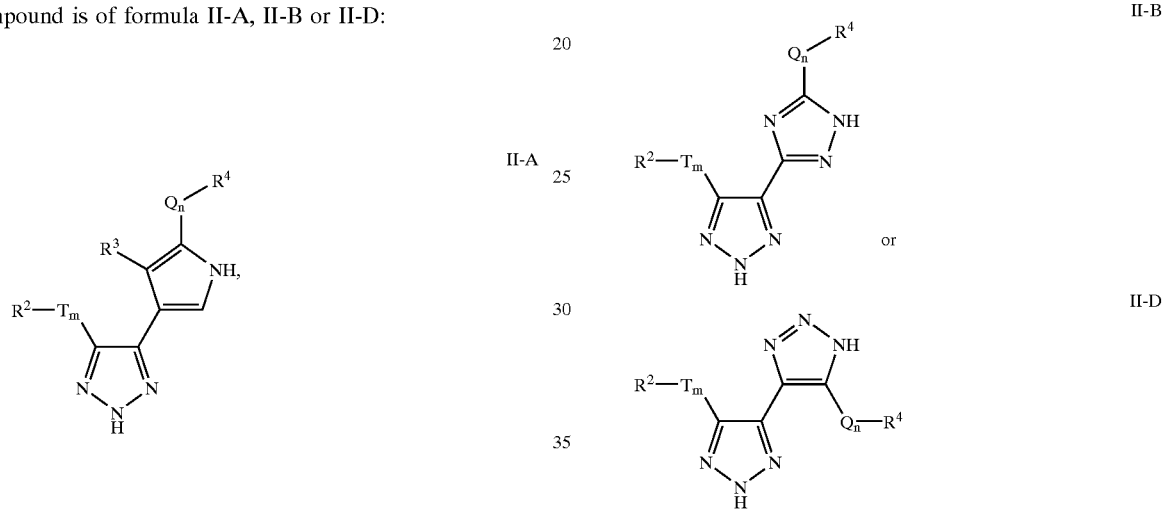
18. The compound according to claim 5 wherein said compound is of formula II-A, II-B or II-D:
and is selected from any one of the following compounds:
| No. | Tₘ-R² | Qₙ-R⁴ |
|---|---|---|
| II-A-342, II-B-342, and II-C-342 | 2-F-3-Cl-phenyl | |
| II-A-343, II-B-343, and II-C-343 | methyl | |
| II-A-344, II-B-344, and II-C-344 | methyl | |

| No. | $T_m-R^2$ | $Q_n-R^4$ |
|---|---|---|
| II-A-345, II-B-345, and II-C-345 | Methyl | *(S)-2-hydroxy-1-phenylethyl amide, propanol chain)* |
| II-A-346, II-B-346, and II-C-346 | 3,5-dichlorophenyl | *(2-hydroxy-1-phenylethyl amide)* |
| II-A-347, II-B-347, and II-C-347 | 3-F, 5-CF$_3$-phenyl | *(2-hydroxy-1-phenylethyl amide)* |
| II-A-348, II-B-348, and II-C-348 | Methyl | *(2-hydroxy-1-phenylethyl amide)* |
| II-A-349, II-B-349, and II-C-349 | H | *(N-methyl, methyl, phenyl, OH substituted amide)* |
| II-A-350, II-B-350, and II-C-350 | Methyl | *(leucinol amide)* |
| II-A-351, II-B-351, and II-C-351 | Methyl | *(histidinol amide)* |
| II-A-352, II-B-352, and II-C-352 | Methyl | *(3-chloro-4-fluorophenyl hydroxyethyl amide)* |
| II-A-353, II-B-353, and II-C-353 | Cyclohexyl | *(2-hydroxy-1-phenylethyl amide)* |

| No. | $T_m$-$R^2$ | $Q_n$-$R^4$ |
|---|---|---|
| II-A-354, II-B-354, and II-C-354 | Cyclopropyl | 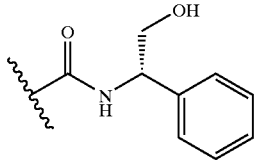 |
| II-A-355, II-B-355, and II-C-355 | Methyl | 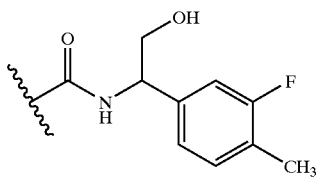 |
| II-A-356, II-B-356, and II-C-356 | Methyl | 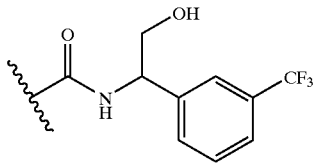 |
| II-A-357, II-B-357, and II-C-357 | CH$_2$OCH$_3$ | 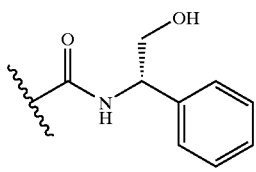 |
| II-A-358, II-B-358, and II-C-358 | CH$_2$OH | 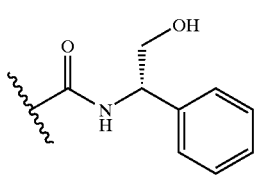 |
| II-A-359, II-B-359, and II-C-359 | Methyl | 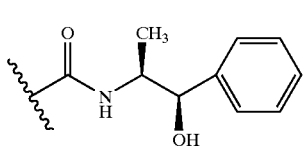 |
| II-A-360, II-B-360, and II-C-360 | Methyl | 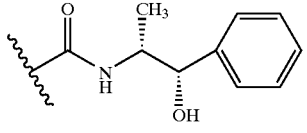 |
| II-A-361, II-B-361, and II-C-361 | Methyl | 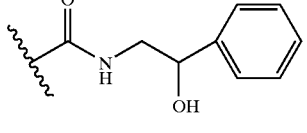 |
| II-A-362, II-B-362, and II-C-362 | Methyl | 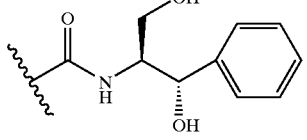 |

-continued

| No. | $T_m$-$R^2$ | $Q_n$-$R^4$ |
|---|---|---|
| II-A-363, II-B-363, and II-C-363 | Methyl | *structure: acyl-NH-CH(CH2OH)-CH(OH)-phenyl* |
| II-A-364, II-B-364, and II-C-364 | H | *structure: acyl-NH-CH(CH3)-CH(OH)-phenyl* |
| II-A-365, II-B-365, and II-C-365 | H | *structure: acyl-NH-CH(CH3)-CH(OH)-phenyl (stereoisomer)* |
| II-A-366, II-B-366, and II-C-366 | H | *structure: acyl-N(CH3)-CH2-CH(OH)-phenyl* |
| II-A-367, II-B-367, and II-C-367 | H | *structure: acyl-N(CH3)-CH2-CH(OH)-phenyl (stereoisomer)* |
| II-A-368, II-B-368, and II-C-368 | H | *structure: acyl-N(CH3)-CH(CH3)-CH(OH)-phenyl* |
| II-A-369, II-B-369, and II-C-369 | H | *structure: acyl-N(CH3)-CH(CH3)-CH(OH)-phenyl (stereoisomer)* |
| II-A-370, II-B-370, and II-C-370 | Methyl | *structure: acyl-NH-CH(CH2OH)-(3-pyridyl)* |
| II-A-371, II-B-371, and II-C-371 | Methyl | *structure: acyl-NH-CH(CH2OH)-(3-fluoro-5-trifluoromethylphenyl)* |

| No. | $T_m$-$R^2$ | $Q_n$-$R^4$ |
|---|---|---|
| II-A-372, II-B-372, and II-C-372 | Methyl | 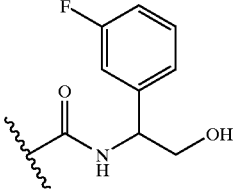 |
| II-A-373, II-B-373, and II-C-373 | Methyl | 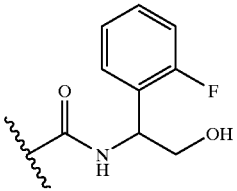 |
| II-A-374, II-B-374, and II-C-374 | Methyl | 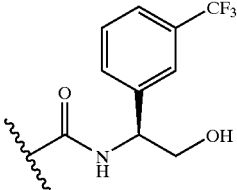 |
| II-A-375, II-B-375, and II-C-375 | Methyl | 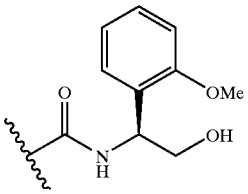 |
| II-A-376, II-B-376, and II-C-376 | Methyl | 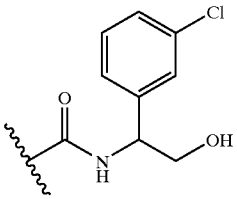 |
| II-A-377, II-B-377, and II-C-377 | Methyl | 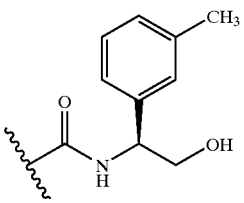 |
| II-A-378, II-B-378, and II-C-378 | Methyl | 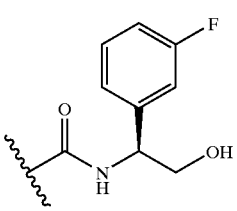 |

| No. | $T_m$-$R^2$ | $Q_n$-$R^4$ |
|---|---|---|
| II-A-379, II-B-379, and II-C-379 | Methyl | 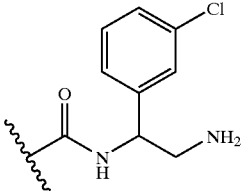 |
| II-A-380, II-B-380, and II-C-380 | methyl | 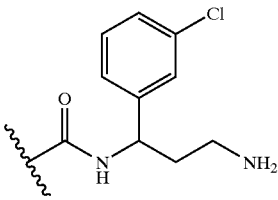 |
| II-A-381, II-B-381, and II-C-381 | H | 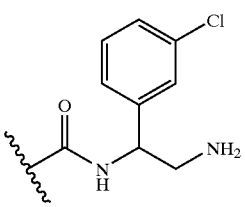 |
| II-A-382, II-B-382, and II-C-382 | H | 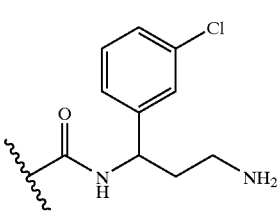 |
| II-A-383, II-B-383, and II-C-383 | 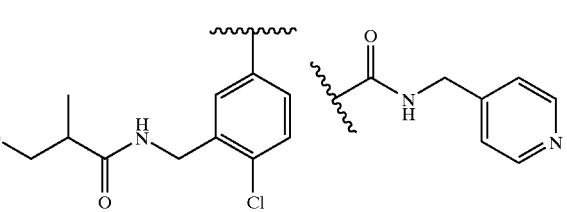 | 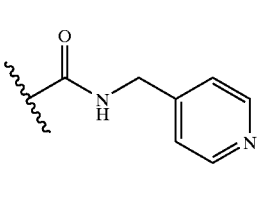 |
| II-A-384, II-B-384, and II-C-384 | 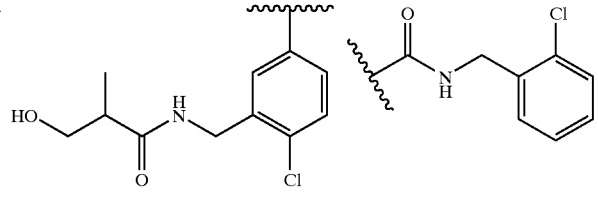 | 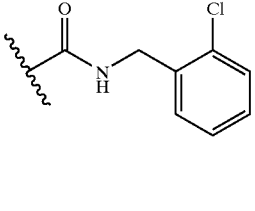 |
| II-A-385, II-B-385, and II-C-385 | 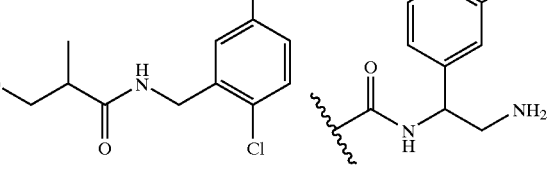 | 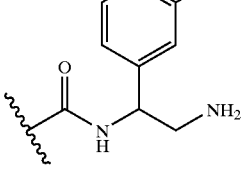 |

-continued

| No. | $T_m$-$R^2$ | $Q_n$-$R^4$ |
|---|---|---|
| II-A-386, II-B-386, and II-C-386 | [structure: HO-CH2-CH(CH3)-C(=O)-NH-CH2-(2-chloro-5-substituted phenyl)] | [structure: -C(=O)-NH-CH(3-chlorophenyl)-CH2-NH2] |
| II-A-387, II-B-387, and II-C-387 | [structure: HO-CH2-CH(NH2)-C(=O)-NH-CH2-(2-chloro-5-substituted phenyl)] | [structure: -C(=O)-NH-CH2-(4-pyridyl)] |
| II-A-388, II-B-388, and II-C-388 | [structure: HO-CH2-CH(NH2)-C(=O)-NH-CH2-(2-chloro-5-substituted phenyl)] | [structure: -C(=O)-NH-CH2-(2-chlorophenyl)] |
| II-A-389, II-B-389, and II-C-389 | [structure: HO-CH2-CH(NH2)-C(=O)-NH-CH2-(2-chloro-5-substituted phenyl)] | [structure: -C(=O)-NH-CH(3-chlorophenyl)-CH2-NH2] |
| II-A-390, II-B-390, and II-C-390 | [structure: HO-CH2-CH(NH2)-C(=O)-NH-CH2-(2-chloro-5-substituted phenyl)] | [structure: -C(=O)-NH-CH(3-chlorophenyl)-CH2-CH2-NH2] |

19. The compound according to claim 5 wherein said compound is selected from any one of the following compounds:

| No. | Structure |
|---|---|
| I-A 1 | [structure: pyrrole-2-carboxamide-N-CH2-(2,3-dihydrobenzofuran-5-yl); pyrrole-4-yl connected to triazole bearing 3-chloro-4-(dimethylaminomethyl)phenyl] |
| I-A 2 | [structure: pyrrole-2-carboxamide-N-CH2-(4-pyridyl); pyrrole-4-yl connected to triazole bearing 3-chloro-4-(hydroxymethyl)phenyl] |

-continued
| No. | Structure |
|---|---|
| I-A 3 | 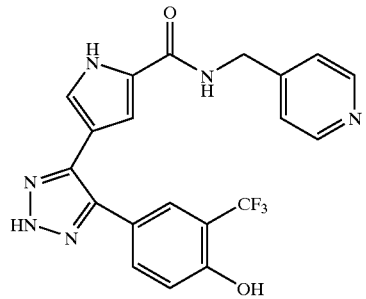 |
| I-A 4 | 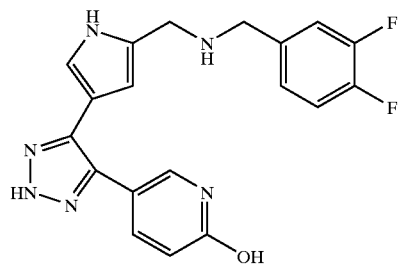 |
| I-A 5 | 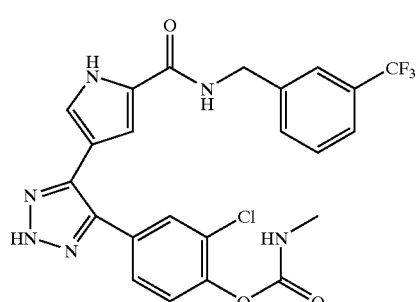 |
| I-A 6 | 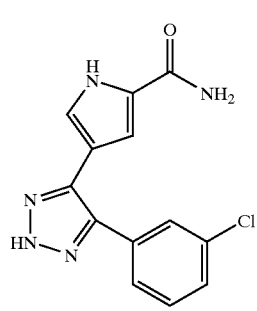 |
| I-A 7 | 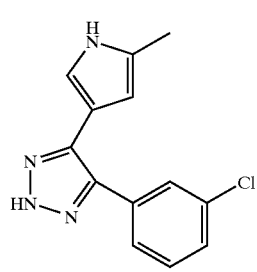 |
-continued
| No. | Structure |
|---|---|
| I-A 8 | 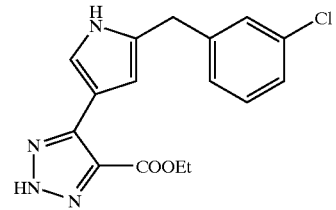 |
| I-B 1 | 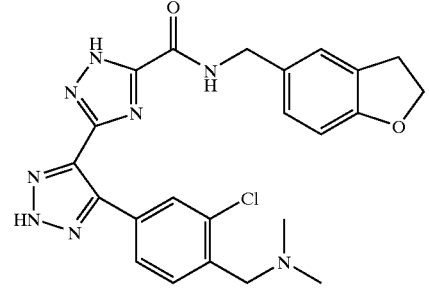 |
| I-B 2 | 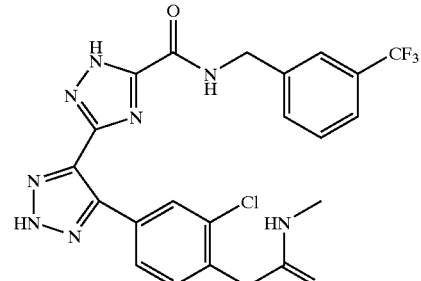 |
| I-B 3 | 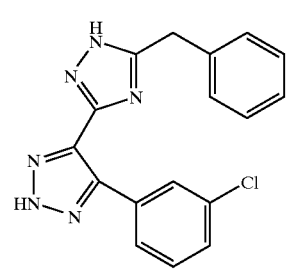 |
| I-B 4 | 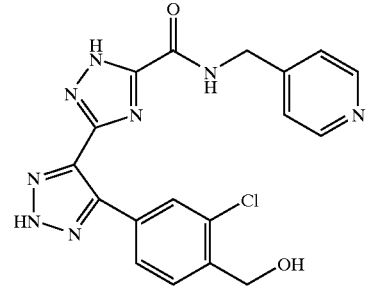 |

-continued
| No. | Structure |
|---|---|
| I-B 5 | 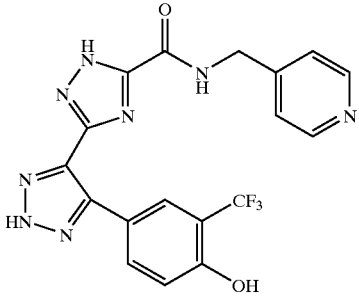 |
| I-B 6 | 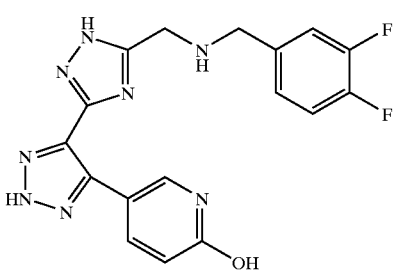 |
| I-C 1 | 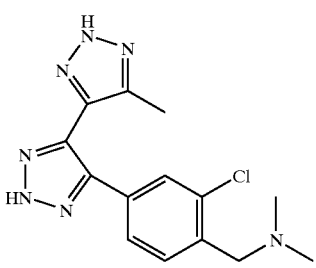 |
| I-C 2 | 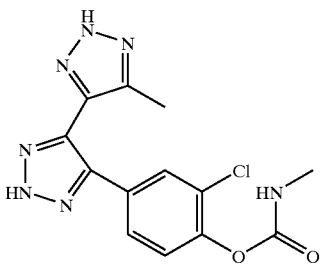 |
| I-C 3 | 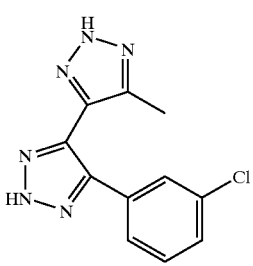 |
-continued
| No. | Structure |
|---|---|
| I-C 4 | 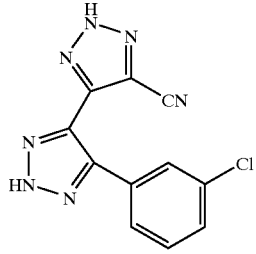 |
| I-C 5 | 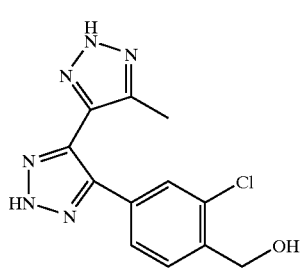 |
| I-C 6 | 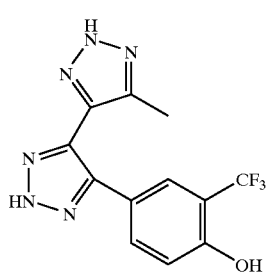 |
| I-C 7 | 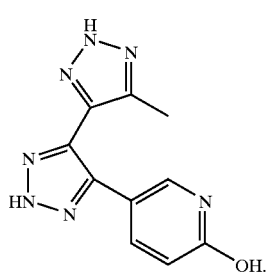 |
20. The compound according to claim 5 wherein said compound is selected from any of the following compounds:
| No. | Structure |
|---|---|
| II-A 9 | 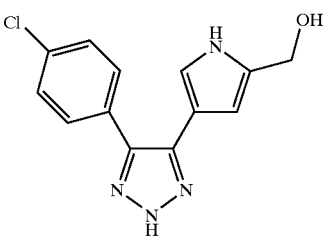 |

| No. | Structure |
|---|---|
| II-A 10 | 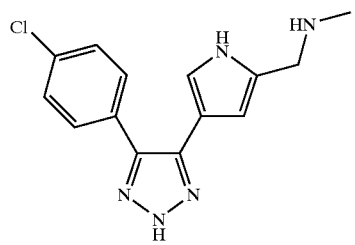 |
| II-A 11 | 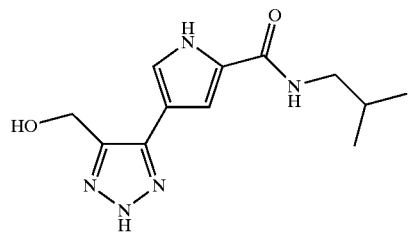 |
| II-A 12 | 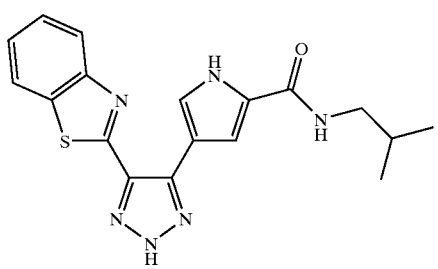 |
| II-A 13 | 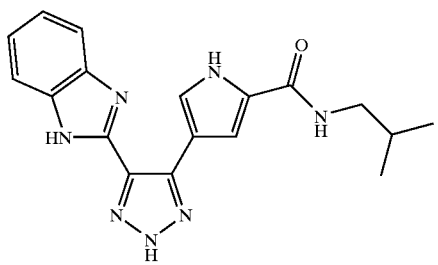 |
| II-A 14 | 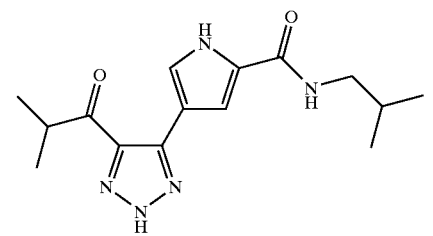 |
| II-A 15 | 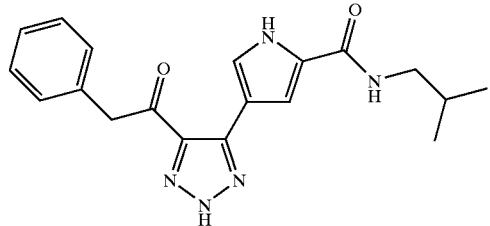 |
| II-A 16 | 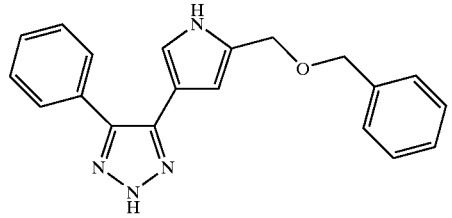 |
| II-A 17 | 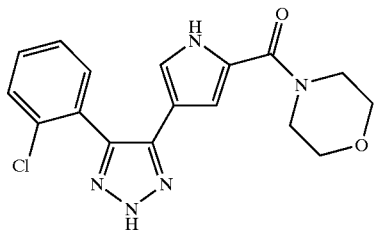 |
| II-A 18 | 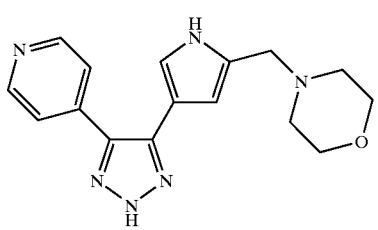 |
| II-A 19 | 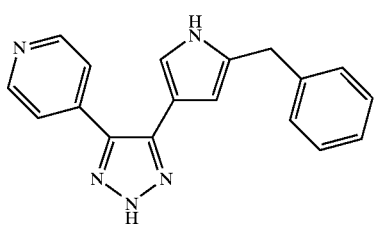 |
| II-A 20 | 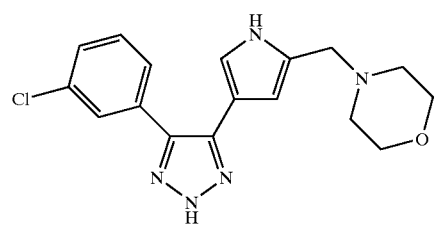 |
| II-A 21 | 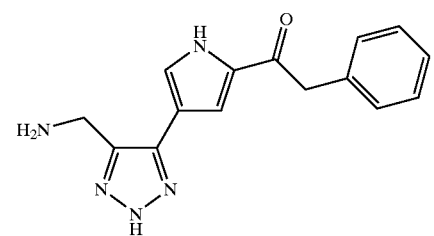 |

-continued
| No. | Structure |
|---|---|
| II-A 22 | 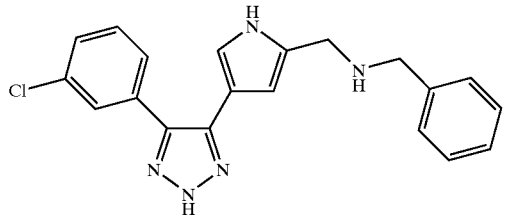 |
| II-A 23 | 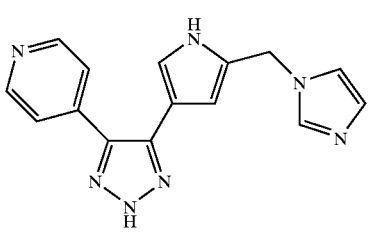 |
| II-A 24 | 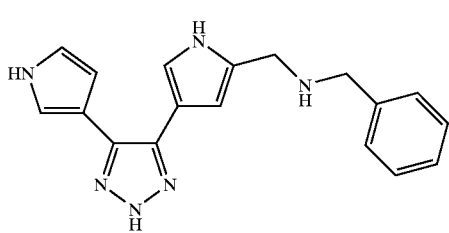 |
| II-A 25 | 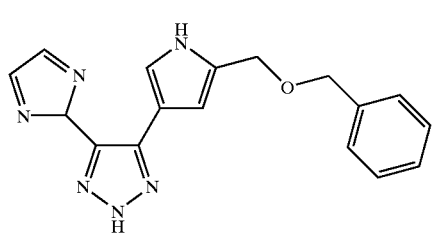 |
| II-A 26 | 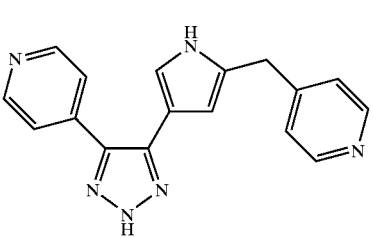 |
| II-A 27 | 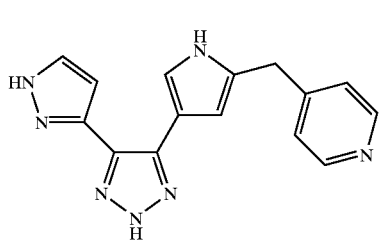 |
-continued
| No. | Structure |
|---|---|
| II-A 28 | 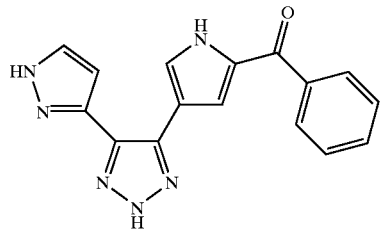 |
| II-A 29 | 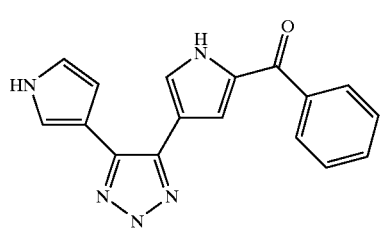 |
| II-A 30 | 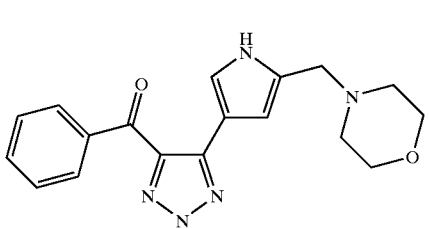 |
| II-A 31 | 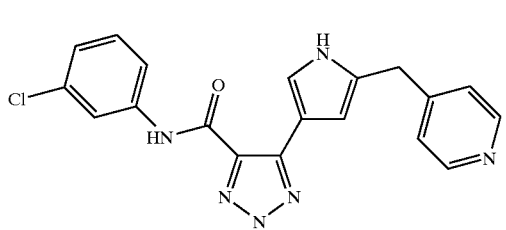 |
| II-A 32 | 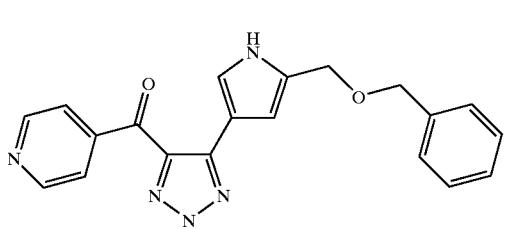 |
| II-A 33 | 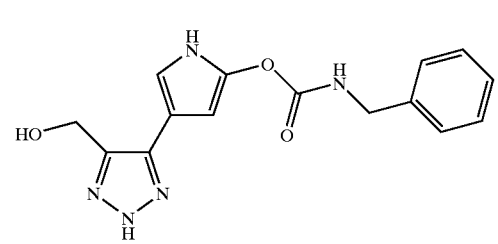 |

-continued

| No. | Structure |
|---|---|
| II-A 34 | 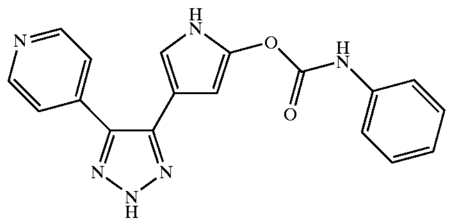 |
| II-A 35 | 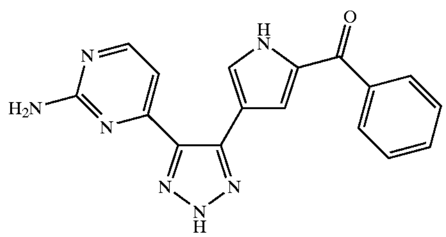 |
| II-A 36 | 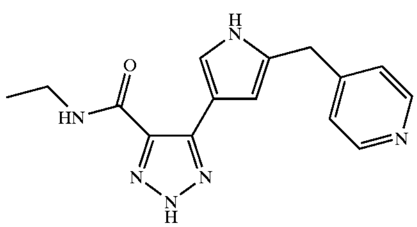 |

-continued

| No. | Structure |
|---|---|
| II-A 37 | 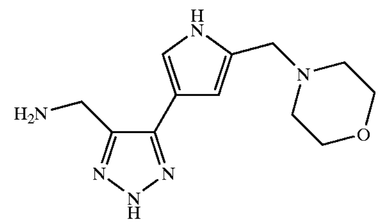 |
| II-A 38 | 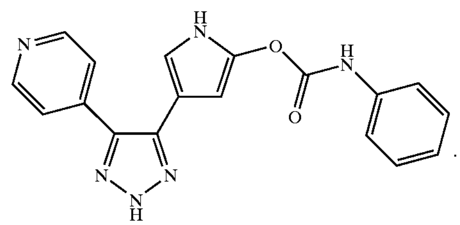 |

21. A composition comprising a compound according to any one of claim 1, 2, or 3, and a pharmaceutically acceptable carrier, adjuvant, or vehicle.

22. The composition according to claim 21, additionally comprising an additional therapeutic agent selected from an anti-proliferative agent, an anti-inflammatory agent, an immunomodulatory agent, a neurotrophic factor, an agent for treating ca diovascular disease, an agent for treating liver disease, an anti-viral agent, an agent for treating blood disorders, an agent for treating diabetes, or an agent for treating immunodeficiency disorders.

* * * * *